US012298314B2

(12) United States Patent
McDonnell et al.

(10) Patent No.: US 12,298,314 B2
(45) Date of Patent: *May 13, 2025

(54) METHODS AND COMPOSITIONS FOR ANALYZING TARGET BINDING OF MOLECULES

(71) Applicant: 10x Genomics, Inc., Pleasanton, CA (US)

(72) Inventors: Wyatt James McDonnell, Concord, CA (US); Michael John Terry Stubbington, Cambridge (GB); Geoffrey McDermott, Livermore, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 231 days.

This patent is subject to a terminal disclaimer.

(21) Appl. No.: 17/497,135

(22) Filed: Oct. 8, 2021

(65) Prior Publication Data

US 2022/0113318 A1     Apr. 14, 2022

Related U.S. Application Data

(60) Provisional application No. 63/090,143, filed on Oct. 9, 2020.

(51) Int. Cl.
*G01N 33/68* (2006.01)
*G01N 33/532* (2006.01)

(52) U.S. Cl.
CPC ....... *G01N 33/6857* (2013.01); *G01N 33/532* (2013.01)

(58) Field of Classification Search
CPC ............. G01N 33/6857; G01N 33/532; G01N 33/6854; G01N 2458/10; G01N 2500/10
See application file for complete search history.

(56) References Cited

U.S. PATENT DOCUMENTS

| | | | |
|---|---|---|---|
| 10,053,683 B2 | 8/2018 | Pasqual et al. | |
| 10,526,379 B2 | 1/2020 | Howarth | |
| 10,550,429 B2 | 2/2020 | Harada et al. | |
| 10,858,702 B2* | 12/2020 | Lucero ................ | C12Q 1/6869 |
| 2010/0105112 A1 | 4/2010 | Holtze et al. | |
| 2014/0155295 A1 | 6/2014 | Hindson et al. | |
| 2014/0378345 A1 | 12/2014 | Hindson et al. | |
| 2015/0292988 A1 | 10/2015 | Bharadwaj et al. | |
| 2015/0376609 A1 | 12/2015 | Hindson et al. | |
| 2018/0105808 A1 | 4/2018 | Mikkelsen et al. | |
| 2018/0179590 A1* | 6/2018 | Belgrader ............ | C12N 15/1075 |
| 2018/0216162 A1 | 8/2018 | Belhocine et al. | |
| 2019/0064173 A1 | 2/2019 | Bharadwaj et al. | |
| 2019/0100632 A1 | 4/2019 | Delaney et al. | |
| 2019/0177800 A1 | 6/2019 | Boutet et al. | |
| 2019/0233878 A1 | 8/2019 | Delaney et al. | |
| 2019/0323088 A1 | 10/2019 | Boutet et al. | |
| 2019/0367969 A1 | 12/2019 | Belhocine et al. | |
| 2019/0367997 A1 | 12/2019 | Bent et al. | |
| 2020/0002764 A1* | 1/2020 | Belgrader ............ | C12Q 1/6874 |
| 2020/0115422 A1 | 4/2020 | Howarth et al. | |

FOREIGN PATENT DOCUMENTS

| | | |
|---|---|---|
| WO | WO 2011098772 A1 | 8/2011 |
| WO | WO 2018075693 A1 | 4/2018 |
| WO | WO 2018112423 A1 | 6/2018 |
| WO | WO 2018119447 A2 | 6/2018 |
| WO | WO 2019157529 A1 | 8/2019 |
| WO | WO 2020167862 A1 | 8/2020 |
| WO | WO 2020176882 A1 | 9/2020 |

OTHER PUBLICATIONS

Gilbert et al., "Genome-Scale CRISPR-Mediated Control of Gene Repression and Activation," *Cell* 159:647-661, Oct. 23, 2014. (15 pages).
Hein et al., "Click Chemistry, A Powerful Tool for Pharmaceutical Sciences," *Pharmaceutical Research* 25(10):2216-2230, Oct. 2008 [Published online May 29, 2008]. (15 pages).
Horlbeck et al., "Compact and highly active next-generation libraries for CRISPR-mediated gene repression and activation," *eLife* 5:e19760, Sep. 23, 2016. (20 pages).
Hughes et al., "Choose Your Label Wisely: Water-Soluble Fluorophores Often Interact with Lipid Bilayers," *PLoS ONE* 9(2):e87649, Feb. 4, 2014. (8 pages).
Kolb et al., "Click Chemistry: Diverse Chemical Function from a Few Good Reactions," *Angewandte Chemie International Edition* 40:2004-2021, May 28, 2001. (18 pages).
Madl et al., "Bioorthogonal Strategies for Engineering Extracellular Matrices," *Advanced Functional Materials* 28(11), Mar. 14, 2018 (HHS Public Access Author Manuscript, available in PMC Sep. 26, 2019). (41 pages).
Pasqual et al., "Monitoring T cell-dendritic cell interactions in vivo by intercellular enzymatic labelling," *Nature* 553(7689):496-500, Jan. 25, 2018 (HHS Public Access Author Manuscript, available in PMC Jul. 25, 2018). (28 pages).
Qi et al., "Repurposing CRISPR as an RNA-Guided Platform for Sequence-Specific Control of Gene Expression," *Cell* 152:1173-1183, Feb. 28, 2013. (13 pages).
Replogle et al., "Combinatorial single-cell CRISPR screens by direct guide RNA capture and targeted sequencing," *Nature Biotechnology* 38(8):954-961, Aug. 2020 (HHS Public Access Author Manuscript, available in PMC Sep. 30, 2020). (23 pages).
Roth et al., "Reprogramming human T cell function and specificity with non-viral genome targeting," *Nature* 559(7714):405-409, Jul. 2018 (HHS Public Access Author Manuscript, available in PMC Jan. 11, 2019). (41 pages).

(Continued)

*Primary Examiner* — Shafiqul Haq
(74) *Attorney, Agent, or Firm* — Seed IP Law Group LLP

(57) ABSTRACT

The present disclosure relates in some aspects to methods and compositions for assessing the target binding capacity of a binding molecule, such as an antigen binding molecule, e.g., a monoclonal antibody. In some embodiments, provided herein is a method of analyzing binding of a barcode-labeled antibody to a target antigen expressed by a cell, wherein cells expressing the candidate antigens are partitioned and wherein detection of the barcoded nucleic acid molecule is indicative of the binding between the antibody or antigen-binding fragment thereof and the candidate antigen or epitope of the cell.

19 Claims, 16 Drawing Sheets

(56) References Cited

OTHER PUBLICATIONS

Shelbourne et al., "Fast copper-free click DNA ligation by the ring-strain promoted alkyne-azide cycloaddition reaction," *Chemical Communications* 47:6257-6259, Jun. 2011. (4 pages).
Spitale et al., "Structural imprints in vivo decode RNA regulatory mechanisms," *Nature* 519:486-490, Mar. 26, 2015 (with Extended Data). (18 pages).
Stoeckius et al., "Cell Hashing with barcoded antibodies enables multiplexing and doublet detection for single cell genomics," *Genome Biology* 19:224, Dec. 19, 2018. (12 pages).

* cited by examiner

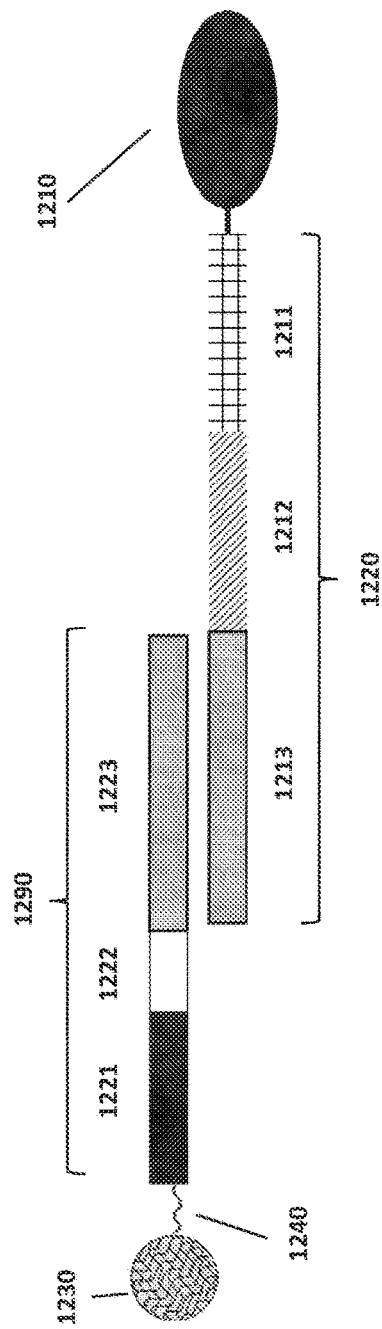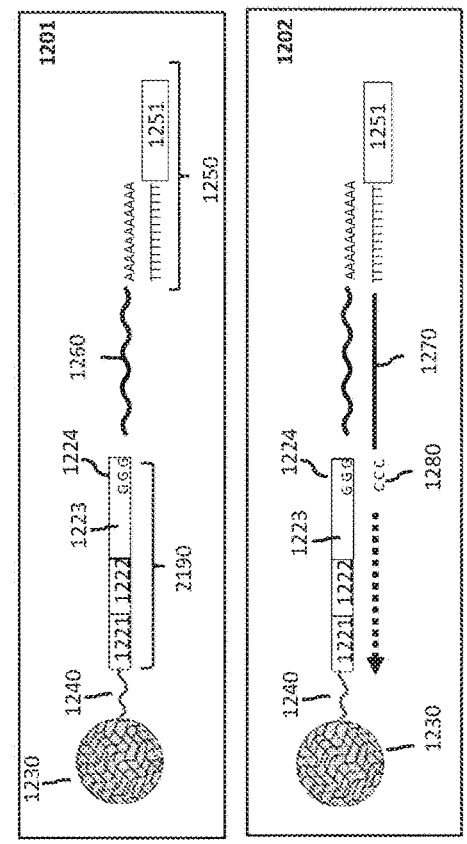
FIG. 12A
FIG. 12B

US 12,298,314 B2

METHODS AND COMPOSITIONS FOR ANALYZING TARGET BINDING OF MOLECULES

FIELD

The present disclosure relates in some aspects to methods and compositions for assessing binding interactions, such as the binding specificity and/or affinity of an antibody to an antigen or epitope.

BACKGROUND

Selection of specific binders to a target of interest, e.g., antibody candidates for targeting an antigen or epitope, is an arduous and frequently low throughput process. Methods exist to accelerate the process of identifying antibody candidates, however, isolated candidates must still be confirmed as antigen-specific in a number of low-throughput assays such as ELISA and Surface Plasmon Resonance (SPR), and in some instances by crystallizing an antibody and a target, which can be challenging for complex molecular targets of the antibody due to stability/inability to form pure crystals. Improved methods to assess an antibody's target binding specificity and/or affinity is needed. The present disclosure addresses these and other needs.

SUMMARY

Provided herein in some aspects are methods and compositions for assessing the target binding capacity of a binding molecule, such as an antigen binding molecule, e.g., a monoclonal antibody.

In some embodiments, provided herein is a method of analyzing an antibody or antigen-binding fragment thereof, comprising: contacting an antibody or antigen-binding fragment thereof coupled to a reporter oligonucleotide comprising an antibody barcode sequence with a cell population comprising one or more cells expressing a candidate antigen or epitope, (a) wherein all or a subset of the cells of the population are partitioned into a plurality of partitions, wherein upon partitioning, a partition of the plurality of partitions comprises a cell of the population or subset thereof and nucleic acid barcode molecules comprising a partition-specific barcode sequence, (b) wherein when the antibody or antigen-binding fragment thereof binds the candidate antigen or epitope, a barcoded nucleic acid molecule is generated in the partition, wherein the barcoded nucleic acid molecule comprises (i) a sequence corresponding to the antibody barcode sequence and (ii) a sequence corresponding to the partition-specific barcode sequence, and (c) wherein the barcoded nucleic acid molecule is indicative of the binding between the antibody or antigen-binding fragment thereof and the candidate antigen or epitope of the cell.

In any of the preceding embodiments, the candidate antigen or epitope can comprise a polynucleotide, a polypeptide, a lipid, a carbohydrate, a small molecule, or one or more other organic or inorganic molecules, or any combination, complex, or conjugate thereof.

In any of the preceding embodiments, the candidate antigen or epitope can comprise a substrate of an enzyme, wherein the substrate is acted on by an enzyme coupled to a nucleic acid molecule, and wherein the presence or absence of the enzyme is detected in the partition, optionally wherein the enzymatic action comprises removal of a carbohydrate moiety from the candidate antigen or epitope.

In any of the preceding embodiments, the one or more cells can comprise a detectable marker indicative of expression or presence of the candidate antigen or epitope by the one or more cells.

In any of the preceding embodiments, the detectable marker can comprise a nucleic acid sequence.

In any of the preceding embodiments, the nucleic acid sequence can be conjugated to a polynucleotide, a polypeptide, a lipid, a carbohydrate, a small molecule, or one or more other organic or inorganic molecules, or any combination, complex, or conjugate thereof.

In any of the preceding embodiments, the nucleic acid sequence can comprise an expression status barcode sequence.

In any of the preceding embodiments, the expression status barcode can be conjugated to an antibody or antigen-binding fragment thereof capable of recognizing a marker of the one or more cells expressing the candidate antigen or epitope, optionally wherein the marker is not the candidate antigen or epitope, whereby the expression status barcode is indicative of expression of the candidate antigen or epitope.

In any of the preceding embodiments, the expression status barcode sequence can be conjugated to a lipid capable of introducing the expression status barcode sequence onto and/or into the one or more cells expressing the candidate antigen or epitope, whereby the expression status barcode is indicative of expression of the candidate antigen or epitope.

In any of the preceding embodiments, the nucleic acid sequence can comprise: (i) a sequence expressing the candidate antigen or epitope, optionally wherein all or a portion of the sequence is exogenous to the one or more cells; (ii) a sequence expressing a detectable polypeptide (e.g., a fluorescent protein such as GFP, BFP, RFP, or YFP) or other surface marker, such as CD45 for B cells) indicative of expression of the candidate antigen or epitope; and/or (iii) a sequence indicative of the sequence of (ii).

In any of the preceding embodiments, the nucleic acid barcode molecules comprising the partition-specific barcode sequence may be attached to a bead, optionally wherein the bead is a gel bead, optionally wherein the nucleic acid barcode molecules are releasably attached to the bead.

In any of the preceding embodiments, the one or more cells expressing the candidate antigen or epitope may not be engineered or otherwise modified to induce the presence of the candidate antigen or epitope.

In any of the preceding embodiments, the one or more cells can be engineered or otherwise modified to express the candidate antigen or epitope.

In any of the preceding embodiments, the cell population can further comprise one or more cells that do not express or bear the candidate antigen or epitope.

In any of the preceding embodiments, the cell population can further comprise one or more cells that are engineered or otherwise modified to express a lower level of the candidate antigen or epitope compared to the one or more cells prior to the engineering or modification or compared to the one or more cells that are not so engineered or modified.

In any of the preceding embodiments, the engineering or modification can comprise regulating a polynucleotide encoding, or controlling or regulating expression of, the candidate antigen or epitope.

In any of the preceding embodiments, the engineering or modification can comprise knocking down or knocking out a polynucleotide encoding the candidate antigen or epitope, and/or a complementary sequence thereof.

In any of the preceding embodiments, wherein the engineering or modification can comprise introducing into the one or more cells a gRNA.

In any of the preceding embodiments, the gRNA can be barcoded.

In any of the preceding embodiments, the cell population can comprise: (i) one or more cells that do not express the candidate antigen or epitope, (ii) one or more cells engineered or otherwise modified to express or to increase expression of the candidate antigen or epitope, (iii) one or more cells engineered or otherwise modified to not express or to decrease expression of the candidate antigen or epitope, and/or (iv) one or more cells that do not express the candidate antigen or epitope and that comprise a modification to eliminate or decrease expression of the candidate antigen or epitope, optionally wherein the modification is the same as that of (iii).

In any of the preceding embodiments, the partition comprising the cell expressing the candidate antigen or epitope is a first partition, and the cell in the first partition can comprise a first nucleic acid sequence indicative of expression of the candidate antigen or epitope by the cell, optionally wherein the first nucleic acid sequence is or comprises a first expression status barcode.

In any of the preceding embodiments, a barcoded nucleic acid molecule can be generated in the first partition, wherein the barcoded nucleic acid molecule comprises (i) a sequence corresponding to the first nucleic acid sequence indicative of expression of the candidate antigen or epitope by the cell and (ii) a sequence corresponding to the partition-specific barcode sequence in the first partition, whereby the barcoded nucleic acid molecule is indicative of expression of the candidate antigen or epitope by the cell.

In any of the preceding embodiments, the method can comprise detecting (i) the barcoded nucleic acid molecule indicative of the binding between the antibody or antigen-binding fragment thereof and the candidate antigen or epitope of the cell, and (ii) the barcoded nucleic acid molecule indicative of expression of the candidate antigen or epitope by the cell.

In any of the preceding embodiments, the plurality of partitions can further comprise a second partition comprising a cell that does not express the candidate antigen or epitope.

In any of the preceding embodiments, the cell in the second partition may not be bound by the antibody or antigen-binding fragment thereof, and a barcoded nucleic acid molecule indicative of the binding between the antibody or antigen-binding fragment thereof and the candidate antigen or epitope of the cell may not be generated in the second partition.

In any of the preceding embodiments, the cell in the second partition can comprise a second nucleic acid sequence indicative of no expression of the candidate antigen or epitope by the cell, optionally wherein the second nucleic acid sequence is or comprises a second expression status barcode.

In any of the preceding embodiments, a barcoded nucleic acid molecule can be generated in the second partition, wherein the barcoded nucleic acid molecule comprises (i) a sequence corresponding to the second nucleic acid sequence indicative of no expression of the candidate antigen or epitope by the cell and (ii) a sequence corresponding to a partition-specific barcode sequence in the second partition, whereby the barcoded nucleic acid molecule is indicative of no expression of the candidate antigen or epitope by the cell.

In any of the preceding embodiments, the method can comprise detecting the barcoded nucleic acid molecule indicative of no expression of the candidate antigen or epitope by the cell, whereas a barcoded nucleic acid molecule indicative of the binding between the antibody or antigen-binding fragment thereof and the candidate antigen or epitope of the cell in the second partition is not detected.

In any of the preceding embodiments, the plurality of partitions can further comprise a third partition comprising a cell having a decreased expression of the candidate antigen or epitope compared to the cell in the first partition, optionally wherein the cell is engineered to decrease expression of the candidate antigen or epitope.

In any of the preceding embodiments, the affinity of the antibody or antigen-binding fragment thereof binding to the cell in the third partition can be decreased, compared to the affinity of the antibody or antigen-binding fragment thereof binding to the cell in the first partition.

In any of the preceding embodiments, the cell in the third partition can comprise a third nucleic acid sequence indicative of decreased expression of the candidate antigen or epitope by the cell, optionally wherein the third nucleic acid sequence is or comprises a third expression status barcode.

In any of the preceding embodiments, a barcoded nucleic acid molecule can be generated in the third partition, wherein the barcoded nucleic acid molecule comprises (i) a sequence corresponding to the third nucleic acid sequence indicative of decreased expression of the candidate antigen or epitope by the cell and (ii) a sequence corresponding to a partition-specific barcode sequence in the third partition, whereby the barcoded nucleic acid molecule is indicative of decreased expression of the candidate antigen or epitope by the cell.

In any of the preceding embodiments, the method can comprise detecting the barcoded nucleic acid molecule indicative of decreased expression of the candidate antigen or epitope by the cell, whereas a barcoded nucleic acid molecule indicative of the binding between the antibody or antigen-binding fragment thereof and the candidate antigen or epitope of the cell in the third partition is not detected or is detected at a lower level and/or slower kinetics compared to that in the first partition.

In any of the preceding embodiments, the plurality of partitions can further comprise a fourth partition comprising a cell having an increased expression of the candidate antigen or epitope compared to the cell in the first partition, optionally wherein the cell is engineered to increase expression of the candidate antigen or epitope.

In any of the preceding embodiments, the affinity of the antibody or antigen-binding fragment thereof binding to the cell in the fourth partition can be increased, compared to the affinity of the antibody or antigen-binding fragment thereof binding to the cell in the first partition.

In any of the preceding embodiments, the cell in the fourth partition can comprise a fourth nucleic acid sequence indicative of increased expression of the candidate antigen or epitope by the cell, optionally wherein the fourth nucleic acid sequence is or comprises a fourth expression status barcode.

In any of the preceding embodiments, a barcoded nucleic acid molecule can be generated in the fourth partition, wherein the barcoded nucleic acid molecule comprises (i) a sequence corresponding to the fourth nucleic acid sequence indicative of increased expression of the candidate antigen or epitope by the cell and (ii) a sequence corresponding to a partition-specific barcode sequence in the fourth partition, whereby the barcoded nucleic acid molecule is indicative of increased expression of the candidate antigen or epitope by the cell.

In any of the preceding embodiments, the method can comprise detecting the barcoded nucleic acid molecule indicative of increased expression of the candidate antigen or epitope by the cell, whereas a barcoded nucleic acid molecule indicative of the binding between the antibody or antigen-binding fragment thereof and the candidate antigen or epitope of the cell in the fourth partition is detected at a higher level and/or faster kinetics compared to that in the first partition.

In any of the preceding embodiments, during or after the contacting, one or more cells bound by the antibody or antigen-binding fragment thereof can be enriched, purified, isolated, sorted, and/or separated (e.g., from one or more cells not bound by the antibody or antigen-binding fragment thereof), optionally wherein one or more cells not bound by the antibody or antigen-binding fragment thereof are enriched, purified, isolated, sorted, and/or separated (e.g., from one or more cells bound by the antibody or antigen-binding fragment thereof).

In any of the preceding embodiments, the one or more cells bound by the antibody or antigen-binding fragment thereof can be sorted or purified using a cytometer.

In any of the preceding embodiments, the antibody or antigen-binding fragment thereof can comprise a label attached thereto.

In any of the preceding embodiments, the label can comprise a fluorophore, and the one or more cells bound by the antibody or antigen-binding fragment thereof can be sorted or purified using fluorescence-activated cell sorting (FACS).

In any of the preceding embodiments, the one or more cells bound by the antibody or antigen-binding fragment thereof can be sorted or purified using magnetic-activated cell sorting (MACS), optionally wherein an antibody or antigen-binding fragment thereof that binds the label are used, and optionally wherein the label is a fluorophore.

In any of the preceding embodiments, the one or more cells bound by the antibody or antigen-binding fragment thereof can be captured on a support.

In any of the preceding embodiments, the method can further comprise eluting the one or more cells bound by the antibody or antigen-binding fragment thereof from the support.

In any of the preceding embodiments, the antibody or antigen-binding fragment thereof comprises a plurality of antibodies or antigen-binding fragments thereof.

In any of the preceding embodiments, the antibody or antigen-binding fragment thereof can comprise a first antibody or antigen-binding fragment thereof coupled to a first reporter oligonucleotide comprising a first antibody barcode sequence, and a second antibody or antigen-binding fragment thereof coupled to a second reporter oligonucleotide comprising a second antibody barcode sequence.

In any of the preceding embodiments, the first and second antibodies or antigen-binding fragments thereof can be the same or different.

In any of the preceding embodiments, the first and second antibodies or antigen-binding fragments thereof can bind to different antigens or epitopes.

In any of the preceding embodiments, the first and second antibodies or antigen-binding fragments thereof can bind to the same antigen or epitope.

In any of the preceding embodiments, the first and second antibody barcode sequences can be the same or different.

In any of the preceding embodiments, each of the plurality of antibodies or antigen-binding fragments thereof can be attached to a unique antibody barcode sequence.

In any of the preceding embodiments, the antibody or antigen-binding fragment thereof can be monoclonal.

In any of the preceding embodiments, the antibody or antigen-binding fragment thereof can be an IgG.

In any of the preceding embodiments, the antibody or antigen-binding fragment thereof can be expressed by a cell expressing the candidate antigen or epitope.

In any of the preceding embodiments, the antibody or antigen-binding fragment thereof can be secreted by the cell expressing the candidate antigen or epitope.

In any of the preceding embodiments, the antibody or antigen-binding fragment thereof can bind to the candidate antigen or epitope of the cell from which the antibody or antigen-binding fragment thereof is secreted.

In any of the preceding embodiments, the antibody or antigen-binding fragment thereof may not be coupled to the reporter oligonucleotide prior to secretion.

In any of the preceding embodiments, the antibody or antigen-binding fragment thereof can be coupled to the reporter oligonucleotide upon binding to the candidate antigen or epitope of the cell.

In any of the preceding embodiments, the coupling can be a cell surface coupling reaction.

In any of the preceding embodiments, the candidate antigen or epitope can be coupled to an enzyme catalyzing the cell surface coupling reaction.

In any of the preceding embodiments, the enzyme can be a sortase, e.g., a sortase A.

In any of the preceding embodiments, the antibody or antigen-binding fragment thereof can be coupled to a sortase recognition sequence, e.g., a peptide comprising an N-terminal LPXTG motif, while a barcode sequence to be conjugated to the antibody or antigen-binding fragment thereof comprises a sortase acceptor peptide (e.g., oligoglycine or oligoalanine). In any of the preceding embodiments, the antibody or antigen-binding fragment thereof can be coupled to a sortase acceptor peptide (e.g., oligoglycine or oligoalanine), while a barcode sequence to be conjugated to the antibody or antigen-binding fragment thereof comprises an N-terminal LPXTG motif.

In any of the preceding embodiments, the one or more of the barcoded nucleic acid molecules can be detected and/or analyzed by nucleic acid sequencing.

In any of the preceding embodiments, the method may not comprise optically imaging the antibody or antigen-binding fragment thereof, the antibody barcode sequence, the candidate antigen or epitope, the cell, the partition, the partition-specific barcode sequence, and/or the barcoded nucleic acid molecule.

In some embodiments, provided herein is a method of analyzing an antibody or antigen-binding fragment thereof, comprising: contacting an antibody or antigen-binding fragment thereof coupled to a reporter oligonucleotide comprising an antibody barcode sequence with a cell population comprising a first cell expressing a candidate antigen or epitope and a second cell not expressing the candidate antigen or epitope, (a) wherein the first cell comprises a first nucleic acid sequence indicating expression of the candidate antigen or epitope on or in the first cell, and the second cell comprises a second nucleic acid sequence indicating no expression of the candidate antigen or epitope on or in the second cell, (b) wherein cells of the population are partitioned into a plurality of partitions comprising (i) a first partition comprising the first cell and a first bead comprising a first bead barcode sequence and (ii) a second partition comprising the second cell and a second bead comprising a second bead barcode sequence, (c) wherein in the first partition, a barcoded nucleic acid molecule comprising (i) a sequence corresponding to the antibody barcode sequence and (ii) a sequence corresponding to the first bead barcode sequence is generated, and a barcoded nucleic acid molecule comprising (i) a sequence corresponding to the first nucleic acid sequence indicating expression of the candidate antigen or epitope on or in the first cell and (ii) a sequence corresponding to the first bead barcode sequence is generated, (d) wherein in the second partition, a barcoded nucleic acid molecule comprising (i) a sequence corresponding to the antibody barcode sequence and (ii) a sequence corresponding to the second bead barcode sequence is not generated, and a barcoded nucleic acid molecule comprising (i) a sequence corresponding to the second nucleic acid sequence indicating no expression of the candidate antigen or epitope on or in the second cell and (ii) a sequence corresponding to the second bead barcode sequence is generated, thereby analyzing binding between the antibody or antigen-binding fragment thereof and the candidate antigen or epitope.

In any of the preceding embodiments, all or a portion of one or more of the barcoded nucleic acid molecules can be detected and/or analyzed by nucleic acid sequencing.

In any of the preceding embodiments, the method may not comprise optically imaging the antibody or antigen-binding fragment thereof, the antibody barcode sequence, the candidate antigen or epitope, the first cell, the second cell, the first partition, the second partition, the first bead, the second bead, the first bead barcode sequence, the second bead barcode sequence, and/or one or more of the barcoded nucleic acid molecules.

In some embodiments, provided herein is a method of analyzing an antibody or antigen-binding fragment thereof, comprising: contacting an antibody or antigen-binding fragment thereof coupled to a reporter oligonucleotide comprising an antibody barcode sequence with a cell population comprising a first cell expressing a first level of a candidate antigen or epitope and a second cell expressing a second level of the candidate antigen or epitope, (a) wherein the first cell comprises a first nucleic acid sequence indicating the first level of expression of the candidate antigen or epitope on or in the first cell, and the second cell comprises a second nucleic acid sequence indicating the second level of expression of the candidate antigen or epitope on or in the second cell, (b) wherein cells of the population are partitioned into a plurality of partitions comprising (i) a first partition comprising the first cell and a first bead comprising a first bead barcode sequence and (ii) a second partition comprising the second cell and a second bead comprising a second bead barcode sequence, (c) wherein in the first partition, a barcoded nucleic acid molecule comprising (i) a sequence corresponding to the antibody barcode sequence and (ii) a sequence corresponding to the first bead barcode sequence is generated, and a barcoded nucleic acid molecule comprising (i) a sequence corresponding to the first nucleic acid sequence indicating the first level of expression of the candidate antigen or epitope on or in the first cell and (ii) a sequence corresponding to the first bead barcode sequence is generated, (d) wherein in the second partition, a barcoded nucleic acid molecule comprising (i) a sequence corresponding to the antibody barcode sequence and (ii) a sequence corresponding to the second bead barcode sequence is generated, and a barcoded nucleic acid molecule comprising (i) a sequence corresponding to the second nucleic acid sequence indicating the second level of expression of the candidate antigen or epitope on or in the second cell and (ii) a sequence corresponding to the second bead barcode sequence is generated, thereby analyzing binding between the antibody or antigen-binding fragment thereof and the candidate antigen or epitope.

In any of the preceding embodiments, all or a portion of one or more of the barcoded nucleic acid molecules can be detected and/or analyzed by nucleic acid sequencing.

In any of the preceding embodiments, the method may not comprise optically imaging the antibody or antigen-binding fragment thereof, the antibody barcode sequence, the candidate antigen or epitope, the first cell, the second cell, the first partition, the second partition, the first bead, the second bead, the first bead barcode sequence, the second bead barcode sequence, and/or one or more of the barcoded nucleic acid molecules.

In any of the preceding embodiments, the first level of expression can be higher than the second level of expression.

In some embodiments, provided herein is a method of analyzing an antibody or antigen-binding fragment thereof, comprising: partitioning a cell into a partition with a bead comprising a bead barcode sequence, (a) wherein the cell is engineered to secrete an antibody or antigen-binding fragment thereof and express a candidate antigen or epitope, and upon secretion of the antibody or antigen-binding fragment thereof from the cell and binding to the candidate antigen or epitope on the cell, the antibody or antigen-binding fragment thereof is coupled to a reporter oligonucleotide comprising an antibody barcode sequence, (b) wherein a barcoded nucleic acid molecule is generated in the partition, wherein the barcoded nucleic acid molecule comprises (i) a sequence corresponding to the antibody barcode sequence and (ii) a sequence corresponding to the bead barcode sequence, and (c) wherein the barcoded nucleic acid molecule is indicative of the binding between the antibody or antigen-binding fragment thereof and the candidate antigen or epitope of the cell.

In any of the preceding embodiments, the antibody or antigen-binding fragment thereof can be covalently coupled to the reporter oligonucleotide, e.g., via a sortase-catalyzed reaction.

In any of the preceding embodiments, the antibody or antigen-binding fragment thereof can be noncovalently coupled to the reporter oligonucleotide, optionally wherein the antibody or antigen-binding fragment thereof is bound by a secondary antibody comprising the reporter oligonucleotide.

BRIEF DESCRIPTION OF THE DRAWINGS

The drawings illustrate certain embodiments of the features and advantages of this disclosure. These embodiments are not intended to limit the scope of the appended claims in any manner.

DETAILED DESCRIPTION

Figure 1:
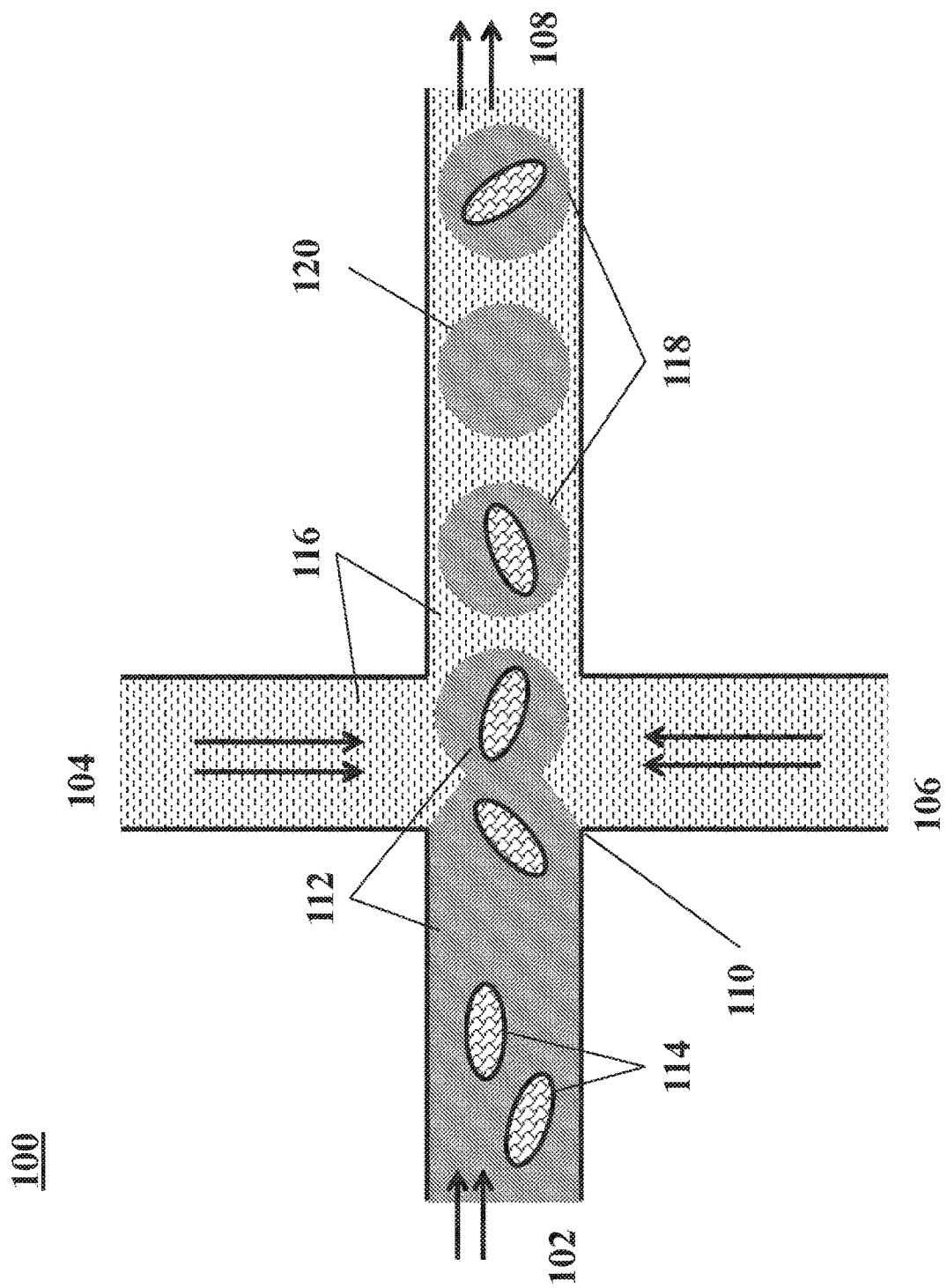
FIG. 1 shows an exemplary microfluidic channel structure for partitioning individual biological particles.

The practice of the techniques described herein may employ, unless otherwise indicated, conventional techniques and descriptions of organic chemistry, polymer technology, molecular biology (comprising recombinant techniques), cell biology, biochemistry, and sequencing technology, which are within the skill of those who practice in the art. Such conventional techniques comprise polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), DNA *Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), Molecular Cloning: A Laboratory Manual (all from Cold Spring Harbor Laboratory Press); Stryer, L. (1995) *Biochemistry* (4th Ed.) W. H. Freeman, New York N.Y.; Gait, *"Oligonucleotide Synthesis: A Practical Approach"* 1984, IRL Press, London; Nelson and Cox (2000), Lehninger, *Principles of Biochemistry* 3rd Ed., W. H. Freeman Pub., New York, N.Y.; and Berg et al. (2002) *Biochemistry*, $5^{th}$ Ed., W. H. Freeman Pub., New York, N.Y., all of which are herein incorporated in their entirety by reference for all purposes.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

In some embodiments, provided herein are methods comprising indexing a binding interaction to assess one or more binding attributes (e.g., antigen binding specificity and/or affinity to individual antigen receptors such as B cell receptors or antibodies), for example, using a hybrid microfluidics and sequencing-approach. In some aspects, provided herein are methods that enable the identification of binding candidates (e.g., antibody candidates to a target antigen or epitope), as well as the analysis of one or more binding attributes, such as binding specificity and/or affinity to one or more targets, of the identified binding candidates. In some embodiments, the analysis comprises the confirmation of a binding specificity and/or affinity of an antibody candidate to an antigen or epitope, comparing the binding specificity and/or affinity of various antibodies to one or more antigens or epitopes, comparing the binding specificity and/or affinity of various antigens or epitopes to one or more antibodies, and/or comparing the binding specificity and/or affinity or one or more reference values and/or that of one or more reference antibody/target binding pairs.

In some embodiments, the binding candidate identification and the analysis of one or more binding attributes are achieved in the same assay or assays, e.g., assays using the same readout such as a sequencing readout. In some embodiments, the binding candidate identification and the analysis of one or more binding attributes do not require different assay formats, such as identification using a readout based on nucleic acid hybridization or sequencing, and analysis using an immunoassay, such as a fluorescent sandwich immunoassay or ELISA, or using SPR. In some embodiments, the methods disclosed herein do not comprise performing an immunoassay, such as a fluorescent sandwich immunoassay or ELISA, or performing SPR. In some embodiments, the methods disclosed herein enable not only identification but also validation that an antibody does indeed bind an antigen or epitope, e.g., via multiple measurement modalities, as well as an assessment of one or more other binding attributes (such as binding affinity) of an antibody to an antigen or epitope.

In some embodiments, a label is attached to a binding molecule (e.g., a monoclonal antibody) of interest in order to assess one or more binding attributes (e.g., binding specificity and/or affinity) of the binding molecule to one or more binding partners. In some embodiments, the label comprises a reporter oligonucleotide comprising a reporter barcode sequence unique to the binding molecule. The attachment can be done directly or indirectly, e.g., via multiple chemical methods varying in their site specificity.

In some embodiments, the binding molecule (e.g., a monoclonal antibody) is engineered or fused to one or more moieties to enable the labeling. In the case of natively IgM or IgD or IgA antibody candidates, for example, the antibody candidate may be converted to an IgG format. In some embodiments, the labeling comprises attaching one or more oligonucleotide-conjugated fluorophores, directly or indirectly, to a binding molecule (e.g., a monoclonal antibody). In some embodiments, the labeling comprises conjugating an oligonucleotide (e.g., a reporter oligonucleotide comprising a reporter barcode sequence) or an oligonucleotide-conjugated fluorophore to biotin and then attaching the biotin-conjugated reporter to the binding molecule of interest via a biotinylation reaction. In some embodiments, a biotin-conjugated reporter oligonucleotide or reporter oligonucleotide-conjugated fluorophore can be attached to a streptavidin-tagged binding molecule.

In some embodiments, a population of cells expressing a binding partner (e.g., a target protein of interest, an antigen, or an epitope) are provided (e.g., engineered) and used in a method disclosed herein for assessing binding to a binding molecule (e.g., a monoclonal antibody). In some embodiments, a method disclosed herein comprises using one or both cell populations: a first population comprising cells that natively express a binding partner (e.g., a target protein of interest, an antigen, or an epitope), and a second population comprising cells that non-natively express the binding partner, e.g., via transfection or transduction. In some embodiments, a method disclosed herein comprises using a population of cells natively (e.g., without genetic or genomic modification or engineering) expressing a binding partner, and/or a population of cells engineered to express a binding partner, and/or cells engineered to express a higher level of the binding partner due to the engineering. In some embodiments, a method disclosed herein comprises using a population of cells that do not express a binding partner (e.g., a target protein of interest, an antigen, or an epitope). In some embodiments, a method disclosed herein comprises using a population of cells that natively do not express the binding partner. In some embodiments, a method disclosed herein comprises using a population of cells natively expressing the binding partner whose expression has been knocked down or knocked out. In some aspects, a combination of two or more, three or more, or all four single cell populations is used to assess cross-reactivity and/or false-positive binding between a binding molecule and a binding partner during analysis.

In some embodiments, for cells that natively express a binding partner, knockdown of the expression can be achieved by a labeled guide RNA (gRNA), such as a Perturb-seq guide. Methods of using barcode labeled guide RNA (e.g., a Perturb-seq guide) have been described, for example, in WO2018119447; WO2019157529; WO2018112423A; and Replogle et al. Combinatorial single-cell CRISPR screens by direct guide RNA capture and targeted sequencing. Nat Biotechnol 38, 954-961 (2020), which are herein incorporated by reference in their entirety. In some embodiments, a gRNA is coupled to a reporter oligonucleotide comprising a barcode sequence (e.g., a reporter barcode sequence). In some embodiments, the reporter oligonucleotide comprises a reporter capture handle comprising a capture sequence present on a nucleic acid barcode molecule comprising the partition-specific barcode sequence in a partition (e.g., a droplet or a microwell) disclosed herein.

In some embodiments, the guide is attached directly or indirectly to a molecule known to be internalized by cells, e.g., a cell that natively expresses or engineered to express a binding partner.

In some embodiments, a method disclosed herein comprises contacting a binding molecule (e.g., a monoclonal antibody) with one or more cell populations, e.g., sequentially or simultaneously, in any suitable order. For example, the one or more cell populations may include, in any suitable combination: cells expressing a binding partner (e.g., a target protein or peptide of interest, an antigen, or an epitope), cells modified (e.g., genetically engineered, such as using knockdown) to reduce or eliminate expression the binding partner, cells that do not express the binding partner, and cells not expressing the binding partner which also contain the modification to reduce or eliminate expression the binding partner. In some embodiments, the modification comprises knocking down expression of a target binding partner ("target") using a gRNA, such as one or more reporter-labeled gRNAs such as gRNAs labeled with reporter barcode sequences ("guide"), and the one or more cell populations comprise target+ cells, target+guide+ cells, target− cells, and/or target−guide+ cells. In some examples, molecules of a binding molecule (e.g., a mAb) are contacted with one or more target+ cells and one or more target+guide+ cells. In some examples, molecules of a binding molecule (e.g., a mAb) are contacted with one or more target+ cells and one or more target− cells. In some examples, molecules of a binding molecule (e.g., a mAb) are contacted with one or more target+ cells, one or more target+guide+ cells, and one or more target− cells. In some examples, molecules of a binding molecule (e.g., a mAb) are contacted with one or more target+ cells, one or more target+guide+ cells, one or more target− cells, and one or more target−guide+ cells.

In some embodiments, a method disclosed herein comprises enriching, purifying, and/or isolating cells, e.g., cells expressing a binding partner such as an antigen of interest, that are bound by a binding molecule (e.g., a monoclonal antibody). In some embodiments, a method disclosed herein comprises sorting for one or more cells that are bound by a binding molecule (e.g., a monoclonal antibody), and/or sorting out one or more cells that are not bound by the binding molecule. In some embodiments, a method disclosed herein comprises separating one or more cells that are bound by a binding molecule from one or more cells that are not bound by the binding molecule.

In some embodiments, the enriching, purifying, isolating, sorting, and/or separating comprises using a cytometer, e.g., for FACS, for example, by using a detectable label (e.g., a fluorophore) attached to the binding molecule (e.g., an mAb-attached fluorophore) and/or a detectable label (e.g., a fluorophore) attached to a binding partner. The fluorophore(s) may be used to identify binding between a binding molecule and a binding partner.

In some embodiments, the enriching, purifying, isolating, sorting, and/or separating comprises using a magnetic force, such as magnetic-activated cell sorting (MACS). For example, an mAb-attached fluorophore (e.g., in which the mAb is bound to a cell expressing an antigen for the mAb) may be retained or captured by a secondary antibody against the fluorophore or one or more other molecules used for enrichment, thereby retaining or capturing one or more cells bound by the mAb. In some embodiments, cells bound by an antibody, such as mAb-bound cells, may be eluted and optionally captured on a platform for single cell analysis. In some embodiments, cells bound by an antibody are put in a microfluidics system for single cell partitioning, including an emulsion droplet-based system such as the 10× Genomics Chromium™ system, such that an antibody-bound cell is encapsulated in a droplet.

In some embodiments, a method disclosed herein comprises performing single cell analysis of one or more cells expressing a binding partner (e.g., a target protein or peptide of interest, an antigen, or an epitope), one or more cells modified (e.g., genetically engineered, such as using knockdown) to reduce or eliminate expression the binding partner, one or more cells that do not express the binding partner, and/or one or more cells not expressing the binding partner which also contain the modification to reduce or eliminate expression the binding partner. In some embodiments, a method disclosed herein comprises detecting and/or analyzing one or more markers for each of the one or more cell populations. For example, one or more markers specific to each of the four populations (target+ cells, target+guide+ cells, target− cells, and target−guide+ cells) may be assayed to ensure equal or substantially equal representation of the cell populations for downstream analysis, e.g., by sequencing reads.

In some embodiments, provided herein are methods and compositions that enable epitope mapping of an antibody, and/or assessing whether an antibody such as a mAb can bind various sequences, such as variants and/or derivatives of a given antigen. For example, panels of guides (e.g., gRNAs) can be used to engineer variants of a target (e.g., engineering cells to express variants and/or derivatives of a given antigen) and to assess the binding of a monoclonal antibody to perform epitope mapping or to assess whether the mAb can bind one or more variants of the target.

In some embodiments, provided herein are methods and compositions that enable the use of engineered cells expressing an antibody or antigen binding fragment thereof (e.g., a monoclonal antibody) of interest and a target antigen (e.g., a peptide or protein) of interest. In some embodiments, an expression system for expressing an antibody or antigen binding fragment thereof is engineered into a cell, e.g., a cell of the B cell lineage, such as a plasma cell. In some embodiments, an expression system for expressing an antibody or antigen binding fragment thereof is introduced into the genome of a cell, e.g., by knocking the expression system in one or both alleles of a genetic locus of the cell's genome. In some embodiments, the antibody or antigen binding fragment thereof is in an IgG format, e.g., comprising an Fc of an IgG1, IgG2, IgG3 or IgG4 antibody. In some embodiments, the antibody or antigen binding fragment thereof comprises the $6^{th}$ exon of the IGHG1/2/3/4 constant region and the antibody or antigen binding fragment thereof is expressed and secreted from a B cell. In some embodiments, a method disclosed herein comprises expressing a target antigen of interest in the same cell that is engineered to express an antibody or antigen binding fragment thereof. An expression system for expressing the target may be engineered in to a cell, e.g., a cell of the B cell lineage. In some embodiments, the target is fused to a sortase, such as sortase A, and the antibody or antigen binding fragment thereof comprises a modified N terminal LPXTG motif, which upon secretion and binding of the antibody or antigen binding fragment to the target in the presence of a polyglycine-tagged reporter molecule (e.g., a reporter oligonucleotide), the binding molecule (e.g., antibody or antigen binding fragment) is tagged with the reporter molecule by the sortase catalyzed conjugation. In some embodiments, secretion of the antibody or antigen binding fragment leads to self-binding, where the secreted antibody or antigen binding fragment binds a target ligand on the same cell. The binding may be detected and/or analyzed using cell surface labelling (e.g., using sortase A catalyzed conjugation), and/or via a secondary antibody (e.g., a feature-barcoded anti-IgG monoclonal antibody) that binds the secreted antibody or antigen binding fragment. In some embodiments, a method disclosed herein comprises the use of cells engineered to have reduced expression of a target, e.g., B cells transduced with one or more PERTURB-Seq vectors to knock down expression of the target. In these cells, no or reduced target binding follows secretion of the antibody or antigen binding fragment thereof (e.g., an mAb), which may be used a control. In some embodiments, no or reduced reporter molecule labeling (e.g., labeling with a reporter barcode sequence) by the sortase catalyzed conjugation is observed in cells engineered to have reduced expression of the target.

II. Binding Molecules and Binding Partners

In some aspects, provided herein are methods and compositions that enable the analysis of a binding interaction between a binding molecule and a binding partner. In some embodiments, a method disclosed herein comprises contacting a binding molecule coupled to a first nucleic acid barcode sequence (e.g., a reporter barcode sequence) with a cell population comprising one or more cells expressing a candidate binding partner (e.g., a target protein of interest, an antigen, or an epitope), to allow binding between molecules of the binding molecule and the candidate binding partner expressed by the one or more cells.

In some embodiments, all or a subset of the cells of the population are partitioned into a plurality of partitions, wherein upon partitioning, a partition of the plurality of partitions comprises a cell of the population or subset thereof and a second nucleic acid barcode sequence (e.g., a common barcode sequence, e.g., a partition-specific barcode sequence) in the partition. In some embodiments, the cell in the partition is bound to one or more molecules of the binding molecule.

In some embodiments wherein the cell in the partition is bound to one or more molecules of the binding molecule, a barcoded nucleic acid molecule is generated in the partition, wherein the barcoded nucleic acid molecule comprises (i) a sequence corresponding to the first nucleic acid barcode sequence and (ii) a sequence corresponding to the second nucleic acid barcode sequence. The barcoded nucleic acid molecule may be analyzed to analyze the binding between the binding molecule and the candidate binding partner.

In some aspects, provided herein is a method of analyzing an antibody or antigen-binding fragment thereof, comprising: contacting an antibody or antigen-binding fragment thereof coupled to a first nucleic acid barcode sequence with a cell population comprising one or more cells expressing a candidate binding partner (e.g., a target protein or peptide of interest, an antigen, or an epitope), wherein all or a subset of the cells of the population are partitioned into a plurality of partitions, wherein upon partitioning, a partition of the plurality of partitions comprises a cell of the population or subset thereof and a second nucleic acid barcode sequence in the partition, wherein when the antibody or antigen-binding fragment thereof binds the candidate binding partner (e.g., a target protein or peptide of interest, an antigen, or an epitope), a barcoded nucleic acid molecule is generated in the partition, wherein the barcoded nucleic acid molecule comprises (i) a sequence corresponding to the first nucleic acid barcode sequence and (ii) a sequence corresponding to the second nucleic acid barcode sequence, and wherein the barcoded nucleic acid molecule is analyzed to analyze the binding between the antibody or antigen-binding fragment thereof and the candidate antigen or epitope.

In some aspects, a method provided herein further comprises analyzing an expression or presence status of the candidate binding partner (e.g., a candidate antigen or epitope) of the cell in a partition of the plurality of partitions. In some aspects, the cell population further comprises one or more cells that do not express the candidate binding partner, one or more cells engineered to express or to increase expression of the candidate binding partner, and/or one or more cells engineered to not express or to decrease expression of the candidate binding partner. In some embodiments, the plurality of partitions comprise a partition comprising a cell engineered or otherwise modified to express or to increase expression of the candidate binding partner. In some embodiments, the plurality of partitions comprise a partition comprising a cell engineered or otherwise modified to not express or to decrease expression of the candidate binding partner. In some embodiments, the plurality of partitions comprise a partition comprising a cell that does not express the candidate binding partner and that comprises a modification to eliminate or decrease expression of the candidate binding partner.

In some embodiments, a mammalian expression library can be used for epitope mapping. In some embodiments, a mammalian expression library can be generated by a lentiviral-mediated expression construct library, such that a plurality of cells each express a different epitope of the same antigen. In some embodiments, the epitopes can be linked to a membrane protein for cell surface expression.

In some aspects, a method provided herein further comprises contacting the antibody or antigen-binding fragment thereof coupled to a third nucleic acid barcode sequence with a further cell population comprising: (i) one or more cells that do not express the candidate binding partner binding partner (e.g., a target protein or peptide of interest, an antigen, or an epitope), (ii) one or more cells engineered to express or to increase expression of the candidate binding partner; and/or (iii) one or more cells engineered to not express or to decrease expression of the candidate binding partner, wherein the first and third nucleic acid barcode sequences are the same or different; partitioning all or a subset of the further cell population into a plurality of partitions, wherein upon partitioning, a partition of the plurality of partitions comprises a cell of the further cell population or subset thereof and a barcode bead having a fourth nucleic acid barcode sequence, wherein the second and fourth nucleic acid barcode sequences are the same or different, wherein when the antibody or antigen-binding fragment thereof binds the candidate binding partner, a further barcoded nucleic acid molecule is generated in the partition, wherein the further barcoded nucleic acid molecule comprises (i) a sequence corresponding to the third nucleic acid barcode sequence and (ii) a sequence corresponding to the fourth nucleic acid barcode sequence, and wherein the further barcoded nucleic acid molecule is analyzed to analyze the binding between the antibody or antigen-binding fragment thereof and the candidate binding partner.

A. Antigens and Antigen Binding Molecules

In some embodiments, an antigen binding molecule herein may include any molecule that specifically binds an antigenic determinant. Examples of antigen binding molecules are immunoglobulins and derivatives, e.g. fragments, thereof, and generally refer to a portion of a complete antibody (e.g., comprising each domain of the light and heavy chains respectively) capable of binding the same epitope/antigen as the complete antibody, albeit not necessarily to the same extent. Although multiple types of antigen binding molecules are possible, an antigen binding fragment typically comprises at least one pair of heavy and light chain variable regions (VH and VL, respectively) held together (e.g., by disulfide bonds) to preserve the antigen binding site and does not contain all or a portion of the Fc region. Antigen binding fragments of an antibody can be obtained from a given antibody by any suitable technique (e.g., recombinant DNA technology or enzymatic or chemical cleavage of a complete antibody), and typically can be screened for specificity in the same manner in which complete antibodies are screened. In some embodiments, an antigen binding fragment comprises an $F(ab')_2$ fragment, Fab' fragment, Fab fragment, Fd fragment, or Fv fragment. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific antigen binding ability to the polypeptide. In some embodiments, the antibody can be a monoclonal antibody (mAb), a recombinant bispecific monoclonal antibody such as a Bi-specific T-cell engager (BiTE), a simultaneous multiple interaction T-cell engaging (SMITE) bispecific antibody, or a bi-, tri-, or tetra-valent antibody.

In some embodiments, an antigen binding molecule herein may include an immunoglobulin molecule, e.g., a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called $\alpha$ (IgA), $\delta$ (IgD), $\epsilon$ (IgE), $\gamma$ (IgG), or $\mu$ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa ($\kappa$) and lambda ($\lambda$), based on the amino acid sequence of its constant domain. An immunoglobulin essentially consists of two Fab molecules and an Fc domain, linked via the immunoglobulin hinge region.

In some embodiments, an antigen binding molecule herein may include a BCR, which is composed of two genes IgH and IgK (or IgL) coding for antibody heavy and light chains. Immunoglobulins are formed by recombination among gene segments, sequence diversification at the junctions of these segments, and point mutations throughout the gene. Each heavy chain gene contains multiple copies of three different gene segments—a variable 'V' gene segment, a diversity 'D' gene segment, and a joining 'J' gene segment. Each light chain gene contains multiple copies of two different gene segments for the variable region of the protein—a variable 'V' gene segment and a joining 'J' gene segment. The recombination can generate a molecule with one of each of the V, D, and J segments. Furthermore, several bases may be deleted and others added (called N and P nucleotides) at each of the two junctions, thereby generating further diversity. After B cell activation, a process of affinity maturation through somatic hypermutation occurs. In this process progeny cells of the activated B cells accumulate distinct somatic mutations throughout the gene with higher mutation concentration in the CDR regions leading to the generation of antibodies with higher affinity to the antigens. In addition to somatic hypermutation activated B cells undergo the process of isotype switching. Antibodies with the same variable segments can have different forms (isotypes) depending on the constant segment. Whereas all naïve B cells express IgM (or IgD), activated B cells mostly express IgG but also IgM, IgA and IgE. This expression switching from IgM (and/or IgD) to IgG, IgA, or IgE occurs through a recombination event causing one cell to specialize in producing a specific isotype. A unique nucleotide sequence that arises during the gene arrangement process can similarly be referred to as a clonotype. In some embodiments, the antibody or antigen binding fragment thereof is in an IgG format, e.g., comprising an Fc of an IgG1, IgG2, IgG3 or IgG4 antibody. In some embodiments, the antibody or antigen binding fragment thereof comprises the $6^{th}$ exon of the IGHG1/2/3/4 constant region and the antibody or antigen binding fragment thereof is expressed and secreted from a B cell.

The antigens may include any antigen against which it is desired to test binding of an antigen binding molecule herein. In some embodiments, antigens are derived from bacteria, fungi, viruses, or allergens. In some embodiments, antigens are derived from internal sources, such as tumor cells or self-proteins (e.g. self-antigens). In some embodiments, the tumor antigen is in a tumor lysate. Self-antigens are antigens present on an organism's own cells. Self-antigens do not normally stimulate an immune response, but may in the context of autoimmune diseases, such as Type I Diabetes or Rheumatoid Arthritis, Multiple Sclerosis (and other demyelinating disorders). In some embodiments, the antigen is a neoantigen. Neoantigens are antigens that are absent from the normal human genome, but are created within oncogenic cells as a result of tumor-specific DNA modifications that result in the formation of novel protein sequences. Exemplary viral antigens include HIV antigens, Ebola antigen, HPV antigens, and EBV antigens, which are purified or delivered as a mixture, or delivered as killed or attenuated virus or virus fragments. In some embodiments, the HPV antigens are derived from the oncogenes E6 and E7 of HPV16. In some embodiments, the antigen is a non-protein antigen, such as a lipid, glycolipid, or polysaccharide.

For example, the antigens can include, but are not limited to, any antigens associated with a pathogen, including viral antigens, fungal antigens, bacterial antigens, helminth antigens, parasitic antigens, ectoparasite antigens, protozoan antigens, or antigens from any other infectious agent. Antigens can also include any antigens associated with a particular disease or condition, whether from pathogenic or cellular sources, including, but not limited to, cancer antigens, antigens associated with an autoimmune disease (e.g., diabetes antigens), allergy antigens (allergens), mammalian cell molecules harboring one or more mutated amino acids, proteins normally expressed pre- or neo-natally by mammalian cells, proteins whose expression is induced by insertion of an epidemiologic agent (e.g., virus), proteins whose expression is induced by gene translocation, and proteins whose expression is induced by mutation of regulatory sequences. These antigens can be native antigens or genetically engineered antigens which have been modified in some manner (e.g., sequence change or generation of a fusion protein). It will be appreciated that in some embodiments (e.g., when the antigen is expressed by the yeast vehicle from a recombinant nucleic acid molecule), the antigen can be a protein or any epitope of immunogenic domain thereof, a fusion protein, or a chimeric protein, rather than an entire cell or microorganism.

In some embodiments, the antigen is a carbohydrate antigen. For example, the epitope can be a cell-surface oligosaccharides (e.g., an oligosaccharide linked to a lipid or protein on the cell surface). In some embodiments, the carbohydrate antigen is a tumor antigen, such as the Lewis x and y antigens, their sialylated counterparts, or a gangliosides. Gangliosides are glycosphingolipids, which are ceramide-linked oligosaccharides with at least one terminal sialic acid residue.

Antigen or antibody specificity is a measure of an antibody's ability to bind uniquely to a specific antigen. In some cases, a particular epitope recognized by an antigen might appear on more than one protein antigen (cross-reactivity or low specificity). An antibody with high specificity would result in less cross-reactivity with different antigens. The specificity of an antibody for a target antigen can be assessed according to the methods provided herein by comparing antibody binding in cell populations expressing the target antigen with antibody binding to cell populations that do not express the target antigen. In comparison with specificity, affinity of an antibody is a measure of the strength of the binding between antibody and antigen, such that a low-affinity antibody binds weakly and high-affinity antibody binds firmly. The affinity of an antibody for a target antigen can be assessed according to the methods provided herein by varying the concentration of the antibody of interest or the expression level of the target antigen (e.g., using CRISPRi-seq, a variant of Perturb-seq, to allow transcriptional knockdown of the target antigen coupled to expression of a unique guide RNA barcode).

B. Enzymes and Enzyme Substrates

In some embodiments of the methods provided herein, the candidate epitope is or comprises a carbohydrate. In some embodiments of the methods provided herein, the candidate epitope comprising a carbohydrate can be enzymatically cleaved by a reporter oligonucleotide-labeled enzyme whose presence would be detected within the partition. Carbohydrate antigens can be polysaccharides and glycoconjugates of multiple structural configurations that are able to evoke carbohydrate-specific antibodies and react with these antibodies.

In some embodiments, the enzyme substrate is an N-glycan. In some embodiments, wherein the candidate epitope comprises part of the N-glycan. Suitable enzymes for removing N-glycans may include peptide-N-glycosidase F (PNGase F) or PNGase A, or an endo-β-N-acetylglucosaminidase. In some embodiments, an endo-β-N-acetylglucosaminidase has specificity for a particular type of N-glycan (e.g., high mannose, hybrid, complex biantennary, paucimannose, complex biantennary with core fucosylation). In some embodiments, the enzyme itself is the binding molecule of interest and the enzyme substrate is the binding partner. Thus, the methods provided herein can be used to determine occupancy or presence of an N-glycan at a specific site.

In some embodiments, the enzyme substrate is an O-glycan. Suitable enzymes for removing O-glycans include O-glycosidases such as a *Streptococcus pneumoniae* or *Enterococcus faecalis* O-glycosidase.

In some embodiments, the enzyme can be an exoglycosidase, a neuraminidase, a sialidase, a β galactosidase, a fucosidase, or a β N-acetylglucosaminidase.

Sialic acids comprise a large family of derivatives of neuraminic acid containing methyl, acetyl, sulfate and phosphate among other groups, which confer specific physicochemical properties (e.g., hydrophobicity, resistance to hydrolases) to the molecules carrying them.

In some embodiments, treatment with a sialidase may increase antibody binding by uncovering an epitope. In some embodiments, said epitope is a carbohydrate epitope (e.g., an O-glycosylated site capped with sialic acid).

In some embodiments, cleavage of the enzyme substrate by an enzyme is encoded using proximity-based labeling, such as sortase labeling of a peptide presenting the carbohydrate antigen with a nucleic acid barcode. In some embodiments, the enzyme can be operably linked to a sortase, and the peptide presenting the carbohydrate antigen can be tagged with a sortase acceptor sequence (e.g., an oligoglycine or oligoalanine). The cells expressing the candidate antigen or epitope can be incubated with the enzyme in the presence of an oligonucleotide barcode conjugated to a sortase recognition sequence (LPXTG). Binding of the enzyme to its substrate can thus result in labeling of the candidate epitope or antigen-presenting peptide with the oligonucleotide barcode conjugated to a sortase recognition sequence. The enzyme-modified cell populations encoding the presence or absence of an enzyme modification of the candidate antigen or epitope can be incubated with a barcode-labeled antibody or antigen-binding fragment. Following partitioning of cells, the presence of nucleic acid barcodes indicating (a) the enzyme modification, (b) binding of the antibody, and (c) the identity of the cell population can be identified by sequencing and analysis as described in section VII below. In any of the embodiments herein, the enzyme can be conjugated to an oligonucleotide barcode and the presence or absence of the barcoded enzyme can be detected in the partition. In any of the embodiments herein, the enzyme can be expressed by the cell that expresses the candidate antigen or epitope binding partner.

III. Cells and Cell Populations

In some embodiments, provided herein is a method of analyzing an antibody or antigen-binding fragment thereof, comprising: contacting an antibody or antigen-binding fragment thereof coupled to an antibody barcode sequence with a cell population comprising one or more cells natively expressing a candidate binding partner (e.g., B cells natively expressing a target antigen such as CD19), or cells that do not natively express a target. In some embodiments, cell populations that natively express a target antigen can be isolated or enriched based on selection for the target antigen or a label thereof. In some embodiments, cells natively expressing the target antigen can be isolated via mass cytometry (e.g., CyTOF), flow cytometry (e.g., FACS), or any other suitable labeling and enrichment method (see, section IV-A-2, Labels for Cells).

Any suitable cell population that does not natively express the candidate binding partner may be used. In some embodiments, the cell population that does not express the candidate antigen can be a cell line commonly used for expression of mammalian proteins by transient transfection or transduction, such as a HEK293, HT-1080, or CHO cell population. In some embodiments, the absence of native expression of the candidate binding partner can be confirmed, e.g., by RNA-seq or quantitative PCR.

In some embodiments, the cell is a primary cell or a cell line cell. In some embodiments, the cell is a blood cell. In some embodiments, the blood cell is an immune cell. In some embodiments, the immune cell is a lymphocyte. In some embodiments, the immune cell is a T cell, B cell, natural killer (NK) cell, dendritic cell (DC), NKT cell, mast cell, monocyte, macrophage, basophil, eosinophil, or neutrophil. In some embodiments, the immune cell is an adaptive immune cell such as a T cell and B cell. In some embodiments, the immune cell is an innate immune cell. Exemplary innate immune cells include innate lymphoid cells (ILC1, ILC2, ILC3), basophils, eosinophils, mast cells, NK cells, neutrophils, and monocytes. In some embodiments, the immune cell is a memory cell. In some embodiments, the immune cell is a primary human T cell. In some embodiments, the cell is a mouse, dog, cat, horse, rat, goat, monkey, or rabbit cell. In some embodiments, the cell is a human cell. In some embodiments, the cell is a non-mammalian cell. In some embodiments, the cell is a chicken, frog, insect, or nematode cell.

A. Genetic Engineering of Cells

In some embodiments, provided herein is a method of analyzing an antibody or antigen-binding fragment thereof, comprising: contacting an antibody or antigen-binding fragment thereof coupled to an antibody barcode sequence with one or more cell populations comprising engineered cells.

In some embodiments, the cell population to be engineered is a cell type commonly used for protein expression, such as yeast cell, a mammalian cell, e.g., Chinese hamster ovary (CHO) cells, baby hamster kidney (BHK) cells, NSO myeloma and Sp2/0 hybridoma mouse cell lines, human embryonic kidney cells 293 (HEK293) and HT-1080 human cells. Human cell lines used or developed for biopharmaceutical protein production include HEK293, PER.C6, CEVEC's amniocyte production (CAP), AGE1.HN, HKB-11 and HT-1080 cells. Several derivatives of HEK293 cells, such as HEK293-T and HEK293-EBNA1, have been developed from the parental HEK293 cells for improved recombinant protein production. Other nonhuman mammalian expression systems include the BHK-21 cells, murine NSO myeloma and Sp2/0 hybridoma cells.

In some embodiments, a cell population is engineered to express a target binding partner (e.g., a target protein or peptide of interest, a target antigen, or a target epitope). In some embodiments, the cell population is engineered to express the target binding partner via transient transfection or transduction, or via stable integration of an expression construct. In some embodiments, the expression construct can be delivered via any suitable vector (e.g., a plasmid vector or a viral vector such as an AAV vector or lentiviral vector).

In some embodiments, particularly for "difficult to transfect" cells such as T cells, an RNAi or guide RNA can be delivered via attachment to a molecule known to be internalized by the cell population of interest. There are multiple mechanisms by which small oligonucleotides (e.g. interfering RNAs) or their cationic complexes can internalize into mammalian cells. These include phagocytosis, pinocytosis, clathrin- and caveolin-dependent endocytosis. In particular, a type of endocytosis called "macropinocytosis" mediates non-selective uptake of tiny molecules, such as viruses, bacteria, nanoparticles, nutrients and antigens. Macropinocytosis is initiated from cell surface membrane ruffles that fold back onto themselves forming heterogeneous-sized endocytic structures known as macropinosomes. In some embodiments, the short oligonucleotide can be internalized into a cell population (e.g., T-cells) through a macropinocytosis-like endocytic mechanism e.g. in the absence of transfection reagents or electroporation. Methods for engineering "difficult to transfect" cells such as T cells have been described, for example, in Roth, T. L., Puig-Saus, C., Yu, R. et al. Reprogramming human T cell function and specificity with non-viral genome targeting. *Nature* 559, 405-409 (2018); which is herein incorporated by reference in its entirety.

In some embodiments, an expression construct for a target binding partner can be engineered in to a cell using any suitable method. In some embodiments, an engineered cell line can be generated using a CRISPR/Cas system using a guide RNA and a homology donor cassette comprising the expression construct.

In some embodiments, an engineered cell line can be a cell line engineered to stably express a Cas nuclease (e.g., Cas9).

In some embodiments, an engineered cell population comprises a knock-down or knockout (KO) cell line. In some embodiments, the gene knocked down or knocked out encodes a target binding partner, or a candidate binding partner. In some embodiments, gene knock down can be achieved using siRNA or a CRISPRi system. In some embodiments, KO cell lines are generated via CRISPR-Cas9 and certified via Sanger sequencing. This type of KO cell line provides a complete loss-of-function phenotype from a single allele KO and eliminates any masking of the knockout from a second allele seen in diploid cell models. In some embodiments, the CRISPR-Cas9 system can be used for knocking out gene expression in vivo or in vitro by using a combination of an sgRNA (single guide RNA) along with Cas9 (dCas9) nuclease. In some embodiments, the CRISPR guide RNA and/or Cas9 expression constructs can be delivered via a lentiviral-based CRISPR system. Expression of the sgRNA and Cas9 are stable and can be used in dividing or non-dividing cells or whole model organisms. Lentiviruses are powerful tools for manipulating host cells because they allow stable genomic integration of engineered DNA in both dividing and non-dividing cells, multiply or in single copy.

In certain aspects, the cells can be engineered by delivering a compound or composition into a cell. In some embodiments, the compound is a single compound. In some embodiments, the compound is a mixture of compounds. In some embodiments, the compound comprises a nucleic acid. In some embodiments, the compound is a nucleic acid. Exemplary nucleic acids include, without limitation, recombinant nucleic acids, DNA, recombinant DNA, cDNA, genomic DNA, RNA, siRNA, mRNA, saRNA, miRNA, lncRNA, tRNA, and shRNA. In some embodiments, the nucleic acid is homologous to a nucleic acid in the cell. In some embodiments, the nucleic acid is heterologous to a nucleic acid in the cell. In some embodiments, the compound is a plasmid. In some embodiments, the compound comprises a protein or polypeptide. In some embodiments, the nucleic acid is a transposon. A transposon, or transposable element, is a DNA segment that inserts itself into another position within the genome.

In some embodiments, the compound is a protein or polypeptide. In some embodiments, the protein or polypeptide is a therapeutic protein, antibody, fusion protein, antigen, synthetic protein, reporter marker, or selectable marker. In some embodiments, the protein is a gene-editing protein or nuclease such as a zinc-finger nuclease (ZFN), transcription activator-like effector nuclease (TALEN), mega nuclease, or CRE recombinase.

a. Perturb-Seq

In some embodiments, provided herein is a method of analyzing the binding epitope of an antibody or antigen-binding fragment of interest, wherein the method comprises analyzing binding of the antibody or antigen-binding fragment of interest to one or more cells are engineered or otherwise modified to express the candidate epitope. In some embodiments, engineering of the cell populations comprises knocking down or knocking out a polynucleotide encoding, or controlling or regulating expression of, the candidate epitope. In some embodiments, the engineering comprises a CRISPR-mediated perturbation, such as CRISPR/Cas induced mutations, or CRISPR-based transcriptional interference (CRISPRi), which mediates gene inactivation with high efficacy and specificity (Qi et al, 2013; Gilbert et al., 2014; Horlbeck et al, 2016).

In some embodiments, engineering of the cell populations comprises introducing CRISPR-mediated perturbations combined with a cell barcoding strategy that encodes the identity of the CRISPR-mediated perturbation in an expressed transcript, such as using "Perturb-seq." Methods of using barcode labeled guide RNA (e.g., a Perturb-seq guide) have been described, for example, in WO2018119447; WO2019157529; WO2018112423A; and Replogle et al. Combinatorial single-cell CRISPR screens by direct guide RNA capture and targeted sequencing. Nat Biotechnol 38, 954-961 (2020); which are herein incorporated by reference in their entirety. The identity of the perturbation is encoded on an expressed guide barcode for each guide RNA. In some embodiments, the barcode sequences associated with each sgRNA are randomly assigned and unique. In some embodiments, the barcode sequences associated with each sgRNA are assigned by sequencing during library construction.

In some embodiments, a cell population can be infected with a pool of lentiviral constructs that encode sgRNAs and their associated barcodes. In some embodiments, the pool of lentiviral constructs comprises a library of barcoded guide vectors, e.g., vectors comprising a sgRNA targeting a candidate epitope. A library can comprise, at least 2 or more vectors. For example, a library can comprise at least 2, 3, 4, 5, 6, 7, 8, 9, 10, 20, 30, 40, 50, 60, 70, 80, 90, 100, 200, 300, 400, 500, 600, 700, 800, 900, 1000, 2000, 3,000, 4,000, 5,000, 6,000, 7,000, 8,000, 9,000, 10,000 or more dual guide-vectors.

In the methods provided herein, a site-directed nuclease is expressed in the mammalian cells. In some examples, the mammalian cells stably express a site-directed nuclease. In some examples, the site-directed nuclease is constitutively expressed. In some examples, the site-directed nuclease is under the control of an inducible promoter. In some examples, the mammalian cells are infected with a vector comprising a polynucleotide sequence encoding the site-directed nuclease prior to or subsequent to infecting the cells with the plurality of vectors. In any of the methods described herein, the site-directed nuclease can be transiently or stably expressed in the mammalian cells. In some examples, the site-directed nuclease is encoded by an expression cassette in the cell, the expression cassette comprising a promoter operably linked to a polynucleotide encoding the site-directed nuclease. In some examples, the promoter operably linked to the polynucleotide encoding the site-directed nuclease is a constitutive promoter. In other examples, the promoter operably linked to the polynucleotide encoding the site-directed nuclease is inducible. For example, and not to be limiting, the site-directed nuclease can be under the control of a tetracycline inducible promoter, a tissue-specific promoter, or an IPTG-inducible promoter.

The methods described can be used with any site-directed nuclease that requires a constant region of an sgRNA for function. These include, but are not limited to RNA-guided site-directed nucleases. Examples include nucleases present in any bacterial species that encodes a Type II CRISPR/Cas system. For example, and not to be limiting, the site-directed nuclease can be a Cas9 polypeptide, a C2c2 polypeptide or a Cpf1 polypeptide. In some examples, the site-directed nuclease is the site-directed nuclease is an enzymatically active site-directed nuclease, such as, for example, a Cas9 polypeptide. In some examples, the site-directed nuclease is a deactivated site-directed nuclease, for example, a dCas9 polypeptide.

In the methods provided herein, once the cells have been infected, the cells are cultured for a sufficient amount of time to allow sgRNA: site-directed nuclease complex formation and transcriptional modulation, such that a pool of cells expressing a detectable phenotype (e.g., binding or absence of binding to the antibody or antigen-binding fragment of interest) can be selected from the plurality of infected cells.

In some embodiments, the method comprises expressing a site-directed nuclease in the mammalian cells; exposing the cells to the antibody or antigen-binding fragment of interest, and separating a selected pool of cells that bind to the antibody or antigen-binding fragment of interest from the plurality of cells infected by the barcoded sgRNA library; and analyzing the sequences of the sgRNA barcode and the antibody or antigen-binding fragment barcode.

B. Fixed Samples

In some embodiments, the engineered cell populations described herein may be subjected to conditions that allow reporter-barcoded antibody molecules or antigen binding fragments thereof to couple to intracellular molecules or analytes, such as intracellular antigens or epitopes. Such conditions may comprise fixation and permeabilization. Fixation of cells or constituents of cells may comprise application of a chemical species or chemical stimulus. The term "fixed" as used herein with regard to biological samples generally refers to the state of being preserved from decay and/or degradation. "Fixation" generally refers to a process that results in a fixed sample, and in some instances can include contacting the biomolecules within a cell population with a fixative (or fixation reagent) for some amount of time, whereby the fixative results in covalent bonding interactions such as crosslinks between biomolecules in the cells. A "fixed cell population" may generally refer to a cell population that has been contacted with a fixation reagent or fixative. For example, a formaldehyde-fixed cell population has been contacted with the fixation reagent formaldehyde. Generally, fixed cells from a fixed cell population refer to cells that have been in contact with a fixative under conditions sufficient to allow or result in the formation of intra- and inter-molecular covalent crosslinks between biomolecules within the cell(s). Generally, contact of a cell with a fixation reagent (e.g., paraformaldehyde or PFA) results in the formation of intra- and inter-molecular covalent cross-links between biomolecules within the cells(s). In some cases, provision of the fixation reagent, such as formaldehyde, may result in covalent aminal crosslinks within RNA, DNA, and/or protein molecules. For example, the widely used fixative reagent, paraformaldehyde or PFA, fixes tissue samples by catalyzing crosslink formation between basic amino acids in proteins, such as lysine and glutamine. Both intra-molecular and inter-molecular crosslinks can form in the protein. These crosslinks can preserve protein secondary structure and also eliminate enzymatic activity in the preserved tissue sample. Examples of fixation reagents include but are not limited to aldehyde fixatives (e.g., formaldehyde, also commonly referred to as "paraformaldehyde," "PFA," and "formalin"; glutaraldehyde; etc.), imidoesters, NHS (N-Hydroxysuccinimide) esters, and the like.

In some embodiments, the fixative or fixation reagent useful in the methods of the present disclosure is formaldehyde. The term "formaldehyde" when used in the context of a fixative also refers "paraformaldehyde" (or "PFA") and "formalin", both of which are terms with specific meanings related to the formaldehyde composition (e.g., formalin is a mixture of formaldehyde and methanol). Thus, a formaldehyde-fixed biological sample may also be referred to as formalin-fixed or PFA-fixed. Protocols and methods for the use of formaldehyde as a fixation reagent to prepare fixed biological samples are well known in the art, and can be used in the methods and compositions of the present disclosure. For example, suitable ranges of formaldehyde concentrations for use in preparing a fixed cell population is 0.1 to 10%, 1-8%, 1-4%, 1-2%, 3-5%, or 3.5-4.5%. In some embodiments of the present disclosure the cells are fixed using a final concentration of 1% formaldehyde, 4% formaldehyde, or 10% formaldehyde. Typically, the formaldehyde is diluted from a more concentrated stock solution—e.g., a 35%, 25%, 15%, 10%, 5% PFA stock solution.

It is contemplated that more than one fixation reagent can be used in combination in preparing a fixed cell population. For example, in some cases the cell populations are contacted with a fixation reagent containing both formaldehyde and glutaraldehyde, and thus the contacted biomolecules can include fixation crosslinks resulting both from formaldehyde induced fixation and glutaraldehyde induced fixation. Typically, a suitable concentration of glutaraldehyde for use as a fixation reagent is 0.1 to 1%.

The engineered cell populations may be permeabilized prior to, simultaneously with, or after treatment with a fixative. Cells may be permeabilized to provide access to a plurality of intracellular molecules included therein. Intracellular molecules or analytes from different parts of a cell and/or a specific sub-cellular region can be targeted with permeabilization reagents. For example, permeabilization reagents can be selected to increase the accessibility (e.g., by a reporter-barcoded antibody molecule such as a monoclonal antibody) to analytes from the cytosol, from cell nuclei, from mitochondria, from microsomes, and more generally, from any other compartment, organelle, or portion of a cell. Permeabilizing agents that specifically target certain cell compartments and organelles can be used to selectively target analytes from cells for analysis. Permeabilization may involve partially or completely dissolving or disrupting a cell membrane or a portion thereof. Permeabilization may be achieved by, for example, contacting a cell membrane with an organic solvent or a detergent such as saponin, Triton X-100™, Tween-20™, or sodium dodecyl sulfate (SDS). Other suitable agents for this purpose include, but are not limited to, organic solvents (e.g., acetone, ethanol, and methanol), cross-linking agents (e.g., paraformaldehyde), and enzymes (e.g., trypsin, proteases (e.g., proteinase K). See, e.g., U.S. Pub. No. 20200277663, herein incorporated by reference in its entirety).

Upon binding by antibody molecules or antigen fragments thereof to intracellular molecules in engineered cells that have been fixed and optionally permeabilized, the engineered cells may be further processed as described herein, e.g., enrichment, coupling of a reporter molecule, partitioned for single cell analysis, etc.

IV. Labels

A. Nucleic Acid Labels and Barcodes
1. Labels for Binding Molecules

In some aspects of the methods provided herein, a binding molecule (e.g., an antibody or antigen binding fragment) is labeled with a detectable label. A detectable label is a moiety that has at least one element, isotope, or functional group incorporated into the moiety which enables detection of the molecule, e.g., a protein or peptide, or other entity, to which the label is attached. Labels can be directly attached (e.g., via a bond) or can be attached by a linker (such as, for example, an optionally substituted alkylene; an optionally substituted alkenylene; an optionally substituted alkynylene; an optionally substituted heteroalkylene; an optionally substituted heteroalkenylene; an optionally substituted heteroalkynylene; an optionally substituted arylene; an optionally substituted heteroarylene; an optionally substituted acylene, or any combination thereof, which can make up a linker). It will be appreciated that the label may be attached to or incorporated into a molecule, for example, a protein, polypeptide, or other entity, at any position. In general, a detectable label can fall into any one (or more) different classes of labels: a) a label which contains isotopic moieties, which may be radioactive or heavy isotopes, including, but not limited to, 2H, 3H, 13C, 14C, 15N, 18F, 31P, 32P, 35S, 67Ga, 76Br, 99mTc (Tc-99m), 111In, 123I, 125I, 131I, 153Gd, 169Yb, and 186Re; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label fluorescein-isothiocyanate (FITC); d) a label which has one or more photo affinity moieties; e) a label which is a ligand for one or more known binding partners (e.g., biotin-streptavidin, FK506-FKBP), and f) a nucleic acid label that can be detected via sequencing. In certain embodiments, a label comprises a radioactive isotope, preferably an isotope which emits detectable particles, such as particles. In certain embodiments, the label comprises a fluorescent moiety. In certain embodiments, the label is a fluorescent label such as PE, APC, or fluorescein-isothiocyanate (FITC). In certain embodiments, the label comprises a ligand moiety with one or more known binding partners. In certain embodiments, the label comprises biotin. In some embodiments, a label is a fluorescent polypeptide (e.g., GFP or a derivative thereof such as enhanced GFP (EGFP)) or a luciferase (e.g., a firefly, Renilla, or Gaussia luciferase). It will be appreciated that, in certain embodiments, a label may react with a suitable substrate (e.g., a luciferin) to generate a detectable signal. Non-limiting examples of fluorescent proteins include GFP and derivatives thereof, proteins comprising fluorophores that emit light of different colors such as red, yellow, and cyan fluorescent proteins. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See, e.g., Chalfie, M. and Kain, S R (eds.) Green fluorescent protein: properties, applications, and protocols Methods of biochemical analysis, v. 47 Wiley-Interscience, Hoboken, N.J., 2006; and Chudakov, D M, et al., Physiol Rev. 90(3):1103-63, 2010, for discussion of GFP and numerous other fluorescent or luminescent proteins. In some embodiments, a label comprises a dark quencher, e.g., a substance that absorbs excitation energy from a fluorophore and dissipates the energy as heat.

In some embodiments, the binding molecule (e.g., antibody or antigen binding fragment) is labeled with a barcode sequence. In some embodiments, generation of an antibody-oligonucleotide conjugate involves site-directed conjugation methods, where the oligonucleotide is conjugated to either n-linked glycans or internally-expressed protein tags. Non-site directed conjugation approaches are mostly used to build up larger libraries of oligonucleotide-conjugated antibodies. Several suitable bioorthogonal conjugation methods have been established, where the most common are based on maleimide, tetrazine, or click chemistry reagents. Conjugation is also possible via a reactive thiol (sulfhydryl) group. Antibodies contain oxidized sulfhydryl (—SH) groups present as disulfide (S—S) bridges, which contribute to the tertiary structure of the antibody. These disulfide bridges can be reduced to expose their reactive groups by a reducing agent (e.g., 2-ME/SDS). Antibodies can be selectively cleaved to create either two half antibody molecules or smaller antibody fragments such as F(ab'). Conjugation using the 'hinge' region free/reduced —SH group can orient the attached oligonucleotide away from the antigen-binding regions, hence preventing steric hindrance and preserving activity.

In some embodiments, the nucleic acid barcode sequences can include from 6 to about 20 or more nucleotides within the sequence of the oligonucleotides. In some cases, the length of a barcode sequence may be 6, 7, 8, 9, 10, 11, 12, 13, 14, 15, 16, 17, 18, 19, 20 nucleotides or longer. In some cases, the length of a barcode sequence may be at least 6, 7, 8, 9, 10, 11, 12, 13, 14, 15, 16, 17, 18, 19, 20 nucleotides or longer. In some cases, the length of a barcode sequence may be at most 6, 7, 8, 9, 10, 11, 12, 13, 14, 15, 16, 17, 18, 19, 20 nucleotides or shorter. These nucleotides may be completely contiguous, e.g., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be 4, 5, 6, 7, 8, 9, 10, 11, 12, 13, 14, 15, 16 nucleotides or longer. In some cases, the barcode subsequence may be at least 4, 5, 6, 7, 8, 9, 10, 11, 12, 13, 14, 15, 16 nucleotides or longer. In some cases, the barcode subsequence may be at most 4, 5, 6, 7, 8, 9, 10, 11, 12, 13, 14, 15, 16 nucleotides or shorter. The binding molecule can also comprise other functional sequences useful in the processing of the nucleic acids from the co-partitioned cells. These sequences include, e.g., targeted or random/universal amplification primer sequences for amplifying the genomic DNA from the individual cells within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences.

2. Labels for Cells

In one aspect of the methods provided herein, the one or more cells in a cell population comprise a detectable marker indicative of expression of the candidate, e.g., target, binding partner (e.g., an antigen or epitope) by the one or more cells. In some embodiments, the detectable marker comprises a nucleic acid sequence (e.g., an oligonucleotide barcode). In some embodiments, the nucleic acid sequence is conjugated to a polynucleotide, a polypeptide, a lipid, a carbohydrate, a small molecule, or one or more other organic or inorganic molecules, or any combination, complex, or conjugate thereof.

In some embodiments, a cell is engineered to express a target binding partner via lentiviral transduction or temporary transfection, in addition to a fluorescent (e.g., GFP/BFP/RFP/YFP) or other surface marker (e.g., CD45). In some embodiments, the marker expression construct (e.g., the fluorescent marker or surface marker) can be fused to a nucleotide sequence that is efficiently captured by beads during the detection and analysis step described herein in section VI to ensure adequate detection/prevent dropout.

In some embodiments, cells that either natively or non-natively express a target binding partner can be incubated with a guide RNA construct coupled to a nucleic acid barcode sequence (e.g., using Perturb-seq) to knock down or reduce expression of the target binding partner. In some embodiments, the presence of the barcode associated with the guide RNA indicates absence of target binding partner expression.

Any of these cell populations could be individually stained with a unique feature-barcoded antibody (hashtagging) or lipid. Methods of cell hashing or hashtagging are known, see, e.g., Stoeckius et al., "Cell "hashing" with barcoded antibodies enables multiplexing and doublet detection for single cell genomics," Genome Biology volume 19, Article number: 224 (2018), incorporated herein by reference in its entirety. In addition, each of these populations could be further selected by magnetic or microfluidic enrichment by targeting that antibody or lipid.

Each of these populations could be further selected or enriched by targeting a marker. Example markers for labeling cells include canonical/ubiquitous markers such as CD298, CD45 (lymphocytes), fluorescent markers, B cell (CD19) or other cell-type specific markers such as CD19, CD20, CD45, or CD22.

In some embodiments, cells may be labeled using a binding molecule (e.g., an antibody) that binds to a cell surface marker specifically expressed by the cell population. In some embodiments, the antibody targeting the cell surface marker is fused to a detectable label as described above (e.g., a fluorescent label or a nucleic acid barcode sequence). In some embodiments, cells can be labeled using an antibody targeting a cell surface marker of the cell population of interest, wherein the antibody label is fused to a unique barcode.

B. Cell Surface Labelling of Binding Molecules

In some embodiments of the methods provided herein, a cell surface protein can be labeled at the cell surface using proximity-based labeling with an oligonucleotide barcode (e.g., nucleic acid barcode sequence). In some embodiments, proximity-based labeling can be used to detect binding of a binding molecule (e.g., an antibody or antigen binding fragment) to an antigen or target epitope. In some examples, a cell population expressing target antigens or epitopes can be engineered to express a secreted antibody of interest, and self-binding of the secreted antibody to the target binding partner can be detected via sortase-mediated attachment of a nucleic acid barcode sequence (e.g., oligonucleotide barcode) to the target binding partner.

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide. For example, the first plurality of the labeling agent and second plurality of the labeling agent may interact with different cells, cell populations or samples, allowing a particular reporter oligonucleotide to indicate a particular cell population (or cell or sample) and cell feature. In this way, different samples or groups can be independently processed and subsequently combined together for pooled analysis (e.g., partition-based barcoding as described elsewhere herein). See, e.g., U.S. Pat. Pub. 20190323088, which is hereby entirely incorporated by reference for all purposes.

1. Proximity-Based Labeling of a Secreted Antibody

In some embodiments, provided herein is a method of analyzing an antibody or antigen-binding fragment thereof, comprising: partitioning a cell into a partition with a barcode bead, wherein the cell is engineered to secrete an antibody or antigen-binding fragment thereof and express a candidate epitope, and upon secretion of the antibody or antigen-binding fragment thereof from the cell and binding to the candidate epitope, the antibody or antigen-binding fragment thereof is directly or indirectly coupled to a first nucleic acid barcode sequence, wherein the barcode bead comprises a second nucleic acid barcode sequence, wherein when the antibody or antigen-binding fragment thereof specifically binds the candidate epitope, a barcoded nucleic acid molecule is generated in the partition, wherein the barcoded nucleic acid molecule comprises (i) a sequence corresponding to the first nucleic acid barcode sequence and (ii) a sequence corresponding to the second nucleic acid barcode sequence, and wherein the barcoded nucleic acid molecule is analyzed to analyze the binding between the antibody or antigen-binding fragment thereof and the candidate epitope. Methods of labeling a target protein upon binding with a binding partner protein have been described. See, e.g., Pasqual et al. "Monitoring T cell-dendritic cell interactions in vivo by intercellular enzymatic labelling." Nature vol. 553,7689 (2018): 496-500, which describes the Labelling Immune Partnerships by SorTagging Intercellular Contacts (LIPSTIC) method.

a. Sortase Labeling

In some embodiments, the binding molecule (e.g., antibody or antigen-binding fragment thereof) is covalently coupled to the first nucleic acid barcode sequence, e.g., via an isopeptide reaction such as a sortase-catalyzed ligation. The protein comprising the candidate binding partner (e.g., an antigen or epitope) can be fused to a sortase, e.g., a sortase capable of transferring its substrate onto a sortase acceptor peptide fused to the antibody or antigen-binding fragment of interest. Suitable sortases, sortase substrates (which comprise a sortase recognition sequence), and sortase acceptor peptides have been described, for example, in U.S. Pat. No. 10,053,683, herein incorporated by reference in its entirety. Selection of suitable combinations of the three components has been described.

Suitable sortases can include a sortase A, a sortase B, a sortase C, or a sortase D. In some embodiments, the sortase is a mutant SrtA that exhibits improved catalytic activity as compared to the wild-type counterpart. In some examples, the sortase is fused to the N-terminus of the member of the ligand-receptor pair. In other examples, the sortase is fused to the C-terminus of the member of the ligand-receptor pair.

In some embodiments, the antibody or antigen-binding fragment of interest is fused to a sortase acceptor peptide via methods known in the art, e.g., recombinant technology. A sortase acceptor peptide can be any peptide that provides a nucleophilic acyl group for accepting a sortase substrate (a peptide comprising a sortase recognition sequence as described herein). Such an acceptor peptide may contain up to about 50 amino acids, such as up to 40, 30, 20, 15, 10, or 5 amino acids. In some embodiments, the acceptor peptide is an oligoglycine or oligoalanine, such as a 1-5 glycine fragment or a 1-5 alanine fragment. In some examples, the oligoglycine consists of 3 or 5 glycine residues. In other examples, the oligoalanine consists of 3 or 5 alanine residues. In some embodiments, the sortase acceptor peptide is fused to the amino-terminal end of the antibody or antigen-binding fragment of interest.

The sortase substrate used in the methods described herein, which is conjugated to a detectable label comprising a first nucleic acid barcode sequence, can comprise any sortase recognition sequence as known in the art or disclosed herein. Selection of a suitable sortase recognition sequence would depend on the type of sortase used in the same methods. Suitable sortase recognition sequences include LPXTG, in which X is any amino acid residue. In some embodiments, the sortase recognition sequence is LPETG, which may be co-used with a mutant SrtA described above.

A plurality of cells engineered such that the cells secrete an antibody or antigen-binding fragment thereof and each cell expresses a candidate epitope can be incubated in the presence of a suitable sortase substrate, which is associated with a detectable label under conditions allowing for occurrence of the transpeptidation reaction catalyzed by the sortase to conjugate the labeled sortase substrate to the sortase acceptor peptide. The detectable label includes a first nucleic acid barcode sequence, such that wherein when the antibody or antigen-binding fragment thereof specifically binds the candidate epitope, the sortase conjugates the first nucleic acid barcode sequence to the sortase acceptor peptide fused to the antibody or antigen-binding fragment of interest.

If the secreted antibody or antigen-binding fragment binds to the candidate epitope expressed by the engineered cell, the spatial proximity would allow the sortase fused to the candidate epitope to transfer the labeled sortase substrate onto the sortase acceptor peptide on antibody or antigen-binding fragment, thereby labeling the antibody or antigen-binding fragment with the first nucleic acid barcode sequence.

The binding activities of the thus identified polypeptides can be confirmed by a conventional binding assay, e.g., ELISA assay.

In some embodiments, the labeling system described herein can be applied to identify intercellular binding contacts, such as between a population of antibody-expressing cells (e.g., B cells or T cells) and a population of cells expressing a candidate epitope. Cells conjugated to the detectable label can then be isolated via a routine method, e.g., by cell sorting. The labeled cells thus identified can be further analyzed to identify the cell-surface antibody and binding partner based on the nucleic acid barcode label.

In some embodiments, the cells can be separated into partitions with a barcode bead, wherein when the antibody or antigen-binding fragment thereof specifically binds the candidate epitope, a barcoded nucleic acid molecule is generated in the partition, wherein the barcoded nucleic acid molecule comprises (i) a sequence corresponding to the first nucleic acid barcode sequence and (ii) a sequence corresponding to the second nucleic acid barcode sequence of the barcode bead, and wherein the dually barcoded nucleic acid molecule is analyzed to analyze the binding between the antibody or antigen-binding fragment thereof and the candidate epitope.

b. Other Isopeptide Reactions

In some embodiments, a reporter barcode labeled binding molecule (e.g., antibody or antigen-binding fragment thereof) is covalently coupled to a binding partner (e.g., an antigen or epitope) via a spontaneous isopeptide reaction between peptide tags. Proteins that are capable of spontaneous isopeptide bond formation have been used to develop peptide tag/binding partner pairs which covalently bind to each other and which hence provide irreversible interactions (see e.g. WO2011/098772 herein incorporated by reference). In some embodiments, the binding molecule (e.g., barcode labeled antibody) is labeled with a peptide tag and the binding partner (e.g. antigen) is labeled with a binding partner for the peptide tag, wherein the peptide tag and binding partner of the peptide tag are capable of spontaneous isopeptide bond formation, such that binding of the binding molecule and binding partner results in formation of an isopeptide bond between the two. The isopeptide bond formed by the peptide tag and binding partner pairs can be stable under conditions where non-covalent interactions would rapidly dissociate, e.g. over long periods of time (e.g. weeks), at high temperature (to at least 95° C.), at high force, or with harsh chemical treatment (e.g. pH 2-11, organic solvent, detergents or denaturants). Thus, cells expressing a secreted binding molecule that binds to an antigen, e.g., binding, partner expressed on the cell surface will be labeled by the binding molecule and its attached reporter molecule (e.g., reporter oligonucleotide).

In brief, a peptide tag/binding partner pair may be derived from any protein capable of spontaneously forming an isopeptide bond (an isopeptide protein), wherein the domains of the protein are expressed separately to produce a peptide tag that comprises one of the residues involved in the isopeptide bond (e.g. a lysine) and a peptide binding partner that comprises the other residue involved in the isopeptide bond (e.g. an asparagine or aspartate). In some instances, one of the peptide tag or binding partner comprises one or more other residues required to form the isopeptide bond (e.g. a glutamate).

In some embodiments, the domains comprising the residues involved in isopeptide bond formation can be expressed separately, i.e. as three separate peptides (domains, modules or units). In this respect, the peptide tag comprises one of the residues involved in the isopeptide bond (e.g. a lysine), the peptide binding partner that comprises the other residue involved in the isopeptide bond (e.g. an asparagine or aspartate) and a third peptide comprises the one or more other residues involved in isopeptide bond formation but not involved in the isopeptide bond itself (e.g. a glutamate). Mixing all three peptides results in the formation of an isopeptide bond between the two peptides comprising the residues that react to form the isopeptide bond, i.e. the peptide tag and binding partner. Thus, the third peptide mediates the conjugation of the peptide tag and binding partner but does not form of the part resultant structure, i.e. the third peptide is not covalently linked to the peptide tag or binding partner. As such, the third peptide may be viewed as a protein ligase or peptide ligase. This is particularly useful as it minimises the size of the peptide tag and binding partner that need to be fused to the protein of interest, thereby reducing the possibility of unwanted interactions caused by the addition of the peptide tag or binding partner, e.g. misfolding.

Various proteins which are capable of spontaneously forming one or more isopeptide bonds (a so-called "isopeptide protein") have been identified (e.g., SpyTag/SpyCatcher or SnoopTag/SnoopCatcher and may be modified to produce a peptide tag/binding partner pair and optionally a peptide ligase (e.g., SpyLigase or SnoopLigase), as discussed above. Further proteins that are capable of spontaneously forming one or more isopeptide bonds may be identified by comparing their structures with those of proteins which are known to spontaneously form one or more isopeptide bonds. Particularly, other proteins which may spontaneously form an isopeptide bond may be identified by comparing their crystal structures with those from known isopeptide proteins e.g. the major pilin protein Spy0128, and in particular comparing the Lys-Asn/Asp-Glu/Asp residues often involved in the formation of an isopeptide protein. Additionally, other isopeptide proteins may be identified by screening for structural homologues of known isopeptide proteins using the Protein Data Bank using standard database searching tools. The SPASM server may be used to target the 3D structural template of Lys-Asn/Asp-Glu/Asp of the isopeptide bond or isopeptide proteins may also be identified by sequence homology alone. A peptide tag and binding partner, SpyTag and SpyCatcher that react spontaneously to form an isopeptide bond, and a three part SpyTag/KTag/SpyLigase have been developed previously (WO2011/098772 and U.S. Pub. No. 20200115422; herein incorporated by reference in their entirety). Orthogonal systems such as SnoopTag/SnoopCatcher or SnoopTagJr, DogTag, and SnoopLigase have also been described (see e.g. U.S. patent Ser. No. 10/526,379 and U.S. Pub. No. 20200115422, herein incorporated by reference in their entirety).

C. Click Chemistry

As used herein, the term "click chemistry," generally refers to reactions that are modular, wide in scope, give high yields, generate only inoffensive byproducts, such as those that can be removed by nonchromatographic methods, and are stereospecific (but not necessarily enantioselective). See, e.g., U.S. Pat. Pub. 2019/0100632 (now U.S. Pat. No. 10,590,244), U.S. Pat. Pub. 2019/0233878, and Angew. Chem. Int. Ed., 2001, 40(11):2004-2021, which are entirely incorporated herein by reference for all purposes.

In some cases, click chemistry can describe pairs of functional groups that can selectively react with each other in mild, aqueous conditions. An example of click chemistry reaction can be the Huisgen 1,3-dipolar cycloaddition of an azide and an alkynes, i.e., Copper-catalyzed reaction of an azide with an alkyne to form a 5-membered heteroatom ring called 1,2,3-triazole. The reaction can also be known as a Cu(I)-Catalyzed Azide-Alkyne Cycloaddition (CuAAC), a Cu(I) click chemistry or a $Cu^+$ click chemistry. Catalyst for the click chemistry can be Cu(I) salts, or Cu(I) salts made in situ by reducing Cu(II) reagent to Cu(I) reagent with a reducing reagent (Pharm Res. 2008, 25(10): 2216-2230). Known Cu(II) reagents for the click chemistry can include, but are not limited to, Cu(II)-(TBTA) complex and Cu(II) (THPTA) complex. TBTA, which is tris-[(1-benzyl-1H-1,2, 3-triazol-4-yl)methyl]amine, also known as tris-(benzyltriazolylmethyl)amine, can be a stabilizing ligand for Cu(I) salts. THPTA, which is tris-(hydroxypropyltriazolylmethyl) amine, can be another example of stabilizing agent for Cu(I). Other conditions can also be accomplished to construct the 1,2,3-triazole ring from an azide and an alkyne using copper-free click chemistry, such as by the Strain-promoted Azide-Alkyne Click chemistry reaction (SPAAC, see, e.g., Chem. Commun., 2011, 47:6257-6259 and Nature, 2015, 519 (7544):486-90), each of which is entirely incorporated herein by reference for all purposes.

In some cases, the present disclosure also contemplates the use of click chemistry reactions resulting in chemical linkages that are not a 1,2,3-triazole. See, e.g., U.S. Pat. Pub. 2019/0233878, which is incorporated by reference in its entirety. A range of such click chemistry reactions useful for preparing biocompatible gels are well-known in the art. See e.g., Madl and Heilshorn, "Bioorthogonal Strategies for Engineering Extracellular Matrices," Adv. Funct. Mater. 2018, 28: 1706046, which is hereby incorporated by reference herein.

An example of a click chemistry reaction useful in the compositions and methods of the present disclosure that is copper-free and does not result in a 1,2,3-triazole linkage is an Inverse-electron demand Diels-Alder (IED-DA) reaction. (See e.g., Madl and Heilshorn 2018.) As described elsewhere herein, in the IED-DA click chemistry reaction, the pair of click chemistry functional groups comprises a tetrazine group and a trans-cyclooctene (TCO) group, or a tetrazine group and a norbonene group. This reaction is copper free and results in a linkage comprising a dihydropyridazine group rather than a 1,2,3-triazole.

Other specific biorthogonal click chemistry reactions that are useful in the compositions and methods of the present disclosure, but which result in a chemical linkage other than a 1,2,3-triazole include a Diels-Alder reaction between a pair of furan and maleimide functional groups, a Staudinger ligation, and nitrile oxide cycloaddition. These click chemistry reactions and others are well-known in the art and described in e.g., Madl and Heilshorn 2018. Accordingly, in some embodiments the copper-free click chemistry useful in forming crosslinked polymers of the present disclosure can be selected from: (a) strain-promoted azide/dibenzocyclooctyne-amine (DBCO) click chemistry; (b) inverse electron demand Diels-Alder (IED-DA) tetrazine/trans-cyclooctene (TCO) click chemistry; (c) inverse electron demand Diels-Alder (IED-DA) tetrazine/norbonene click chemistry; (d) Diels-Alder maleimide/furan click-chemistry; (e) Staudinger ligation; and (f) nitrile-oxide/norbonene cycloaddition click chemistry.

V. Cells Bound by Binding Molecules

Cells bound by binding molecules can then be detected and/or separated by mechanisms that allow the differentiation of the bound cells from non-bound cells. Exemplary methods include, but are not limited to, fluorescent-activated cell sorting (FACS), magnetic-activated cell sorting (MACS) or buoyancy-activated cell sorting (BACS).

In some embodiments, one or more markers specific to each population (e.g., target+ cells, target+guide+ cells, target− cells, and target−guide+ cells) may be assayed to ensure equal or substantially equal representation of the cell populations for downstream analysis.

In some embodiments, the cells bound by binding molecules or cells of one or more populations (e.g., target+ cells, target+guide+ cells, target− cells, and target−guide+ cells) can be detected and/or selected by using fluorescent-activated cell sorting (FACS). In some embodiments, cells bound by binding molecules can be detected by a fluorochrome-labeled antibody recognizing the cell-bound binding molecules, and subsequently analyzed using FACS. In some embodiments, cells bound by binding molecules can be detected by an antibody (e.g., a fluorochrome-labeled antibody, a magnetic bead-labeled antibody, a microbubble-labeled antibody, or a combination thereof) recognizing a tag or target of the cell-bound antibodies, and subsequently analyzed.

In some embodiments, the cells bound by binding molecules or cells of one or more populations (e.g., target+ cells, target+guide+ cells, target− cells, and target−guide+ cells) can be detected and/or selected by using magnetic-activated cell sorting (MACS). In some embodiments, cells bound by binding molecules can be detected by a magnetic bead-labeled antibody recognizing the cell-bound antibodies, and subsequently analyzed using MACS. In some embodiments, cells bound by binding molecules can be detected by an antibody (e.g., a fluorochrome-labeled antibody, a magnetic bead-labeled antibody, a microbubble-labeled antibody, or a combination thereof) recognizing a tag or target of the cell-bound antibodies, and subsequently analyzed.

In some embodiments, the cells bound by binding molecules or cells of one or more populations (e.g., target+ cells, target+guide+ cells, target− cells, and target−guide+ cells) can be detected and/or selected by using buoyancy-activated cell sorting (BACS). In some embodiments, cells bound by binding molecules can be detected by a microbubble-labeled antibody recognizing the cell-bound antibodies. In some embodiments, cells bound by binding molecules can be bound by a microbubble-labeled antibody, resulting in lower density in a buoyancy separation. In some embodiments, cells bound by binding molecules can be detected by a microbubble-labeled antibody recognizing the Fc region of the cell-bound antibodies, and subsequently analyzed using BACS. In some embodiments, cells bound by binding molecules can be detected by an antibody (e.g., a fluorochrome-labeled antibody, a magnetic bead-labeled antibody, a microbubble-labeled antibody, or a combination thereof) recognizing a tag or target of the cell-bound antibodies, and subsequently analyzed.

In some embodiments wherein the detectable label for each cell population comprises a detectable nucleotide sequence (e.g., an oligonucleotide barcode), the different cell populations need not be separated prior to partitioning and sequencing analysis. Multiple cell populations can be combined and processed in parallel as one single sample via cellular barcoding, allowing detection of the cell population label in each single cell partition. Following data acquisition, individual cells can be unmixed in silico and reassigned back to their initial samples via their unique barcode.

VI. Cell Processing and Partitioning

In one aspect, the methods and system described herein provide for the compartmentalization, depositing or partitioning of individual cells (e.g., cells bound by binding molecules or cells of one or more populations, e.g., target+ cells, target+guide+ cells, target− cells, and target−guide+ cells, after contacting with an antibody such as a monoclonal antibody) from a sample material containing cells, into discrete compartments or partitions (referred to interchangeably herein as partitions), where each partition maintains separation of its own contents from the contents of other partitions. In one aspect, the methods described herein comprise the compartmentalization, depositing or partitioning of nucleic acid molecules (e.g., genomic DNA and/or nucleic acid barcodes directly or indirectly attached to the cell surface) of one or more individual cells from a sample material containing cells, into discrete partitions, where each partition maintains separation of its own contents from the contents of other partitions.

In another aspect, the methods and system described herein provide for the compartmentalization, depositing or partitioning of individual cells from a sample material containing cells after at least one labelling agent or reporter agent has been bound to a cell surface feature of a cell, into discrete partitions, where each partition maintains separation of its own contents from the contents of other partitions. Identifiers including unique identifiers and common or universal tags, e.g., barcodes, may be previously, subsequently or concurrently delivered to the partitions that hold the compartmentalized or partitioned cells, in order to allow for the later attribution of the characteristics of the individual cells to one or more particular compartments. Further, identifiers including unique identifiers and common or universal tags, e.g., barcodes, may be coupled to labelling agents and previously, subsequently or concurrently delivered to the partitions that hold the compartmentalized or partitioned cells, in order to allow for the later attribution of the characteristics of the individual cells to one or more particular compartments. Identifiers including unique identifiers and common or universal tags, e.g., barcodes, may be delivered, for example on an oligonucleotide, to a partition via any suitable mechanism.

In some embodiments, a partition herein includes a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

A. Systems and Methods for Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. In some examples, the partitioned particle is a labelled cell of B-cell lineage, e.g. a plasma cell, which secretes an antibody. In other examples, the partitioned particle may be a labelled cell engineered to secrete antibodies. The partition can be a droplet in an emulsion. A partition may comprise one or more other partitions.

A partition may include one or more particles. A partition may include one or more types of particles. For example, a partition of the present disclosure may comprise one or more biological particles, and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle, and/or one or more of its macromolecular constituents, e.g., a secreted antibody or antigen binding fragment thereof, encased inside of a gel or polymer matrix (e.g., via a capture agent coupled to both the matrix and said secreted antibody or antigen binding fragment thereof), such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials (e.g., secreted analytes, i.e., secreted antibodies or antigen binding fragments thereof) within its matrix (e.g., via a capture agent configured to couple to both the matrix and said secreted antibody or antigen binding fragment thereof). The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may, in one non-limiting example, be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell, or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (e.g., cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle, such as one B cell or plasma cell) and multiply occupied droplets (having more than one biological particle, such as multiple B cells or plasma cells). As described elsewhere herein, in some cases, the majority of occupied partitions can include no more than one biological particle, per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles, such as B cells or plasma cells, (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
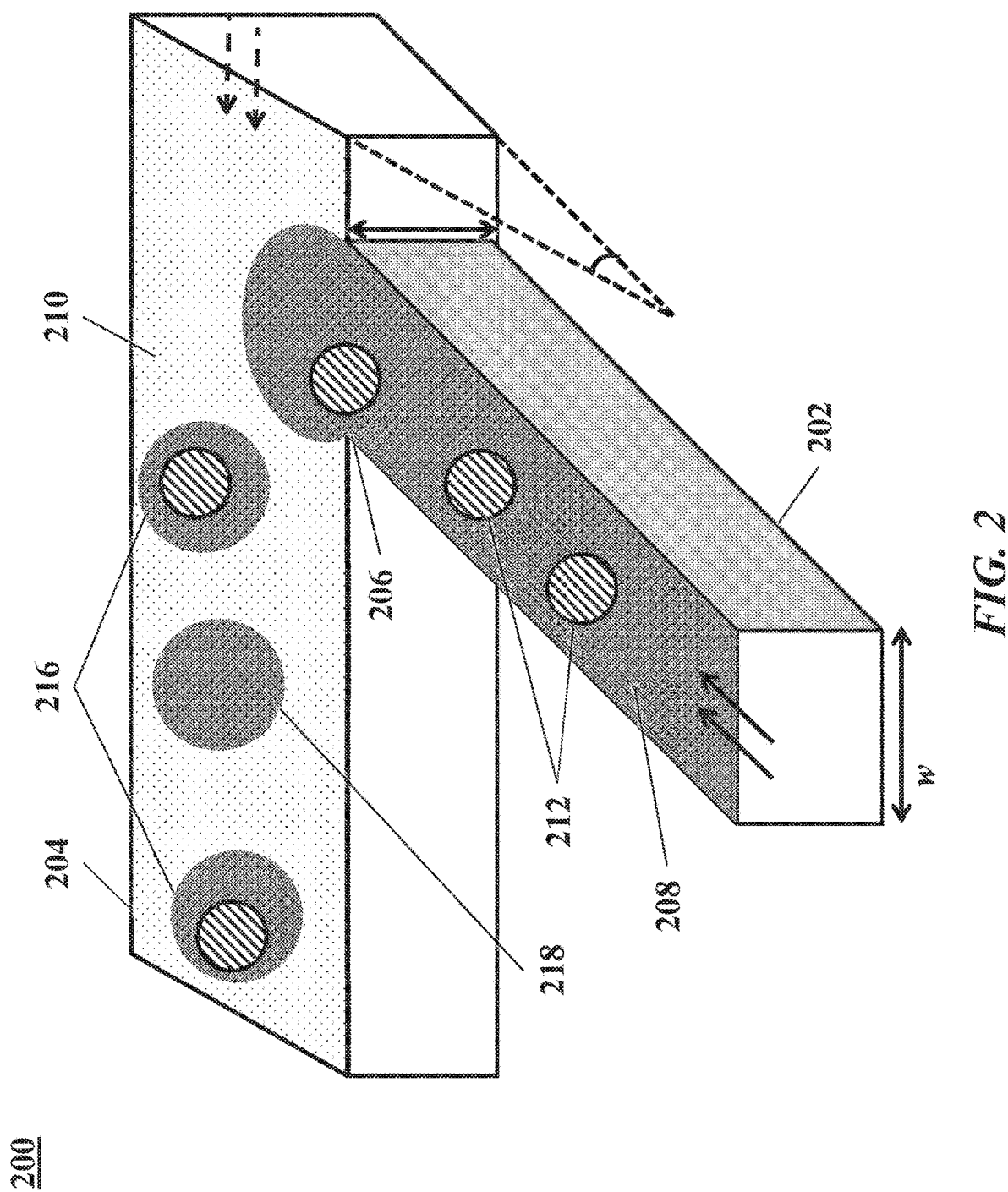
FIG. 2 shows an exemplary microfluidic channel structure for the controlled partitioning of beads into discrete droplets.

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides) (described in relation to FIGS. 1 and 2). For avoidance of doubt, a barcoded nucleic acid molecule in the context of "microcapsules or beads . . . carrying barcoded nucleic acid molecules" refers to a nucleic acid molecule where the nucleic acid molecule includes a barcode sequence; see, e.g., FIG. 3 referencing 301 and FIG. 11 referencing 1110 in combination with 1112. The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles, may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or a combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles (e.g., B cells or plasma cells) as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles, or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle, can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents (e.g., secreted antibodies or antigen binding fragments thereof) of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized (e.g., coupled to a capture agent) to bind to targeted analytes (e.g., secreted antibodies or antigen binding fragment thereof), such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles or macromolecular constituents (e.g., RNA, DNA, proteins, secreted antibodies or antigen binding fragments thereof etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles.

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli (e.g., cytokines, antigens, etc.). In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

FIG. 2 shows an example of a microfluidic channel structure for the controlled partitioning of beads into discrete droplets. A channel structure 200 can include a channel segment 202 communicating at a channel junction 206 (or intersection) with a reservoir 204. The reservoir 204 can be a chamber. Any reference to "reservoir," as used herein, can also refer to a "chamber." In operation, an aqueous fluid 208 that includes suspended beads 212 may be transported along the channel segment 202 into the junction 206 to meet a second fluid 210 that is immiscible with the aqueous fluid 208 in the reservoir 204 to create droplets 216, 218 of the aqueous fluid 208 flowing into the reservoir 204. At the junction 206 where the aqueous fluid 208 and the second fluid 210 meet, droplets can form based on factors such as the hydrodynamic forces at the junction 206, flow rates of the two fluids 208, 210, fluid properties, and certain geometric parameters (e.g., w, h0, α, etc.) of the channel structure 200. A plurality of droplets can be collected in the reservoir 204 by continuously injecting the aqueous fluid 208 from the channel segment 202 through the junction 206.

In some instances, the aqueous fluid 208 can have a substantially uniform concentration or frequency of beads 212. The beads 212 can be introduced into the channel segment 202 from a separate channel (not shown in FIG. 2). The frequency of beads 212 in the channel segment 202 may be controlled by controlling the frequency in which the beads 212 are introduced into the channel segment 202 and/or the relative flow rates of the fluids in the channel segment 202 and the separate channel. In some instances, the beads can be introduced into the channel segment 202 from a plurality of different channels, and the frequency controlled accordingly.

In some instances, the aqueous fluid 208 in the channel segment 202 can comprise biological particles. In some instances, the aqueous fluid 208 can have a substantially uniform concentration or frequency of biological particles. As with the beads, the biological particles can be introduced into the channel segment 202 from a separate channel. The frequency or concentration of the biological particles in the aqueous fluid 208 in the channel segment 202 may be controlled by controlling the frequency in which the biological particles are introduced into the channel segment 202 and/or the relative flow rates of the fluids in the channel segment 202 and the separate channel. In some instances, the biological particles can be introduced into the channel segment 202 from a plurality of different channels, and the frequency controlled accordingly. In some instances, a first separate channel can introduce beads and a second separate channel can introduce biological particles into the channel segment 202. The first separate channel introducing the beads may be upstream or downstream of the second separate channel introducing the biological particles.

The second fluid 210 can comprise an oil, such as a fluorinated oil, that includes a fluorosurfactant for stabilizing the resulting droplets, for example, inhibiting subsequent coalescence of the resulting droplets.

In some instances, the second fluid 210 may not be subjected to and/or directed to any flow in or out of the reservoir 204. For example, the second fluid 210 may be substantially stationary in the reservoir 204. In some instances, the second fluid 210 may be subjected to flow within the reservoir 204, but not in or out of the reservoir 204, such as via application of pressure to the reservoir 204 and/or as affected by the incoming flow of the aqueous fluid 208 at the junction 206. Alternatively, the second fluid 210 may be subjected and/or directed to flow in or out of the reservoir 204. For example, the reservoir 204 can be a channel directing the second fluid 210 from upstream to downstream, transporting the generated droplets.

Systems and methods for controlled partitioning are described further in PCT/US2018/047551, which is hereby incorporated by reference in its entirety.

Figure 15:
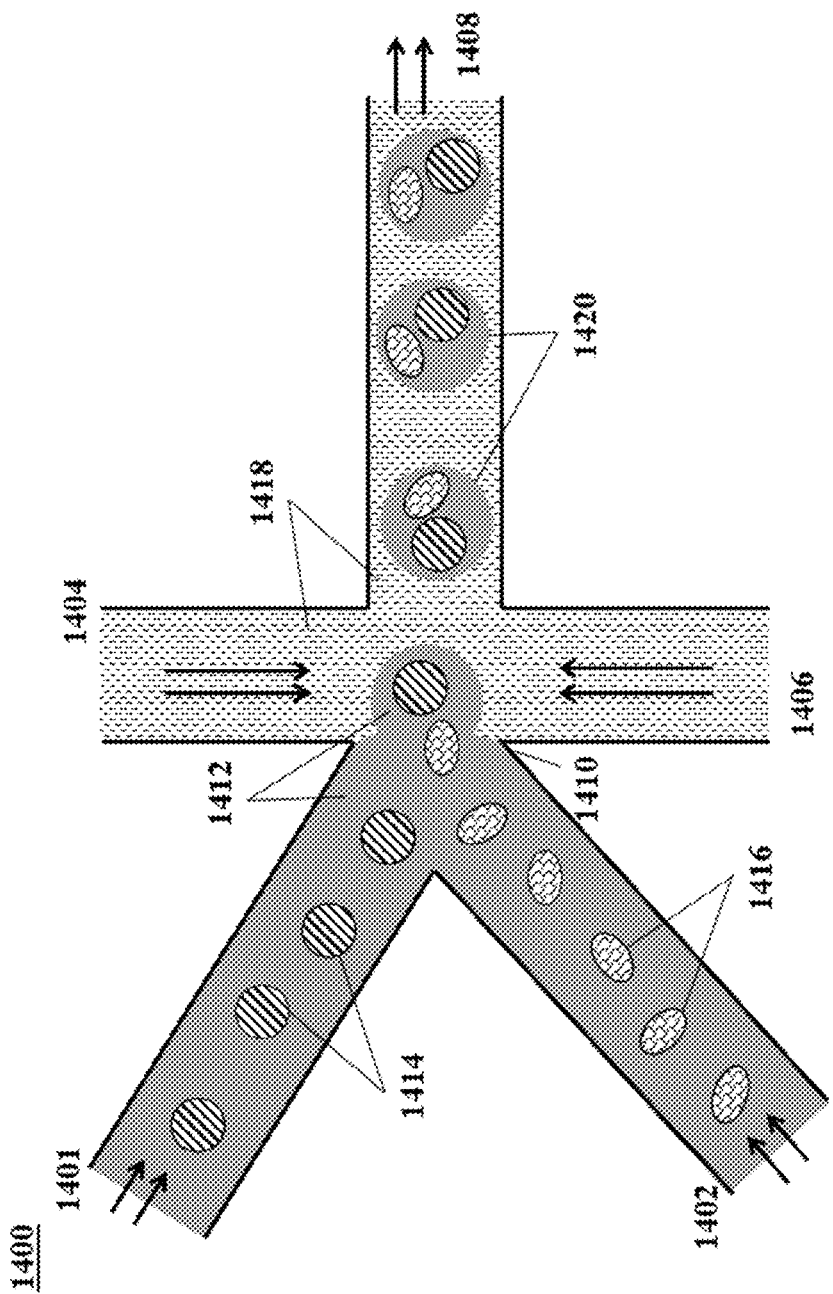
FIG. 15 shows an exemplary microfluidic channel structure for delivering barcode carrying beads to droplets.

FIG. 15 shows an example of a microfluidic channel structure 1400 for delivering barcode carrying beads to droplets. The channel structure 1400 can include channel segments 1401, 1402, 1404, 1406 and 1408 communicating at a channel junction 1410. In operation, the channel segment 1401 may transport an aqueous fluid 1412 that includes a plurality of beads 1414 (e.g., with nucleic acid molecules, e.g., nucleic acid barcode molecules or barcoded oligonucleotides, molecular tags) along the channel segment 1401 into junction 1410. The plurality of beads 1414 may be sourced from a suspension of beads. For example, the channel segment 1401 may be connected to a reservoir comprising an aqueous suspension of beads 1414. The channel segment 1402 may transport the aqueous fluid 1412 that includes a plurality of biological particles 1416 along the channel segment 1402 into junction 1410. The plurality of biological particles 1416 may be sourced from a suspension of biological particles. For example, the channel segment 1402 may be connected to a reservoir comprising an aqueous suspension of biological particles 1416. In some instances, the aqueous fluid 1412 in either the first channel segment 1401 or the second channel segment 1402, or in both segments, can include one or more reagents, as further described below. A second fluid 1418 that is immiscible with the aqueous fluid 1412 (e.g., oil) can be delivered to the junction 1410 from each of channel segments 1404 and 1406. Upon meeting of the aqueous fluid 1412 from each of channel segments 1401 and 1402 and the second fluid 1418 from each of channel segments 1404 and 1406 at the channel junction 1410, the aqueous fluid 1412 can be partitioned as discrete droplets 1420 in the second fluid 1418 and flow away from the junction 1410 along channel segment 1408. The channel segment 1408 may deliver the discrete droplets to an outlet reservoir fluidly coupled to the channel segment 1408, where they may be harvested. As an alternative, the channel segments 1401 and 1402 may meet at another junction upstream of the junction 1410. At such junction, beads and biological particles may form a mixture that is directed along another channel to the junction 1410 to yield droplets 1420. The mixture may provide the beads and biological particles in an alternating fashion, such that, for example, a droplet comprises a single bead and a single biological particle.

B. Samples and Cell Processing

A sample, e.g., samples comprising analytes such as nucleic acids, proteins, and/or cells, may be processed prior to, during, and/or after partitioning.

A sample may be derived from any useful source including any subject, such as a human subject. A sample may comprise material (e.g., one or more cells) from one or more different sources, such as one or more different subjects. Multiple samples, such as multiple samples from a single subject (e.g., multiple samples obtained in the same or different manners from the same or different bodily locations, and/or obtained at the same or different times (e.g., seconds, minutes, hours, days, weeks, months, or years apart)), or multiple samples from different subjects, may be obtained for analysis as described herein. For example, a first sample may be obtained from a subject at a first time and a second sample may be obtained from the subject at a second time later than the first time. The first time may be before a subject undergoes a treatment regimen or procedure (e.g., to address a disease or condition), and the second time may be during or after the subject undergoes the treatment regimen or procedure. In another example, a first sample may be obtained from a first bodily location or system of a subject (e.g., using a first collection technique) and a second sample may be obtained from a second bodily location or system of the subject (e.g., using a second collection technique), which second bodily location or system may be different than the first bodily location or system. In another example, multiple samples may be obtained from a subject at a same time from the same or different bodily locations. Different samples, such as different samples collected from different bodily locations of a same subject, at different times, from multiple different subjects, and/or using different collection techniques, may undergo the same or different processing (e.g., as described herein). For example, a first sample may undergo a first processing protocol and a second sample may undergo a second processing protocol.

A sample may be a biological sample, such as a cell sample (e.g., as described herein). A sample may include one or more analyte carriers, such as one or more cells and/or cellular constituents, such as one or more cell nuclei. For example, a sample may comprise a plurality of cells and/or cellular constituents. Components (e.g., cells or cellular constituents, such as cell nuclei) of a sample may be of a single type or a plurality of different types. For example, cells of a sample may include one or more different types of blood cells.

A biological sample may include a plurality of cells having different dimensions and features. In some cases, processing of the biological sample, such as cell separation and sorting (e.g., as described herein), may affect the distribution of dimensions and cellular features included in the sample by depleting cells having certain features and dimensions and/or isolating cells having certain features and dimensions.

A sample may undergo one or more processes in preparation for analysis (e.g., as described herein), including, but not limited to, filtration, selective precipitation, purification, centrifugation, permeabilization, isolation, agitation, heating, and/or other processes. For example, a sample may be filtered to remove a contaminant or other materials. In an example, a filtration process may comprise the use of microfluidics (e.g., to separate analyte carriers of different sizes, types, charges, or other features).

In an example, a sample comprising one or more cells may be processed to separate the one or more cells from other materials in the sample (e.g., using centrifugation and/or another process). In some cases, cells and/or cellular constituents of a sample may be processed to separate and/or sort groups of cells and/or cellular constituents, such as to separate and/or sort cells and/or cellular constituents of different types. Examples of cell separation include, but are not limited to, separation of white blood cells or immune cells from other blood cells and components, separation of circulating tumor cells from blood, and separation of bacteria from bodily cells and/or environmental materials. A separation process may comprise a positive selection process (e.g., targeting of a cell type of interest for retention for subsequent downstream analysis, such as by use of a monoclonal antibody that targets a surface marker of the cell type of interest), a negative selection process (e.g., removal of one or more cell types and retention of one or more other cell types of interest), and/or a depletion process (e.g., removal of a single cell type from a sample, such as removal of red blood cells from peripheral blood mononuclear cells).

Separation of one or more different types of cells may comprise, for example, centrifugation, filtration, microfluidic-based sorting, flow cytometry, fluorescence-activated cell sorting (FACS), magnetic-activated cell sorting (MACS), buoyancy-activated cell sorting (BACS), or any other useful method. For example, a flow cytometry method may be used to detect cells and/or cellular constituents based on a parameter such as a size, morphology, or protein expression. Flow cytometry-based cell sorting may comprise injecting a sample into a sheath fluid that conveys the cells and/or cellular constituents of the sample into a measurement region one at a time. In the measurement region, a light source such as a laser may interrogate the cells and/or cellular constituents and scattered light and/or fluorescence may be detected and converted into digital signals. A nozzle system (e.g., a vibrating nozzle system) may be used to generate droplets (e.g., aqueous droplets) comprising individual cells and/or cellular constituents. Droplets including cells and/or cellular constituents of interest (e.g., as determined via optical detection) may be labeled with an electric charge (e.g., using an electrical charging ring), which charge may be used to separate such droplets from droplets including other cells and/or cellular constituents. For example, FACS may comprise labeling cells and/or cellular constituents with fluorescent markers (e.g., using internal and/or external biomarkers). Cells and/or cellular constituents may then be measured and identified one by one and sorted based on the emitted fluorescence of the marker or absence thereof. MACS may use micro- or nano-scale magnetic particles to bind to cells and/or cellular constituents (e.g., via an antibody interaction with cell surface markers) to facilitate magnetic isolation of cells and/or cellular constituents of interest from other components of a sample (e.g., using a column-based analysis). BACS may use microbubbles (e.g., glass microbubbles) labeled with antibodies to target cells of interest. Cells and/or cellular components coupled to microbubbles may float to a surface of a solution, thereby separating target cells and/or cellular components from other components of a sample. Cell separation techniques may be used to enrich for populations of cells of interest (e.g., prior to partitioning, as described herein). For example, a sample comprising a plurality of cells including a plurality of cells of a given type may be subjected to a positive separation process. The plurality of cells of the given type may be labeled with a fluorescent marker (e.g., based on an expressed cell surface marker or another marker) and subjected to a FACS process to separate these cells from other cells of the plurality of cells. The selected cells may then be subjected to subsequent partition-based analysis (e.g., as described herein) or other downstream analysis. The fluorescent marker may be removed prior to such analysis or may be retained. The fluorescent marker may comprise an identifying feature, such as a nucleic acid barcode sequence and/or unique molecular identifier.

In another example, a first sample comprising a first plurality of cells including a first plurality of cells of a given type (e.g., immune cells expressing a particular marker or combination of markers) and a second sample comprising a second plurality of cells including a second plurality of cells of the given type may be subjected to a positive separation process. The first and second samples may be collected from the same or different subjects, at the same or different types, from the same or different bodily locations or systems, using the same or different collection techniques. For example, the first sample may be from a first subject and the second sample may be from a second subject different than the first subject. The first plurality of cells of the first sample may be provided a first plurality of fluorescent markers configured to label the first plurality of cells of the given type. The second plurality of cells of the second sample may be provided a second plurality of fluorescent markers configured to label the second plurality of cells of the given type. The first plurality of fluorescent markers may include a first identifying feature, such as a first barcode, while the second plurality of fluorescent markers may include a second identifying feature, such as a second barcode, that is different than the first identifying feature. The first plurality of fluorescent markers and the second plurality of fluorescent markers may fluoresce at the same intensities and over the same range of wavelengths upon excitation with a same excitation source (e.g., light source, such as a laser). The first and second samples may then be combined and subjected to a FACS process to separate cells of the given type from other cells based on the first plurality of fluorescent markers labeling the first plurality of cells of the given type and the second plurality of fluorescent markers labeling the second plurality of cells of the given type. Alternatively, the first and second samples may undergo separate FACS processes and the positively selected cells of the given type from the first sample and the positively selected cells of the given type from the second sample may then be combined for subsequent analysis. The encoded identifying features of the different fluorescent markers may be used to identify cells originating from the first sample and cells originating from the second sample. For example, the first and second identifying features may be configured to interact (e.g., in partitions, as described herein) with nucleic acid barcode molecules (e.g., as described herein) to generate barcoded nucleic acid products detectable using, e.g., nucleic acid sequencing.

C. Beads

A partition may comprise one or more unique identifiers, such as barcodes (e.g., a plurality of barcode nucleic acid molecules which comprise a plurality of partition-specific barcode sequences). Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below. Furthermore, and for avoidance of doubt, a barcoded nucleic acid molecule delivered via a microcapsule, refers to a nucleic acid molecule delivered via a microcapsule, wherein the nucleic acid molecule includes a barcode sequence; see e.g., paragraph 192 and immediately preceding sentence.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof. Methods and systems for partitioning barcode carrying beads into droplets are provided in US. Patent Publication Nos. 2019/0367997 and 2019/0064173, and International Application Nos. PCT/US20/17785 and PCT/US20/020486, each of which is herein entirely incorporated by reference for all purposes.

In some examples, beads, biological particles and droplets may flow along channels (e.g., the channels of a microfluidic device), in some cases at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a bead may have a diameter of less than about 10 nm, 100 nm, 500 nm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly (vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

Figure 3:
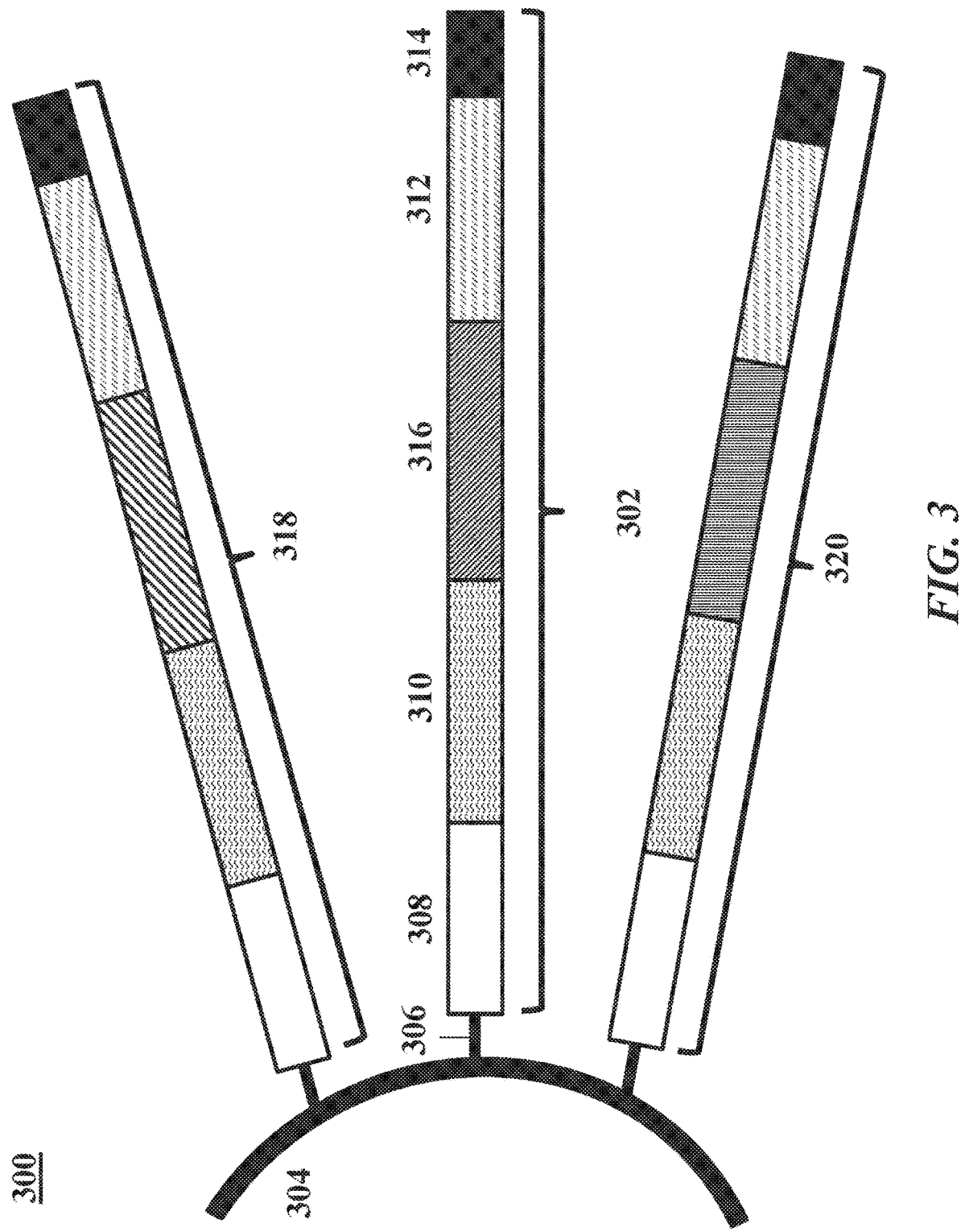
FIG. 3 shows an exemplary barcode carrying bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference. The generation of a barcoded sequence, see, e.g., FIG. 3, is described herein.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NETS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide, such as a barcoded nucleic acid molecule) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes (e.g., partition-specific barcode sequences). A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound (e.g., capture agent configured to couple to a secreted antibody or antigen binding fragment thereof) or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached, e.g., bound, barcode sequence into the aqueous, inner environment of the droplet.

Any suitable number of molecular tag molecules (e.g., primer, oligonucleotide, barcoded oligonucleotide, nucleic acid molecule, nucleic acid barcode molecule) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecular tag molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads (e.g., capture agent) during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), 3-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition (e.g., multi-omic method described elsewhere, herein). Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction. In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (µL), 5 µL, 1 µL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

D. Reagents

In accordance with certain aspects, biological particles may be partitioned along with lysis reagents in order to release the contents of the biological particles within the partition. See, e.g., U.S. Pat. Pub. 2018/0216162 (now U.S. Pat. No. 10,428,326), U.S. Pat. Pub. 2019/0100632 (now U.S. Pat. No. 10,590,244), and U.S. Pat. Pub. 2019/0233878, which are incorporated by reference in their entirety. Cell beads may be partitioned together with nucleic acid barcode molecules and the nucleic acid molecules of or derived from the cell bead (e.g., mRNA, cDNA, gDNA, secreted antibodies or antigen binding fragments thereof, etc.) can be barcoded as described elsewhere herein. In some embodiments, cell beads are co-partitioned with barcode carrying beads (e.g., gel beads) and the nucleic acid molecules of or derived from the cell bead are barcoded as described elsewhere herein. In such cases, the lysis agents can be contacted with the biological particle suspension concurrently with, or immediately prior to, the introduction of the biological particles into the partitioning junction/droplet generation zone, such as through an additional channel or channels upstream of the channel junction. In accordance with other aspects, additionally or alternatively, biological particles may be partitioned along with other reagents, as will be described further below.

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structures may have other geometries and/or configurations. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological particle's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template sequence comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, proteins, or secreted antibodies or antigen binding fragments thereof) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIGS. 1 and 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules from the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

FIG. 2 shows an example of a microfluidic channel structure for the controlled partitioning of beads into discrete droplets. A channel structure 200 can include a channel segment 202 communicating at a channel junction 206 (or intersection) with a reservoir 204. The reservoir 204 can be a chamber. Any reference to "reservoir," as used herein, can also refer to a "chamber." In operation, an aqueous fluid 208 that includes suspended beads 212 may be transported along the channel segment 202 into the junction 206 to meet a second fluid 210 that is immiscible with the aqueous fluid 208 in the reservoir 204 to create droplets 216, 218 of the aqueous fluid 208 flowing into the reservoir 204. At the junction 206 where the aqueous fluid 208 and the second fluid 210 meet, droplets can form based on factors such as the hydrodynamic forces at the junction 206, flow rates of the two fluids 208, 210, fluid properties, and certain geometric parameters (e.g., w, $h_0$, $\alpha$, etc.) of the channel structure 200. A plurality of droplets can be collected in the reservoir 204 by continuously injecting the aqueous fluid 208 from the channel segment 202 through the junction 206.

A discrete droplet generated may include a bead (e.g., as in occupied droplets 216). Alternatively, a discrete droplet generated may include more than one bead. Alternatively, a discrete droplet generated may not include any beads (e.g., as in unoccupied droplet 218). In some instances, a discrete droplet generated may contain one or more biological particles, as described elsewhere herein. In some instances, a discrete droplet generated may comprise one or more reagents, as described elsewhere herein.

In some instances, the aqueous fluid 208 can have a substantially uniform concentration or frequency of beads 212. The beads 212 can be introduced into the channel segment 202 from a separate channel (not shown in FIG. 2). The frequency of beads 212 in the channel segment 202 may be controlled by controlling the frequency in which the beads 212 are introduced into the channel segment 202 and/or the relative flow rates of the fluids in the channel segment 202 and the separate channel. In some instances, the beads can be introduced into the channel segment 202 from a plurality of different channels, and the frequency controlled accordingly.

In some instances, the aqueous fluid 208 in the channel segment 202 can comprise biological particles (e.g., described with reference to FIG. 1). In some instances, the aqueous fluid 208 can have a substantially uniform concentration or frequency of biological particles. As with the beads, the biological particles can be introduced into the channel segment 202 from a separate channel. The frequency or concentration of the biological particles in the aqueous fluid 208 in the channel segment 202 may be controlled by controlling the frequency in which the biological particles are introduced into the channel segment 202 and/or the relative flow rates of the fluids in the channel segment 202 and the separate channel. In some instances, the biological particles can be introduced into the channel segment 202 from a plurality of different channels, and the frequency controlled accordingly. In some instances, a first separate channel can introduce beads and a second separate channel can introduce biological particles into the channel segment 202. The first separate channel introducing the beads may be upstream or downstream of the second separate channel introducing the biological particles.

The second fluid 210 can comprise an oil, such as a fluorinated oil, that includes a fluorosurfactant for stabilizing the resulting droplets, for example, inhibiting subsequent coalescence of the resulting droplets.

In some instances, the second fluid 210 may not be subjected to and/or directed to any flow in or out of the reservoir 204. For example, the second fluid 210 may be substantially stationary in the reservoir 204. In some instances, the second fluid 210 may be subjected to flow within the reservoir 204, but not in or out of the reservoir 204, such as via application of pressure to the reservoir 204 and/or as affected by the incoming flow of the aqueous fluid

208 at the junction 206. Alternatively, the second fluid 210 may be subjected and/or directed to flow in or out of the reservoir 204. For example, the reservoir 204 can be a channel directing the second fluid 210 from upstream to downstream, transporting the generated droplets.

The channel structure 200 at or near the junction 206 may have certain geometric features that at least partly determine the sizes of the droplets formed by the channel structure 200. The channel segment 202 can have a height, $h_0$ and width, w, at or near the junction 206. By way of example, the channel segment 202 can comprise a rectangular cross-section that leads to a reservoir 204 having a wider cross-section (such as in width or diameter). Alternatively, the cross-section of the channel segment 202 can be other shapes, such as a circular shape, trapezoidal shape, polygonal shape, or any other shapes. The top and bottom walls of the reservoir 204 at or near the junction 206 can be inclined at an expansion angle, a. The expansion angle, $\alpha$, allows the tongue (portion of the aqueous fluid 208 leaving channel segment 202 at junction 206 and entering the reservoir 204 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and $\alpha$:

$$R_d \approx 0.44\left(1 + 2.2\sqrt{\tan\alpha}\,\frac{w}{h_0}\right)\frac{h_0}{\sqrt{\tan\alpha}}$$

By way of example, for a channel structure with w=21 μm, h=21 μm, and $\alpha$=3°, the predicted droplet size is 121 μm. In another example, for a channel structure with w=25 μm, h=25 μm, and $\alpha$=5°, the predicted droplet size is 123 μm. In another example, for a channel structure with w=28 μm, h=28 μm, and $\alpha$=7°, the predicted droplet size is 124 μm.

In some instances, the expansion angle, a, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 208 entering the junction 206 can be between about 0.04 microliters (μL)/minute (min) and about 40 μL/min. In some instances, the flow rate of the aqueous fluid 208 entering the junction 206 can be between about 0.01 microliters (μL)/minute (min) and about 100 μL/min. Alternatively, the flow rate of the aqueous fluid 208 entering the junction 206 can be less than about 0.01 μL/min. Alternatively, the flow rate of the aqueous fluid 208 entering the junction 206 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120, 130 μL/min, 140 μL/min, 150 μL/min, or greater. At lower flow rates, such as flow rates of about less than or equal to 10 microliters/minute, the droplet radius may not be dependent on the flow rate of the aqueous fluid 208 entering the junction 206.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 206) between aqueous fluid 208 channel segments (e.g., channel segment 202) and the reservoir 204. Alternatively or in addition, the throughput of droplet generation can be increased by increasing the flow rate of the aqueous fluid 208 in the channel segment 202.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Partitions comprising a barcode bead (e.g., a gel bead) associated with barcode molecules and a bead encapsulating cellular constituents (e.g., a cell bead) such as cellular nucleic acids can be useful in constituent analysis as is described in U.S. Patent Publication No. 2018/0216162, which is herein incorporated by reference in its entirety for all purposes.

E. Microwells

As described herein, one or more processes may be performed in a partition, which may be a well. The well may be a well of a plurality of wells of a substrate, such as a microwell of a microwell array or plate, or the well may be a microwell or microchamber of a device (e.g., microfluidic device) comprising a substrate. The well may be a well of a well array or plate, or the well may be a well or chamber of a device (e.g., fluidic device). Accordingly, the wells or microwells may assume an "open" configuration, in which the wells or microwells are exposed to the environment (e.g., contain an open surface) and are accessible on one planar face of the substrate, or the wells or microwells may assume a "closed" or "sealed" configuration, in which the microwells are not accessible on a planar face of the substrate. In some instances, the wells or microwells may be configured to toggle between "open" and "closed" configurations. For instance, an "open" microwell or set of microwells may be "closed" or "sealed" using a membrane (e.g., semi-permeable membrane), an oil (e.g., fluorinated oil to cover an aqueous solution), or a lid, as described elsewhere herein.

The well may have a volume of less than 1 milliliter (mL). For instance, the well may be configured to hold a volume of at most 1000 microliters (µL), at most 100 µL, at most 10 µL, at most 1 µL, at most 100 nanoliters (nL), at most 10 nL, at most 1 nL, at most 100 picoliters (pL), at most 10 (pL), or less. The well may be configured to hold a volume of about 1000 µL, about 100 µL, about 10 µL, about 1 µL, about 100 nL, about 10 nL, about 1 nL, about 100 pL, about 10 pL, etc. The well may be configured to hold a volume of at least 10 pL, at least 100 pL, at least 1 nL, at least 10 nL, at least 100 nL, at least 1 µL, at least 10 µL, at least 100 µL, at least 1000 µL, or more. The well may be configured to hold a volume in a range of volumes listed herein, for example, from about 5 nL to about 20 nL, from about 1 nL to about 100 nL, from about 500 pL to about 100 µL, etc. The well may be of a plurality of wells that have varying volumes and may be configured to hold a volume appropriate to accommodate any of the partition volumes described herein.

In some instances, a microwell array or plate comprises a single variety of microwells. In some instances, a microwell array or plate comprises a variety of microwells. For instance, the microwell array or plate may comprise one or more types of microwells within a single microwell array or plate. The types of microwells may have different dimensions (e.g., length, width, diameter, depth, cross-sectional area, etc.), shapes (e.g., circular, triangular, square, rectangular, pentagonal, hexagonal, heptagonal, octagonal, nonagonal, decagonal, etc.), aspect ratios, or other physical characteristics. The microwell array or plate may comprise any number of different types of microwells. For example, the microwell array or plate may comprise 1, 2, 3, 4, 5, 6, 7, 8, 9, 10, 20, 30, 40, 50, 60, 70, 80, 90, 100, 200, 300, 400, 500, 600, 700, 800, 900, 1000 or more different types of microwells. A well may have any dimension (e.g., length, width, diameter, depth, cross-sectional area, volume, etc.), shape (e.g., circular, triangular, square, rectangular, pentagonal, hexagonal, heptagonal, octagonal, nonagonal, decagonal, other polygonal, etc.), aspect ratios, or other physical characteristics described herein with respect to any well.

In certain instances, the microwell array or plate comprises different types of microwells that are located adjacent to one another within the array or plate. For instance, a microwell with one set of dimensions may be located adjacent to and in contact with another microwell with a different set of dimensions. Similarly, microwells of different geometries may be placed adjacent to or in contact with one another. The adjacent microwells may be configured to hold different articles; for example, one microwell may be used to contain a cell, cell bead, or other sample (e.g., cellular components, nucleic acid molecules, etc.) while the adjacent microwell may be used to contain a microcapsule, droplet, bead, or other reagent. In some cases, the adjacent microwells may be configured to merge the contents held within, e.g., upon application of a stimulus, or spontaneously, upon contact of the articles in each microwell.

As is described elsewhere herein, a plurality of partitions may be used in the systems, compositions, and methods described herein. For example, any suitable number of partitions (e.g., wells or droplets) can be generated or otherwise provided. For example, in the case when wells are used, at least about 1,000 wells, at least about 5,000 wells, at least about 10,000 wells, at least about 50,000 wells, at least about 100,000 wells, at least about 500,000 wells, at least about 1,000,000 wells, at least about 5,000,000 wells at least about 10,000,000 wells, at least about 50,000,000 wells, at least about 100,000,000 wells, at least about 500,000,000 wells, at least about 1,000,000,000 wells, or more wells can be generated or otherwise provided. Moreover, the plurality of wells may comprise both unoccupied wells (e.g., empty wells) and occupied wells.

A well may comprise any of the reagents described herein, or combinations thereof. These reagents may include, for example, barcode molecules, enzymes, adapters, and combinations thereof. The reagents may be physically separated from a sample (e.g., a cell, cell bead, or cellular components, e.g., proteins, nucleic acid molecules, etc.) that is placed in the well. This physical separation may be accomplished by containing the reagents within, or coupling to, a microcapsule or bead that is placed within a well. The physical separation may also be accomplished by dispensing the reagents in the well and overlaying the reagents with a layer that is, for example, dissolvable, meltable, or permeable prior to introducing the polynucleotide sample into the well. This layer may be, for example, an oil, wax, membrane (e.g., semi-permeable membrane), or the like. The well may be sealed at any point, for example, after addition of the microcapsule or bead, after addition of the reagents, or after addition of either of these components. The sealing of the well may be useful for a variety of purposes, including preventing escape of beads or loaded reagents from the well, permitting select delivery of certain reagents (e.g., via the use of a semi-permeable membrane), for storage of the well prior to or following further processing, etc.

A well may comprise free reagents and/or reagents encapsulated in, or otherwise coupled to or associated with, microcapsules, beads, or droplets. Any of the reagents described in this disclosure may be encapsulated in, or otherwise coupled to, a microcapsule, droplet, or bead, with any chemicals, particles, and elements suitable for sample processing reactions involving biomolecules, such as, but not limited to, nucleic acid molecules and proteins. For example, a bead or droplet used in a sample preparation reaction for DNA sequencing may comprise one or more of the following reagents: enzymes, restriction enzymes (e.g., multiple cutters), ligase, polymerase, fluorophores, oligonucleotide barcodes, adapters, buffers, nucleotides (e.g., dNTPs, ddNTPs) and the like.

Additional examples of reagents include, but are not limited to: buffers, acidic solution, basic solution, temperature-sensitive enzymes, pH-sensitive enzymes, light-sensitive enzymes, metals, metal ions, magnesium chloride, sodium chloride, manganese, aqueous buffer, mild buffer, ionic buffer, inhibitor, enzyme, protein, polynucleotide, antibodies, saccharides, lipid, oil, salt, ion, detergents, ionic detergents, non-ionic detergents, oligonucleotides, nucleotides, deoxyribonucleotide triphosphates (dNTPs), dideoxyribonucleotide triphosphates (ddNTPs), DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA, polymerase, ligase, restriction enzymes, proteases, nucleases, protease inhibitors, nuclease inhibitors, chelating agents, reducing agents, oxidizing agents, fluorophores, probes, chromophores, dyes, organics, emulsifiers, surfactants, stabilizers, polymers, water, small molecules, pharmaceuticals, radioactive molecules, preservatives, antibiotics, aptamers, and pharmaceutical drug compounds. As described herein, one or more reagents in the well may be used to perform one or more reactions, including but not limited to: cell lysis, cell fixation, permeabilization, nucleic acid reactions, e.g., nucleic acid extension reactions, amplification, reverse transcription, transposase reactions (e.g., tagmentation), etc.

The wells may be provided as a part of a kit. For example, a kit may comprise instructions for use, a microwell array or device, and reagents (e.g., beads). The kit may comprise any useful reagents for performing the processes described herein, e.g., nucleic acid reactions, barcoding of nucleic acid molecules, sample processing (e.g., for cell lysis, fixation, and/or permeabilization).

In some cases, a well comprises a microcapsule, bead, or droplet that comprises a set of reagents that has a similar attribute (e.g., a set of enzymes, a set of minerals, a set of oligonucleotides, a mixture of different barcode molecules, a mixture of identical barcode molecules). In other cases, a microcapsule, bead, or droplet comprises a heterogeneous mixture of reagents. In some cases, the heterogeneous mixture of reagents can comprise all components necessary to perform a reaction. In some cases, such mixture can comprise all components necessary to perform a reaction, except for 1, 2, 3, 4, 5, or more components necessary to perform a reaction. In some cases, such additional components are contained within, or otherwise coupled to, a different microcapsule, droplet, or bead, or within a solution within a partition (e.g., microwell) of the system.

Figure 5:
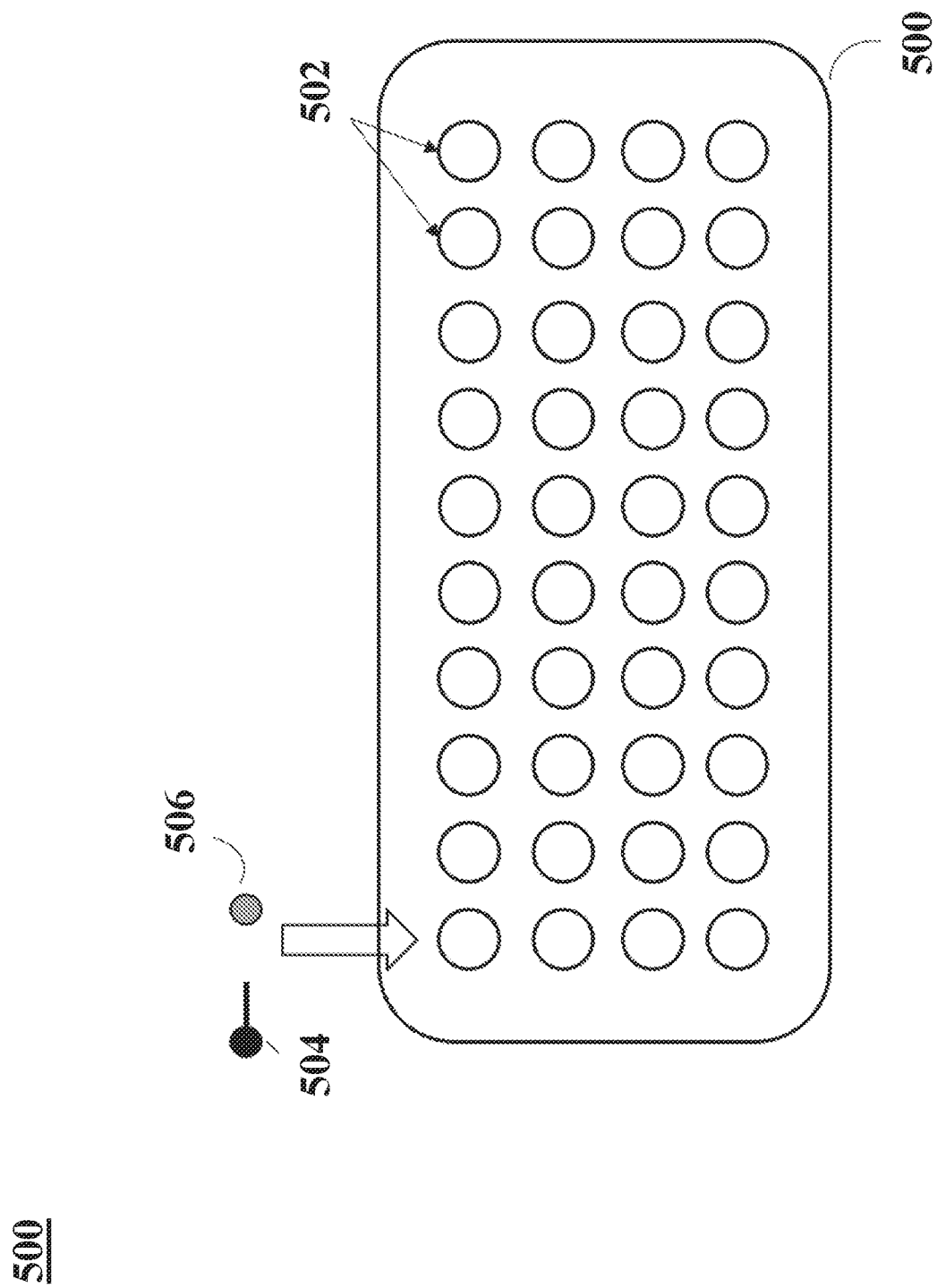
FIG. 5 schematically illustrates an exemplary microwell array.

FIG. 5 schematically illustrates an example of a microwell array. The array can be contained within a substrate 500. The substrate 500 comprises a plurality of wells 502. The wells 1002 may be of any size or shape, and the spacing between the wells, the number of wells per substrate, as well as the density of the wells on the substrate 500 can be modified, depending on the particular application. In one such example application, a sample molecule 506, which may comprise a cell or cellular components (e.g., nucleic acid molecules) is co-partitioned with a bead 504, which may comprise a nucleic acid barcode molecule coupled thereto. The wells 502 may be loaded using gravity or other loading technique (e.g., centrifugation, liquid handler, acoustic loading, optoelectronic, etc.). In some instances, at least one of the wells 502 contains a single sample molecule 506 (e.g., cell) and a single bead 504.

Reagents may be loaded into a well either sequentially or concurrently. In some cases, reagents are introduced to the device either before or after a particular operation. In some cases, reagents (which may be provided, in certain instances, in microcapsules, droplets, or beads) are introduced sequentially such that different reactions or operations occur at different steps. The reagents (or microcapsules, droplets, or beads) may also be loaded at operations interspersed with a reaction or operation step. For example, microcapsules (or droplets or beads) comprising reagents for fragmenting polynucleotides (e.g., restriction enzymes) and/or other enzymes (e.g., transposases, ligases, polymerases, etc.) may be loaded into the well or plurality of wells, followed by loading of microcapsules, droplets, or beads comprising reagents for attaching nucleic acid barcode molecules to a sample nucleic acid molecule. Reagents may be provided concurrently or sequentially with a sample, e.g., a cell or cellular components (e.g., organelles, proteins, nucleic acid molecules, carbohydrates, lipids, etc.). Accordingly, use of wells may be useful in performing multi-step operations or reactions.

As described elsewhere herein, the nucleic acid barcode molecules and other reagents may be contained within a microcapsule, bead, or droplet. These microcapsules, beads, or droplets may be loaded into a partition (e.g., a microwell) before, after, or concurrently with the loading of a cell, such that each cell is contacted with a different microcapsule, bead, or droplet. This technique may be used to attach a unique nucleic acid barcode molecule to nucleic acid molecules obtained from each cell. Alternatively or in addition to, the sample nucleic acid molecules may be attached to a support. For instance, the partition (e.g., microwell) may comprise a bead which has coupled thereto a plurality of nucleic acid barcode molecules. The sample nucleic acid molecules, or derivatives thereof, may couple or attach to the nucleic acid barcode molecules on the support. The resulting barcoded nucleic acid molecules may then be removed from the partition, and in some instances, pooled and sequenced. In such cases, the nucleic acid barcode sequences may be used to trace the origin of the sample nucleic acid molecule. For example, polynucleotides with identical barcodes may be determined to originate from the same cell or partition, while polynucleotides with different barcodes may be determined to originate from different cells or partitions.

The samples or reagents may be loaded in the wells or microwells using a variety of approaches. The samples (e.g., a cell, cell bead, or cellular component) or reagents (as described herein) may be loaded into the well or microwell using an external force, e.g., gravitational force, electrical force, magnetic force, or using mechanisms to drive the sample or reagents into the well, e.g., via pressure-driven flow, centrifugation, optoelectronics, acoustic loading, electrokinetic pumping, vacuum, capillary flow, etc. In certain cases, a fluid handling system may be used to load the samples or reagents into the well. The loading of the samples or reagents may follow a Poissonian distribution or a non-Poissonian distribution, e.g., super Poisson or sub-Poisson. The geometry, spacing between wells, density, and size of the microwells may be modified to accommodate a useful sample or reagent distribution; for instance, the size and spacing of the microwells may be adjusted such that the sample or reagents may be distributed in a super-Poissonian fashion.

In one particular non-limiting example, the microwell array or plate comprises pairs of microwells, in which each pair of microwells is configured to hold a droplet (e.g., comprising a single cell) and a single bead (such as those described herein, which may, in some instances, also be encapsulated in a droplet). The droplet and the bead (or droplet containing the bead) may be loaded simultaneously or sequentially, and the droplet and the bead may be merged, e.g., upon contact of the droplet and the bead, or upon application of a stimulus (e.g., external force, agitation, heat, light, magnetic or electric force, etc.). In some cases, the loading of the droplet and the bead is super-Poissonian. In other examples of pairs of microwells, the wells are configured to hold two droplets comprising different reagents and/or samples, which are merged upon contact or upon application of a stimulus. In such instances, the droplet of one microwell of the pair can comprise reagents that may react with an agent in the droplet of the other microwell of the pair. For instance, one droplet can comprise reagents that are configured to release the nucleic acid barcode molecules of a bead contained in another droplet, located in the adjacent microwell. Upon merging of the droplets, the nucleic acid barcode molecules may be released from the bead into the partition (e.g., the microwell or microwell pair that are in contact), and further processing may be performed (e.g., barcoding, nucleic acid reactions, etc.). In cases where intact or live cells are loaded in the microwells, one of the droplets may comprise lysis reagents for lysing the cell upon droplet merging.

A droplet or microcapsule may be partitioned into a well. The droplets may be selected or subjected to pre-processing prior to loading into a well. For instance, the droplets may comprise cells, and only certain droplets, such as those containing a single cell (or at least one cell), may be selected for use in loading of the wells. Such a pre-selection process may be useful in efficient loading of single cells, such as to obtain a non-Poissonian distribution, or to pre-filter cells for a selected characteristic prior to further partitioning in the wells. Additionally, the technique may be useful in obtaining or preventing cell doublet or multiplet formation prior to or during loading of the microwell.

In some instances, the wells can comprise nucleic acid barcode molecules attached thereto. The nucleic acid barcode molecules may be attached to a surface of the well (e.g., a wall of the well). The nucleic acid barcode molecule (e.g., a partition-specific barcode sequence) of one well may differ from the nucleic acid barcode molecule of another well, which can permit identification of the contents contained with a single partition or well. In some cases, the nucleic acid barcode molecule can comprise a spatial barcode sequence that can identify a spatial coordinate of a well, such as within the well array or well plate. In some cases, the nucleic acid barcode molecule can comprise a unique molecular identifier for individual molecule identification. In some instances, the nucleic acid barcode molecules may be configured to attach to or capture a nucleic acid molecule within a sample or cell distributed in the well. For example, the nucleic acid barcode molecules may comprise a capture sequence that may be used to capture or hybridize to a nucleic acid molecule (e.g., RNA, DNA) within the sample. In some instances, the nucleic acid barcode molecules may be releasable from the microwell. For instance, the nucleic acid barcode molecules may comprise a chemical cross-linker which may be cleaved upon application of a stimulus (e.g., photo-, magnetic, chemical, biological, stimulus). The released nucleic acid barcode molecules, which may be hybridized or configured to hybridize to a sample nucleic acid molecule, may be collected and pooled for further processing, which can include nucleic acid processing (e.g., amplification, extension, reverse transcription, etc.) and/or characterization (e.g., sequencing). In such cases, the unique partition-specific barcode sequences may be used to identify the cell or partition from which a nucleic acid molecule originated.

Characterization of samples within a well may be performed. Such characterization can include, in non-limiting examples, imaging of the sample (e.g., cell, cell bead, or cellular components) or derivatives thereof. Characterization techniques such as microscopy or imaging may be useful in measuring sample profiles in fixed spatial locations. For instance, when cells are partitioned, optionally with beads, imaging of each microwell and the contents contained therein may provide useful information on cell doublet formation (e.g., frequency, spatial locations, etc.), cell-bead pair efficiency, cell viability, cell size, cell morphology, expression level of a biomarker (e.g., a surface marker, a fluorescently labeled molecule therein, etc.), cell or bead loading rate, number of cell-bead pairs, etc. In some instances, imaging may be used to characterize live cells in the wells, including, but not limited to: dynamic live-cell tracking, cell-cell interactions (when two or more cells are co-partitioned), cell proliferation, etc. Alternatively or in addition to, imaging may be used to characterize a quantity of amplification products in the well.

In operation, a well may be loaded with a sample and reagents, simultaneously or sequentially. When cells or cell beads are loaded, the well may be subjected to washing, e.g., to remove excess cells from the well, microwell array, or plate. Similarly, washing may be performed to remove excess beads or other reagents from the well, microwell array, or plate. In the instances where live cells are used, the cells may be lysed in the individual partitions to release the intracellular components or cellular analytes. Alternatively, the cells may be fixed or permeabilized in the individual partitions. The intracellular components or cellular analytes may couple to a support, e.g., on a surface of the microwell, on a solid support (e.g., bead), or they may be collected for further downstream processing. For instance, after cell lysis, the intracellular components or cellular analytes may be transferred to individual droplets or other partitions for barcoding. Alternatively, or in addition to, the intracellular components or cellular analytes (e.g., nucleic acid molecules) may couple to a bead comprising a nucleic acid barcode molecule; subsequently, the bead may be collected and further processed, e.g., subjected to nucleic acid reaction such as reverse transcription, amplification, or extension, and the nucleic acid molecules thereon may be further characterized, e.g., via sequencing. Alternatively, or in addition to, the intracellular components or cellular analytes may be barcoded in the well (e.g., using a bead comprising nucleic acid barcode molecules that are releasable or on a surface of the microwell comprising nucleic acid barcode molecules). The barcoded nucleic acid molecules or analytes may be further processed in the well, or the barcoded nucleic acid molecules or analytes may be collected from the individual partitions and subjected to further processing outside the partition. Further processing can include nucleic acid processing (e.g., performing an amplification, extension) or characterization (e.g., fluorescence monitoring of amplified molecules, sequencing). At any convenient or useful step, the well (or microwell array or plate) may be sealed (e.g., using an oil, membrane, wax, etc.), which enables storage of the assay or selective introduction of additional reagents.

Figure 6:
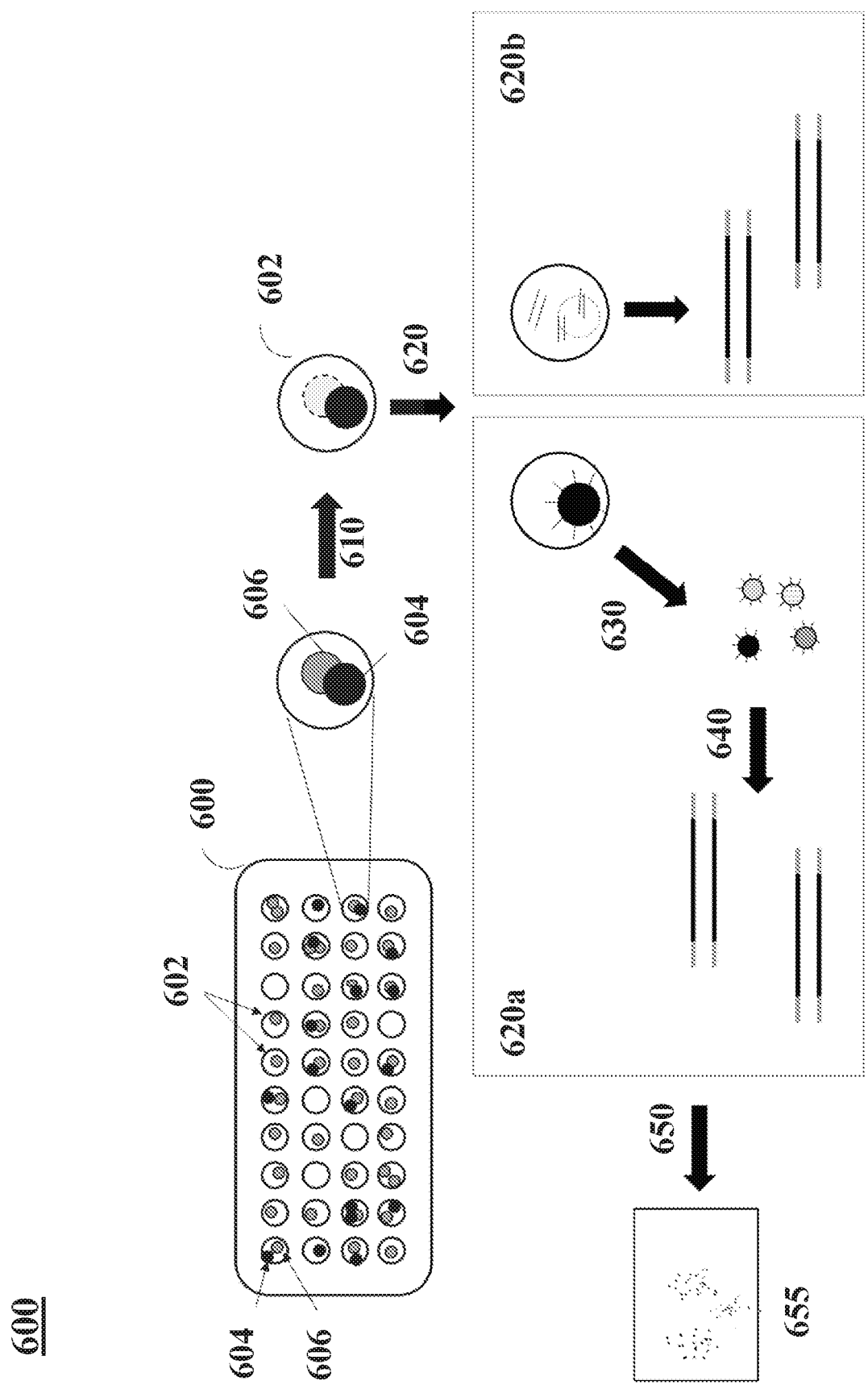
FIG. 6 schematically illustrates an example workflow for processing nucleic acid molecules.

FIG. 6 schematically shows an example workflow for processing nucleic acid molecules within a sample. A substrate 600 comprising a plurality of microwells 602 may be provided. A sample 606 which may comprise a cell, cell bead, cellular components or analytes (e.g., proteins and/or nucleic acid molecules) can be co-partitioned, in a plurality of microwells 602, with a plurality of beads 604 comprising nucleic acid barcode molecules. During process 610, the sample 606 may be processed within the partition. For instance, in the case of live cells, the cell may be subjected to conditions sufficient to lyse the cells and release the analytes contained therein. In process 620, the bead 604 may be further processed. By way of example, processes 620*a* and 620*b* schematically illustrate different workflows, depending on the properties of the bead 604.

In 620*a*, the bead comprises nucleic acid barcode molecules that are attached thereto, and sample nucleic acid molecules (e.g., RNA, DNA) may attach, e.g., via hybridization of ligation, to the nucleic acid barcode molecules. Such attachment may occur on the bead. In process 630, the beads 604 from multiple wells 602 may be collected and pooled. Further processing may be performed in process 640. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 650, further characterization, such as sequencing may be performed to generate sequencing reads. The sequencing reads may yield information on individual cells or populations of cells, which may be represented visually or graphically, e.g., in a plot 655.

In 620*b*, the bead comprises nucleic acid barcode molecules that are releasably attached thereto, as described below. The bead may degrade or otherwise release the nucleic acid barcode molecules into the well 602; the nucleic acid barcode molecules may then be used to barcode nucleic acid molecules within the well 602. Further processing may be performed either inside the partition or outside the partition. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 650, further characterization, such as sequencing may be performed to generate sequencing reads. The sequencing reads may yield information on individual cells or populations of cells, which may be represented visually or graphically, e.g., in a plot 655.

VII. Detection and Analysis

A. Generation of Barcoded Molecules

Barcodes as described herein may be used to associate one or more analytes (e.g., secreted molecules or cellular nucleotide sequences such as mRNAs) with a cell and/or a partition (e.g., droplet or well) upon analyzing the barcodes using e.g., sequencing reads generated using a sequencer, such as an Illumina sequencer.

The herein described methods may comprise use of multiple barcodes to analyze multiple analytes and cellular molecules such as antibodies and/or mRNA molecules. A barcode may be a nucleic acid sequence (barcode sequence). A first barcode may be different from a second barcode. For example, the nucleic acid sequence of a first barcode sequence may be different from that of a second barcode sequence. As described herein, nucleic acid molecules comprising a barcode sequence may be coupled to other molecules, polymer, or particles. For example, nucleic acid molecules comprising a barcode sequence may be coupled to MHC molecules (e.g., tetrameric MHC-peptide complexes comprising a barcode sequence), secondary binding agents (e.g., an antibody coupled to a barcode sequence), polymers (e.g., dextramers or polymers capable of forming hydrogels), and/or beads (e.g., beads in emulsion droplets or in wells of a microwell array). Use of one or more barcodes may allow measurement and analysis of one or more analytes of a cell and may allow associating the one or more analytes with the respective cell. This may be particularly advantageous when measuring and analyzing multiple analytes (e.g., secreted molecules and/or mRNAs) from a single cell or from a plurality of cells such as one or more cell populations (e.g., immune cells). In such cases, a first barcode may be used to measure a first analyte of a cell (e.g., a secreted molecule such as an antibody), and a second barcode may be used to measure a second analyte of the cell (e.g., an mRNA molecule), and so forth. In these instances, a partition or cell specific barcode (e.g., attached to a bead, such as a gel bead) may be utilized to link the first barcode and the second barcode to attribute one or more analytes to a single cell. The analysis of an immune cell (e.g., a T cell, B cell, plasma cell, or dendritic cell), for example, may comprise measuring one or more signaling molecules (e.g., antibodies) that may be secreted upon stimulation of the cell (e.g., by using a stimulatory molecule), and one or more mRNA molecules that may be released from the cell upon cell lysis for analyzing, e.g., immune cell receptor gene segments (e.g., a V(D)J sequence of a T cell receptor (TCR)). See, e.g., U.S. Pat. Pub. 2018/0105808, which is incorporated by reference in its entirety, for exemplary molecules and methods for analyzing V(D)J sequences of single cells using nucleic acid barcode molecules.

FIG. 3 illustrates an example of a barcode carrying bead. A nucleic acid molecule 302, such as an oligonucleotide, can be coupled to a bead 304 by a releasable linkage 306, such as, for example, a disulfide linker. The same bead 304 may be coupled (e.g., via releasable linkage) to one or more other nucleic acid molecules 318, 320. The nucleic acid molecule 302 may be or comprise a barcode. As noted elsewhere herein, the structure of the barcode may comprise a number of sequence elements. The nucleic acid molecule 302 may comprise a functional sequence 308 that may be used in subsequent processing. For example, the functional sequence 308 may include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule 302 may comprise a barcode sequence 310 for use in barcoding the sample (e.g., DNA, RNA, protein, antibody, etc.). In some cases, the barcode sequence 310 can be bead-specific such that the barcode sequence 310 is common to all nucleic acid molecules (e.g., including nucleic acid molecule 302) coupled to the same bead 304. Alternatively or in addition, the barcode sequence 310 can be partition-specific such that the barcode sequence 310 is common to all nucleic acid molecules coupled to one or more beads that are partitioned into the same partition. The nucleic acid molecule 302 may comprise a specific priming sequence 312, such as an mRNA specific priming sequence (e.g., poly-T sequence), a targeted priming sequence, and/or a random priming sequence. The nucleic acid molecule 302 may comprise an anchoring sequence 314 to ensure that the specific priming sequence 312 hybridizes at the sequence end (e.g., of the mRNA). For example, the anchoring sequence 314 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 302 may comprise a unique molecular identifying sequence 316 (e.g., unique molecular identifier (UMI)). In some cases, the unique molecular identifying sequence 316 may comprise from about 5 to about 8 nucleotides. Alternatively, the unique molecular identifying sequence 316 may compress less than about 5 or more than about 8 nucleotides. The unique molecular identifying sequence 316 may be a unique sequence that varies across individual nucleic acid molecules (e.g., 302, 318, 320, etc.) coupled to a single bead (e.g., bead 304). In some cases, the unique molecular identifying sequence 316 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 3 shows three nucleic acid molecules 302, 318, 320 coupled to the surface of the bead 304, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 308, 310, 312, etc.) and variable or unique sequence segments (e.g., 316) between different individual nucleic acid molecules coupled to the same bead.

A biological particle (e.g., cell, DNA, RNA, etc.) can be co-partitioned along with a barcode bearing bead 304. The barcoded nucleic acid molecules 302, 318, 320 can be released from the bead 304 in the partition. By way of example, in the context of analyzing sample RNA, the poly-T segment (e.g., 312) of one of the released nucleic acid molecules (e.g., 302) can hybridize to the poly-A tail of a mRNA molecule. Reverse transcription may result in a cDNA transcript of the mRNA, but which transcript includes each of the sequence segments 308, 310, 316 of the nucleic acid molecule 302. Because the nucleic acid molecule 302 comprises an anchoring sequence 314, it will more likely hybridize to and prime reverse transcription at the sequence end of the poly-A tail of the mRNA. Within any given partition, all of the cDNA transcripts of the individual mRNA molecules may include a common barcode sequence segment 310. However, the transcripts made from the different mRNA molecules within a given partition may vary at the unique molecular identifying sequence 312 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents. In such cases, further processing may be performed, in the partitions or outside the partitions (e.g., in bulk). For instance, the RNA molecules on the beads may be subjected to reverse transcription or other nucleic acid processing, additional adapter sequences may be added to the barcoded nucleic acid molecules, or other nucleic acid reactions (e.g., amplification, nucleic acid extension) may be performed. The beads or products thereof (e.g., barcoded nucleic acid molecules) may be collected from the partitions, and/or pooled together and subsequently subjected to clean up and further characterization (e.g., sequencing).

The operations described herein may be performed at any useful or convenient step. For instance, the beads comprising nucleic acid barcode molecules may be introduced into a partition (e.g., well or droplet) prior to, during, or following introduction of a sample into the partition. The nucleic acid molecules of a sample may be subjected to barcoding, which may occur on the bead (in cases where the nucleic acid molecules remain coupled to the bead) or following release of the nucleic acid barcode molecules into the partition. In cases where the nucleic acid molecules from the sample remain attached to the bead, the beads from various partitions may be collected, pooled, and subjected to further processing (e.g., reverse transcription, adapter attachment, amplification, clean up, sequencing). In other instances, the processing may occur in the partition. For example, conditions sufficient for barcoding, adapter attachment, reverse transcription, or other nucleic acid processing operations may be provided in the partition and performed prior to clean up and sequencing.

In some instances, a bead may comprise a capture sequence or binding sequence configured to bind to a corresponding capture sequence or binding sequence. In some instances, a bead may comprise a plurality of different capture sequences or binding sequences configured to bind to different respective corresponding capture sequences or binding sequences. For example, a bead may comprise a first subset of one or more capture sequences each configured to bind to a first corresponding capture sequence, a second subset of one or more capture sequences each configured to bind to a second corresponding capture sequence, a third subset of one or more capture sequences each configured to bind to a third corresponding capture sequence, and etc. A bead may comprise any number of different capture sequences. In some instances, a bead may comprise at least 2, 3, 4, 5, 6, 7, 8, 9, 10 or more different capture sequences or binding sequences configured to bind to different respective capture sequences or binding sequences, respectively. Alternatively or in addition, a bead may comprise at most about 10, 9, 8, 7, 6, 5, 4, 3, or 2 different capture sequences or binding sequences configured to bind to different respective capture sequences or binding sequences. In some instances, the different capture sequences or binding sequences may be configured to facilitate analysis of a same type of analyte. In some instances, the different capture sequences or binding sequences may be configured to facilitate analysis of different types of analytes (with the same bead). The capture sequence may be designed to attach to a corresponding capture sequence. Beneficially, such corresponding capture sequence may be introduced to, or otherwise induced in, a biological particle (e.g., cell, cell bead, etc.) for performing different assays in various formats (e.g., barcoded antibodies comprising the corresponding capture sequence, barcoded MHC dextramers comprising the corresponding capture sequence, barcoded guide RNA molecules comprising the corresponding capture sequence, etc.), such that the corresponding capture sequence may later interact with the capture sequence associated with the bead. In some instances, a capture sequence coupled to a bead (or other support) may be configured to attach to a linker molecule, such as a splint molecule, wherein the linker molecule is configured to couple the bead (or other support) to other molecules through the linker molecule, such as to one or more analytes or one or more other linker molecules.

Figure 4:
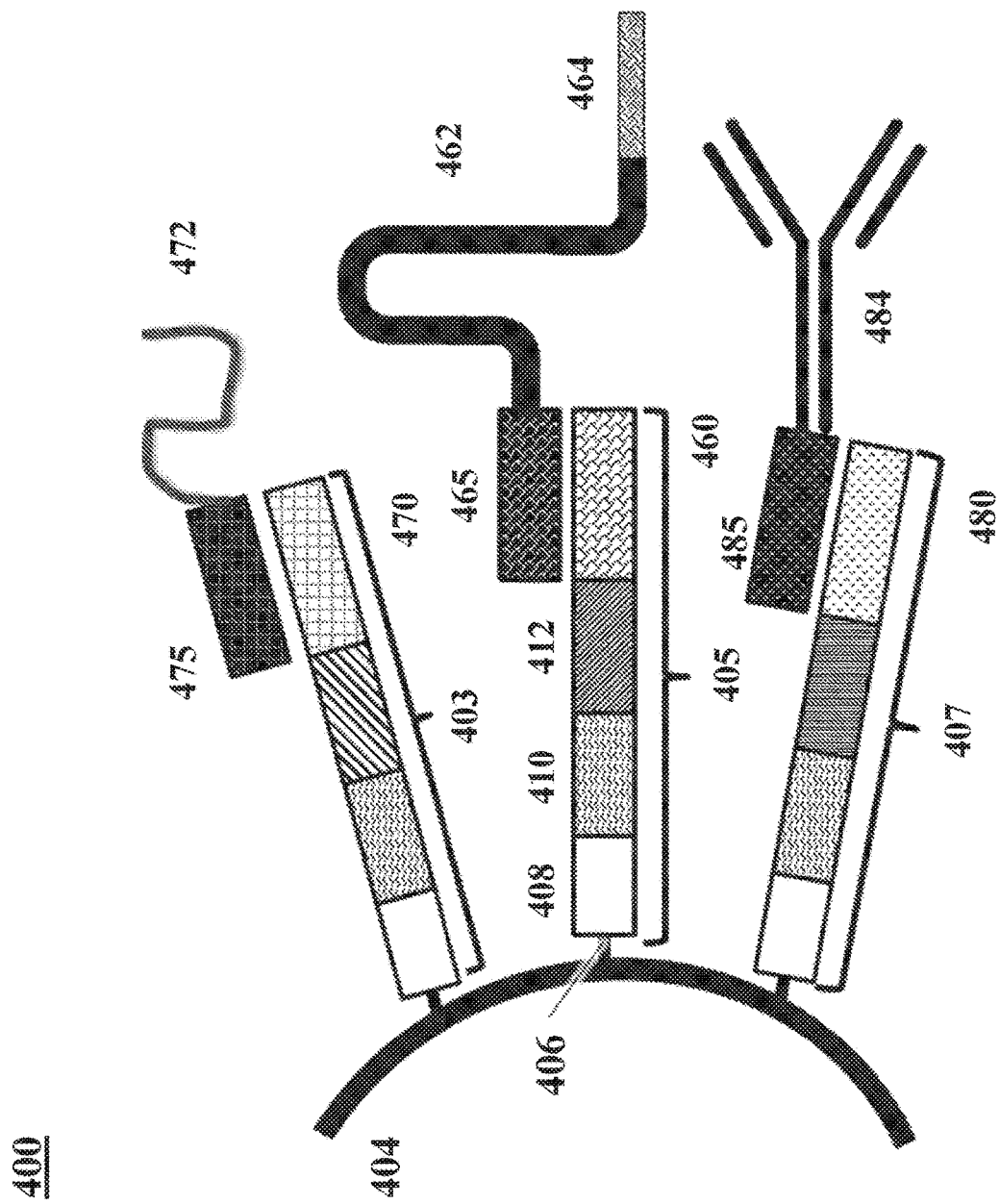
FIG. 4 illustrates another example of a barcode carrying bead.

FIG. 4 illustrates another example of a barcode carrying bead. A nucleic acid molecule 405, such as an oligonucleotide, can be coupled to a bead 404 by a releasable linkage 406, such as, for example, a disulfide linker. The nucleic acid molecule 405 may comprise a first capture sequence 460. The same bead 404 may be coupled (e.g., via releasable linkage) to one or more other nucleic acid molecules 403, 407 comprising other capture sequences. The nucleic acid molecule 405 may be or comprise a barcode. As noted elsewhere herein, the structure of the barcode may comprise a number of sequence elements, such as a functional sequence 408 (e.g., flow cell attachment sequence, sequencing primer sequence, etc.), a barcode sequence 410 (e.g., bead-specific sequence common to bead, partition-specific sequence common to partition, etc.), and a unique molecular identifier 412 (e.g., unique sequence within different molecules attached to the bead), or partial sequences thereof. The capture sequence 460 may be configured to attach to a corresponding capture sequence 465. In some instances, the corresponding capture sequence 465 may be coupled to another molecule that may be an analyte or an intermediary carrier. For example, as illustrated in FIG. 4, the corresponding capture sequence 465 is coupled to a guide RNA molecule 462 comprising a target sequence 464, wherein the target sequence 464 is configured to attach to the analyte. Another oligonucleotide molecule 407 attached to the bead 404 comprises a second capture sequence 480 which is configured to attach to a second corresponding capture sequence 485. As illustrated in FIG. 4, the second corresponding capture sequence 485 is coupled to an antibody 482. In some cases, the antibody 482 may have binding specificity to an analyte (e.g., surface protein). Alternatively, the antibody 482 may not have binding specificity. Another oligonucleotide molecule 403 attached to the bead 404 comprises a third capture sequence 470 which is configured to attach to a second corresponding capture sequence 475. As illustrated in FIG. 4, the third corresponding capture sequence 475 is coupled to a molecule 472. The molecule 472 may or may not be configured to target an analyte. The other oligonucleotide molecules 403, 407 may comprise the other sequences (e.g., functional sequence, barcode sequence, UMI, etc.) described with respect to oligonucleotide molecule 905. While a single oligonucleotide molecule comprising each capture sequence is illustrated in FIG. 4, it will be appreciated that, for each capture sequence, the bead may comprise a set of one or more oligonucleotide molecules each comprising the capture sequence. For example, the bead may comprise any number of sets of one or more different capture sequences. Alternatively or in addition, the bead 404 may comprise other capture sequences. Alternatively or in addition, the bead 404 may comprise fewer types of capture sequences (e.g., two capture sequences). Alternatively or in addition, the bead 404 may comprise oligonucleotide molecule(s) comprising a priming sequence, such as a specific priming sequence such as an mRNA specific priming sequence (e.g., poly-T sequence), a targeted priming sequence, and/or a random priming sequence, for example, to facilitate an assay for gene expression.

The herein disclosed methods and systems may further comprise partitioning cell beads into a plurality of partitions with a plurality of nucleic acid molecules comprising a cell-specific barcode sequence (see, e.g., the barcode molecules described in FIG. 3 or FIG. 4). In some instances, the cell specific barcodes are attached to a bead, such a gel bead. The cellular barcodes may be releasably attached to the bead as described elsewhere herein. Cell beads and cellular barcodes (e.g., attached to a bead, such as a gel bead) may be partitioned in a droplet or a well. The droplet may be an emulsion droplet and may comprise a cell bead. The emulsion droplet may be formed or generated as described elsewhere herein, e.g., by contacting two phases (e.g., a first and a second phase) that are immiscible (e.g., an aqueous phase and an oil). The hydrogel matrix forming the cell bead may be dissolved, thus releasing an analyte conjugate comprising an analyte (e.g., a cytokine), a capture agent and a reporter agent comprising the first barcode. The cell bead may be dissolved using one or more stimuli such as change in pH, temperature, or ion concentration within the partition. In some instances, the cell is lysed, releasing cellular molecules such as nucleic acid molecules (e.g., mRNAs). The cell may be lysed prior to partitioning and barcoding of cellular molecules or may be lysed in the partition. The cellular mRNA molecules may be reverse transcribed using nucleic acid molecules comprising a second barcode(e.g., cell-specific barcode sequence), thereby attaching the second barcode (e.g., cell-specific barcode), to the reversed transcribed nucleic acid molecules (and e.g., associating analytes of the cell with the cell-specific barcode).

Alternatively, cellular mRNA molecules may be first reverse transcribed into cDNA (e.g., using a poly-T containing primer) and the second, cell-specific barcode sequence attached (e.g., to the 5' end of an mRNA/cDNA molecule) using, e.g., a template switching reaction as described elsewhere herein. See, e.g., U.S. Pat. Pub. 2018/0105808, which is incorporated by reference in its entirety, for exemplary molecules and methods for analyzing and barcoding mRNA of single cells using template switching reactions and template switching oligonucleotides. In some instances, cellular barcodes are released from, e.g., a bead (such as a gel bead) into the partition as described elsewhere herein (e.g., using a stimulus, such as a reducing agent). Similarly, the nucleic acid molecules comprising a first, analyte-specific barcode sequence can be utilized to generate a molecule comprising the first analyte specific barcode and the second, cell-specific barcode. The nucleic acid molecules attached to an analyte specific binding agent, e.g. reporter agent, may comprise one or more functional sequences in addition to the analyte-specific barcode sequence. For example, the nucleic acid molecules attached to an analyte specific binding agent may comprise one or more of a unique molecular identifier (UMI), a primer sequence or primer binding sequence (e.g., a sequencing primer sequence (or partial sequencing primer sequence) such as an R1 and/or R2 sequence), a sequence configured to attach to the flow cell of a sequencer (e.g., P5 and/or P7), or sequence complementary to a sequence on a nucleic acid barcode molecule (e.g., attached to a bead, such as those described in FIG. 3). Accordingly, barcoded molecules (e.g., comprising an analyte specific and cell specific barcode), may also comprise these functional sequences.

Figure 7:
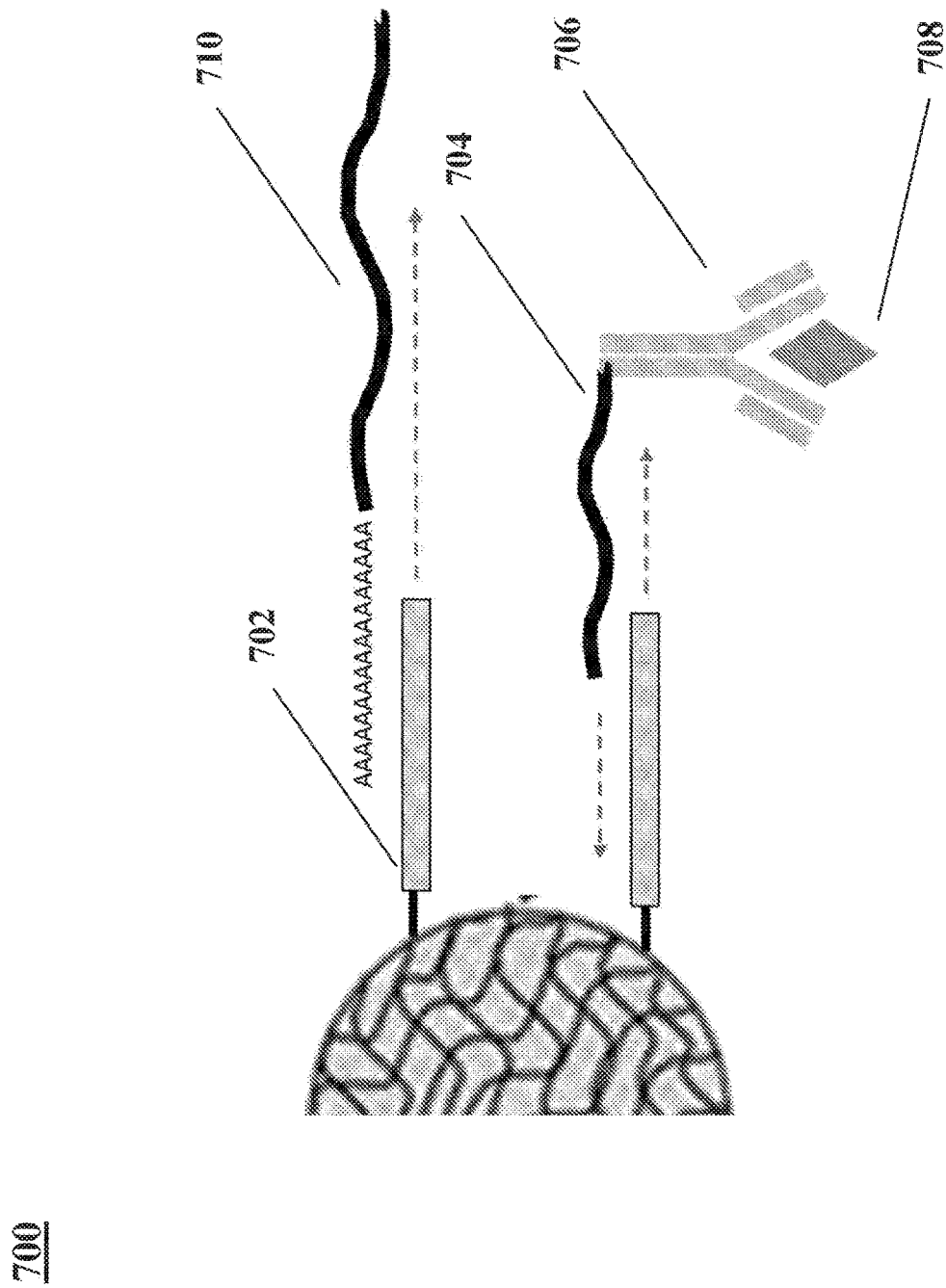
FIG. 7 shows an example of a barcoded bead that may be used in a partition such as a droplet to couple a barcode (e.g., a partition-specific barcode) and one or more analytes (e.g., an antibody bound to an antigen or epitope in a cell, mRNAs, etc.) of a single cell, thereby associating said one or more analytes with the single cell.
Figure 11:
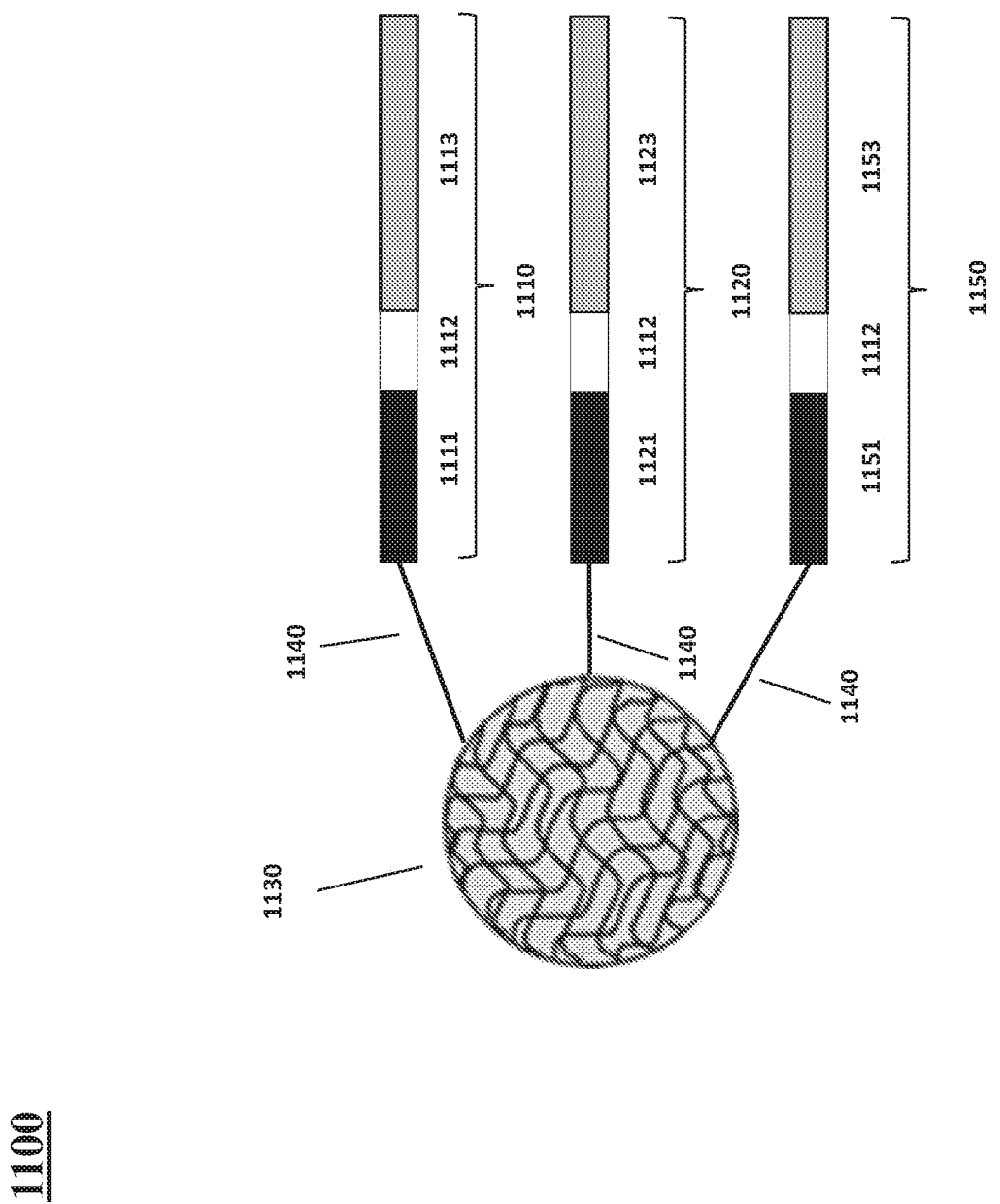
FIG. 11 depicts an example of a barcode carrying bead.

Once the contents of the cells are released into their respective partitions, the nucleic acids contained therein may be further processed within the partitions. In accordance with the methods and systems described herein, the nucleic acid contents of individual cells can be provided with unique identifiers such that, upon characterization of those nucleic acids they may be attributed as having been derived from the same cell or cells. The ability to attribute characteristics to individual cells or groups of cells is provided by the assignment of unique identifiers specifically to an individual cell or groups of cells. Unique identifiers, e.g., in the form of nucleic acid barcodes can be assigned or associated with individual cells or populations of cells, in order to tag or label the cell's components (and as a result, its characteristics) with the unique identifiers. These unique identifiers can then be used to attribute the cell's components and characteristics to an individual cell or group of cells. In some aspects, this is carried out by co-partitioning the individual cells or groups of cells with the unique identifiers. In some aspects, the unique identifiers are provided in the form of oligonucleotides (also referred to herein as anchor oligonucleotides) that comprise nucleic acid barcode sequences that may be attached to or otherwise associated with the nucleic acid contents of individual cells, or to other components of the cells, and particularly to fragments of those nucleic acids. The oligonucleotides may be partitioned such that as between oligonucleotides in a given partition, the nucleic acid barcode sequences contained therein are the same, but as between different partitions, the oligonucleotides can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present. FIG. 7 shows an example of a barcoded bead that may be used in a partition such as a droplet to couple a barcode 702 (e.g., a partition-specific barcode) and one or more analytes (e.g., an antibody bound to an binding partner in a cell, mRNAs, etc.) of a single cell, thereby associating said one or more analytes with the single cell. For instance, partition-specific barcode 702 can be coupled to an mRNA 710 (which may be a transcript from the expression system introduced into a cell for expression of a candidate binding partner 708). Another molecule of the same partition-specific barcode may be coupled to an antibody barcode 704 which corresponds to antibody 706 that binds to a candidate binding partner (e.g., an antigen or epitope) 708 that is present (e.g., expressed) in the same cell. FIG. 11 illustrates another example of a barcode carrying bead, as described in section VII-B.

Figure 9:
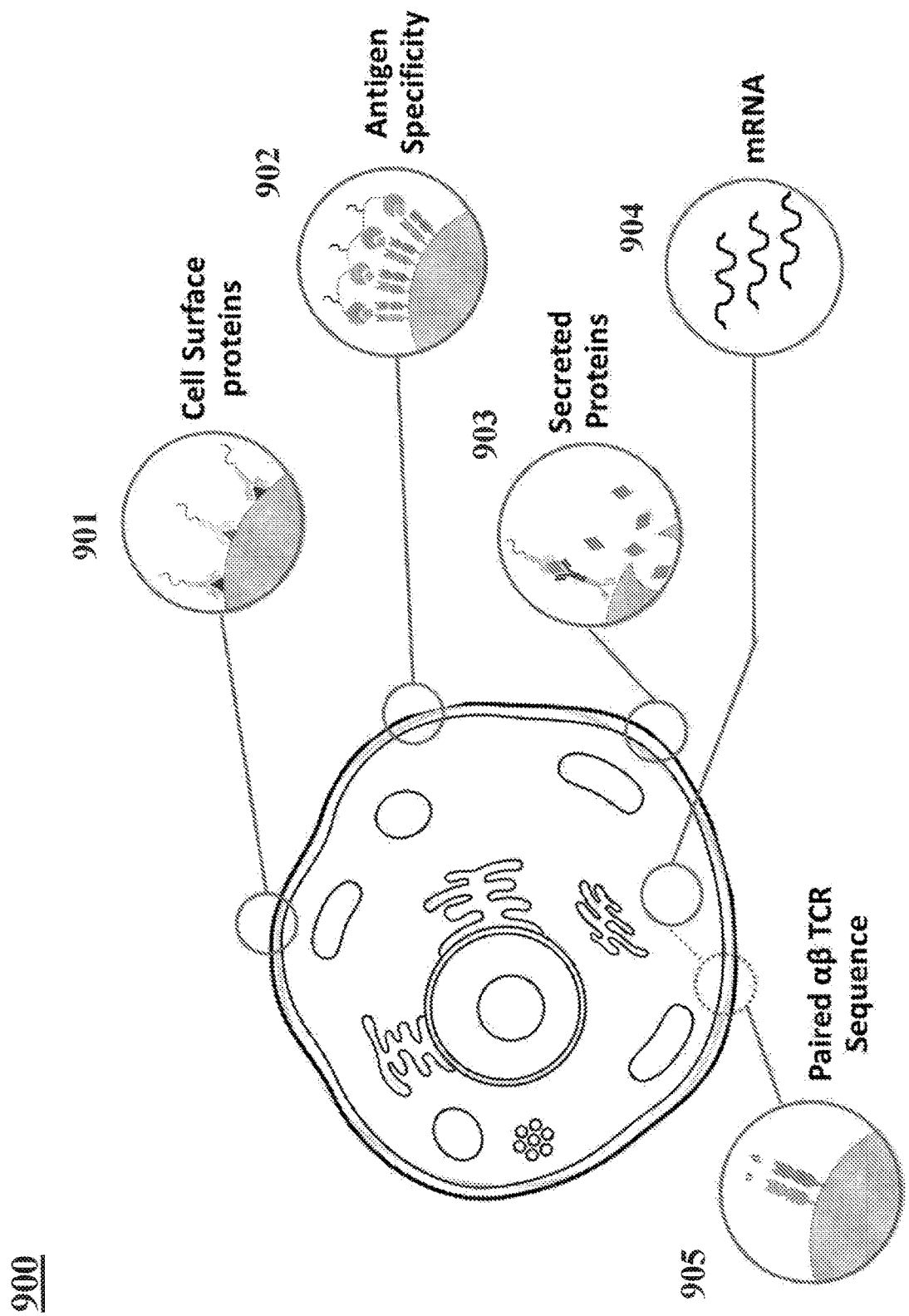
FIG. 9 shows an example of simultaneous measurement of secreted analysts, mRNAs, cell surface proteins, paired αβ T-cell receptor sequences, and antigen binding specificity.

Upon completion of the one or more barcoding, reverse transcription, and/or nucleic acid processing steps (e.g., depending on how many different analytes of a cell are being barcoded), the contents of the partitions (e.g., droplets or wells) may be pooled and the nucleic acid molecules subjected to further bulk processing and sequencing. Thus, the presently described methods and systems allow the association of multiple analytes (e.g., secreted antibodies or antigen binding fragment thereof) to a single cell, thereby enabling the measurement, analysis, and/or characterization of a plurality of cells at the single cell level. As described herein, the plurality of cells (e.g., one or more cell populations such as populations of immune cells, e.g., B cells or plasma cells) may be analyzed and characterized in an efficient and simultaneous manner. The methods disclosed herein not only allow analysis of cellular molecules after lysis of the cell, but also allow analysis of molecules that may be secreted by the cell (e.g., an immune cell such as a T cell, B cell, plasma cell, or dendritic cell) such as secreted proteins, antibodies, antigen binding fragments thereof, or cytokines, (see e.g., operation 903) in addition and/or simultaneous to the analysis of cellular nucleic acid molecules (e.g., mRNAs for analyzing expression or presence of the exogenous epitope in an engineered cell, see e.g., operations 904), cell surface proteins (e.g., receptors or ligands, etc., see e.g., operation 901), antigen presentation (e.g., antigen presentation by B cells), antigen specificity (see e.g., operation 902) of a single cell, antigen receptor sequences (see e.g., operation 905), etc., e.g., as shown in FIG. 9.

In embodiments where intracellular analytes (e.g., mRNA) are processed in parallel to secreted antibody or antigen binding fragment thereof, the cells contained in a partition (e.g., a droplet or a well) and cell beads contained in a partition (e.g., a droplet or a well), after cell beads are optionally dissolved (e.g., by dissolving the polymer matrix), are contacted with lysis reagents in order to release the contents of cells or viruses associated with the cell bead. In some cases, the lysis agents can be contacted with a cell bead suspension in bulk after cell bead formation. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), a surfactant based lysis solution (e.g., TritonX-100, Tween 20, sodium dodecyl sulfate (SDS)) for example, as well as other commercially available lysis enzymes. Electroporation, thermal, acoustic or mechanical cellular disruption may also be used in certain cases. In some cases, the cell bead matrix can be configured to give rise to a pore size that is sufficiently small to retain nucleic acid fragments of a particular size, following cellular disruption. In other instances, the cell bead matrix may be functionalized (e.g., covalently bound) with nucleic acid molecules (e.g., containing a poly-T sequence) configured to capture released analytes (e.g., mRNA, which optionally can be processed into cDNA prior to partitioning).

Other reagents can also be contacted with the cells, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated cell beads, the cell beads may be exposed to an appropriate stimulus to release the cell beads or their contents into, e.g., a partition. For example, in some cases, a chemical stimulus may be co-partitioned along with an encapsulated cell bead to allow for the degradation of the microcapsule and release of the cell or its contents into the larger partition. In some cases, this stimulus may be the same as the stimulus described elsewhere herein for release of oligonucleotides from their respective microcapsule (e.g., bead). In alternative aspects, this may be a different and non-overlapping stimulus, in order to allow an encapsulated cell bead release its contents into a partition at a different time from the release of oligonucleotides into the same partition.

After the releasing of cellular macromolecular constituent, the cellular mRNA molecules are subject to a reverse transcription reaction with other types of reverse transcription primers such that cDNA is generated from the mRNAs. In some cases, simultaneously, a partition-specific (e.g., cell-specific, such as those described in FIG. 3) barcode molecule is attached during cDNA generation. In certain embodiments, the partition-specific (e.g., cell-specific) barcode sequence is a DNA oligonucleotide. The partition-specific (e.g., cell-specific) barcode sequence may be a second barcode sequence that is different from a first barcode sequence (e.g., analyte-specific barcode) attached to or coupled to a second binding reporter agent used to barcode an analyte that is secreted from a cell (e.g., an immune cell such as a B cell).

Alternatively, cellular mRNA molecules may be first reverse transcribed into cDNA (e.g., using a poly-T containing primer) and the second, cell-specific barcode sequence attached (e.g., to the 5' end of an mRNA/cDNA molecule) using, e.g., a template switching reaction as described elsewhere herein. See, e.g., U.S. Pat. Pub. 2018/0105808, which is incorporated by reference in its entirety, for exemplary molecules and methods for analyzing and barcoding mRNA of single cells using template switching reactions and template switching oligonucleotides.

In certain embodiments, the partition-specific (e.g., cell-specific) barcode molecules (e.g., oligonucleotides, nucleic acid molecules) are releasable from the beads upon the application of a particular stimulus to the beads, as described elsewhere herein. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules from the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some embodiments, barcode molecules attached to reporter agent (e.g., an analyte specific polypeptide, such as an antigen) bound to an analyte may be released (e.g., through a releasable linkage/labile bound as described elsewhere herein). Similarly, in some embodiments, barcode molecules attached to MEW multimers and/or attached to cell surface protein specific antibodies may also be released (e.g., through a releasable linkage/labile bound as described elsewhere herein). Partition-specific (e.g., droplet-specific or secondary) barcode sequences may be attached to any or all of these released barcode molecules (or derivatives thereof). For example, a barcoded bead comprising a partition specific barcode sequence may be used in a partition such as a droplet to couple a barcode (e.g., a partition-specific barcode) to one or more analytes (e.g., secreted cytokines, mRNAs, etc) of a single cell, thereby associating said one or more analytes with the single cell. These barcodes are used as cell and/or partition-specific identifiers for RNA, DNA, proteins, secreted antibodies or antigen binding fragments thereof, and/or antigens that used to stimulate the cells. The assignment of unique barcodes specifically to an individual biological particle or groups of biological particles can attribute characteristics to individual biological particles or groups of biological particles. Unique identifiers, e.g., in the form of nucleic acid barcodes, are assigned or associated with individual biological particles or populations of biological particles, in order to tag or label the biological particle's macromolecular components (and as a result, its characteristics) with the unique identifiers. These unique identifiers, e.g., barcodes, can then be used to attribute the biological particle's components and characteristics to an individual biological particle or group of biological particles. Furthermore, as described elsewhere herein, in addition to cell and/or partition specific barcodes, unique molecular identifiers (UMIs) can also be added to cellular analytes (e.g., mRNA molecules) and reporter molecules (e.g., attached to binding agents, or reporter molecules attached to MEW molecules/multimers and/or antibodies, such as cell surface antibodies) to provide a unique identifier for quantitation of individual molecules.

Figure 8:
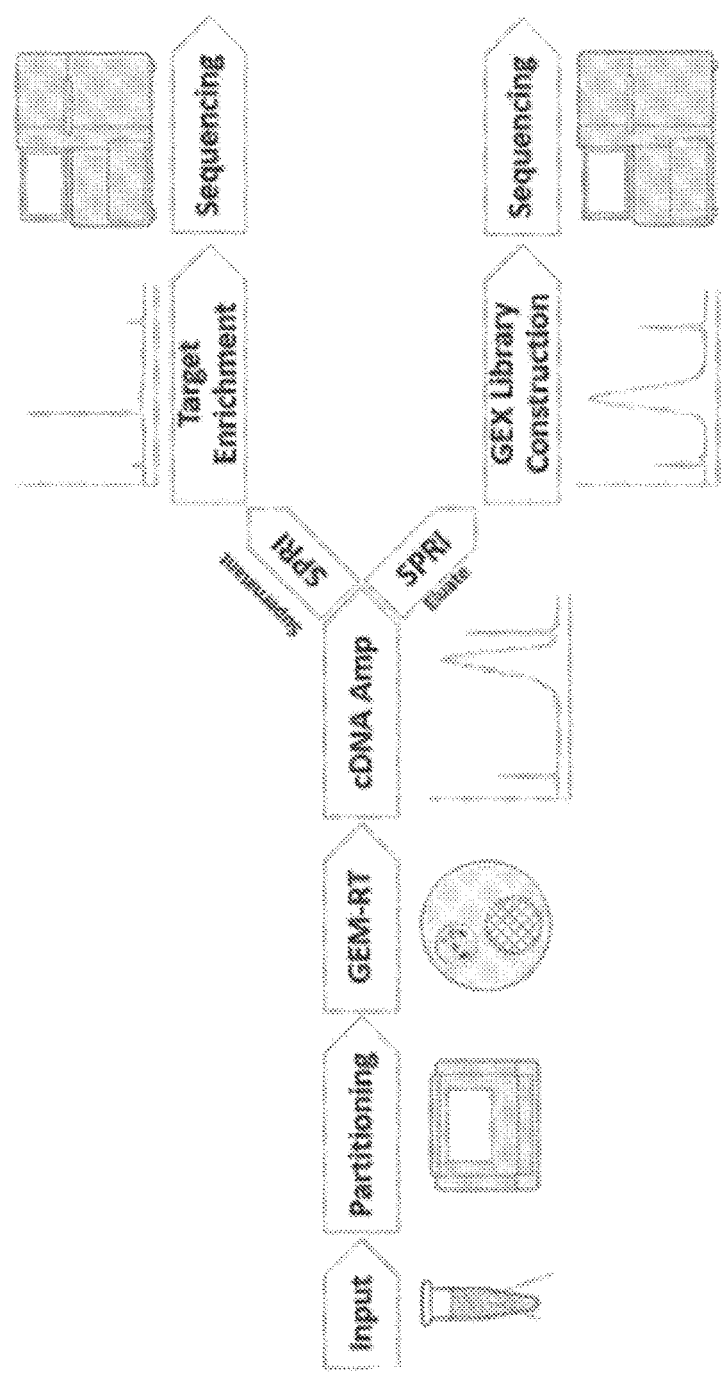
FIG. 8 shows an illustration of the conversion of barcoded analytes into sequencing libraries.

Barcoded partition contents can be pooled into a bulk solution and further processed as described elsewhere herein to generate a sequencing library (see, e.g. FIG. 8). For example, following partitioning into Gel Bead-in-Emulsion (GEM), the cell in each droplet may be lysed and reverse transcription (GEM-RT) may be performed. After cDNA amplification, the supernatant and eluate are subjected to Solid Phase Reversible Immobilization (SPRI) followed by enrichment and library construction, respectively. Referring to FIG. 9, information regarding secreted antibodies, cytokines, as well as other analytes, such as mRNAs, cell surface proteins, and antigen binding specificity can all be analyzed and attributed to the same cell using the cell-specific barcode (see, e.g., FIG. 3 or FIG. 4).

B. Multiplexing Methods

The present disclosure provides methods and systems for multiplexing, and otherwise increasing throughput of samples for analysis. For example, a single or integrated process workflow may permit the processing, identification, and/or analysis of more or multiple analytes, more or multiple types of analytes, and/or more or multiple types of analyte characterizations. For example, in the methods and systems described herein, one or more labelling agents capable of binding to or otherwise coupling to one or more cells or cell features may be used to characterize cells and/or cell features. In some instances, cell features include cell surface features. Cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof. A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have a first reporter oligonucleotide coupled thereto, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, each of which is herein entirely incorporated by reference for all purposes.

In a particular example, a library of potential cell feature labelling agents may be provided, where the respective cell feature labelling agents are associated with nucleic acid reporter molecules, such that a different reporter oligonucleotide sequence is associated with each labelling agent capable of binding to a specific cell feature. In other aspects, different members of the library may be characterized by the presence of a different oligonucleotide sequence label. For example, an antibody capable of binding to a first protein may have associated with it a first reporter oligonucleotide sequence, while an antibody capable of binding to a second protein may have a different reporter oligonucleotide sequence associated with it. The presence of the particular oligonucleotide sequence may be indicative of the presence of a particular antibody or cell feature which may be recognized or bound by the particular antibody.

Labelling agents capable of binding to or otherwise coupling to one or more cells may be used to characterize a cell as belonging to a particular set of cells. For example, labeling agents may be used to label a sample of cells or a group of cells. In this way, a group of cells may be labeled as different from another group of cells. In an example, a first group of cells may originate from a first sample and a second group of cells may originate from a second sample. Labelling agents may allow the first group and second group to have a different labeling agent (or reporter oligonucleotide associated with the labeling agent). This may, for example, facilitate multiplexing, where cells of the first group and cells of the second group may be labeled separately and then pooled together for downstream analysis. The downstream detection of a label may indicate analytes as belonging to a particular group.

For example, a reporter oligonucleotide may be linked to an antibody or an epitope binding fragment thereof, and labeling a cell may comprise subjecting the antibody linked to the reporter oligonucleotide, e.g., antibody-linked barcode molecule, or the epitope linked to the reporter oligonucleotide, e.g, epitope binding fragment-linked barcode molecule, to conditions suitable for binding the antibody to a molecule present on a surface of the cell. The binding affinity between the antibody or the epitope binding fragment thereof and the molecule present on the surface may be within a desired range to ensure that the antibody or the epitope binding fragment thereof remains bound to the molecule. For example, the binding affinity may be within a desired range to ensure that the antibody or the epitope binding fragment thereof remains bound to the molecule during various sample processing steps, such as partitioning and/or nucleic acid amplification or extension. A dissociation constant (Kd) between the antibody or an epitope binding fragment thereof and the molecule to which it binds may be less than about 100 µM, 90 µM, 80 µM, 70 µM, 60 µM, 50 µM, 40 µM, 30 µM, 20 µM, 10 µM, 9 µM, 8 µM, 7 µM, 6 µM, 5 µM, 4 µM, 3 µM, 2 µM, 1 µM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 900 pM, 800 pM, 700 pM, 600 pM, 500 pM, 400 pM, 300 pM, 200 pM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM, or 1 pM. For example, the dissociation constant may be less than about 10 µM.

In another example, a reporter oligonucleotide may be coupled to a cell-penetrating peptide (CPP), and labeling cells may comprise delivering the CPP coupled to the reporter oligonucleotice, e.g., CPP coupled reporter oligonucleotide, into an analyte carrier. Labeling analyte carriers may comprise delivering the CPP conjugated oligonucleotide into a cell and/or cell bead by the cell-penetrating peptide. A CPP that can be used in the methods provided herein can comprise at least one non-functional cysteine residue, which may be either free or derivatized to form a disulfide link with an oligonucleotide that has been modified for such linkage. Non-limiting examples of CPPs that can be used in embodiments herein include penetratin, transportan, plsl, TAT(48-60), pVEC, MTS, and MAP. Cell-penetrating peptides useful in the methods provided herein can have the capability of inducing cell penetration for at least about 30%, 40%, 50%, 60%, 70%, 80%, 90%, 95%, 96%, 97%, 98%, 99%, or 100% of cells of a cell population. The CPP may be an arginine-rich peptide transporter. The CPP may be Penetratin or the Tat peptide. In another example, a reporter oligonucleotide may be coupled to a fluorophore or dye, and labeling cells may comprise subjecting the reporter oligonucleotide coupled to the fluorophore, e.g, fluorophore-linked barcode molecule, to conditions suitable for binding the fluorophore to the surface of the cell. In some instances, fluorophores can interact strongly with lipid bilayers and labeling cells may comprise subjecting the fluorophore-linked barcode molecule to conditions such that the fluorophore binds to or is inserted into a membrane of the cell. In some cases, the fluorophore is a water-soluble, organic fluorophore. In some instances, the fluorophore is Alexa 532 maleimide, tetramethylrhodamine-5-maleimide (TMR maleimide), BODIPY-TMR maleimide, Sulfo-Cy3 maleimide, Alexa 546 carboxylic acid/succinimidyl ester, Atto 550 maleimide, Cy3 carboxylic acid/succinimidyl ester, Cy3B carboxylic acid/succinimidyl ester, Atto 565 biotin, Sulforhodamine B, Alexa 594 maleimide, Texas Red maleimide, Alexa 633 maleimide, Abberior STAR 635P azide, Atto 647N maleimide, Atto 647 SE, or Sulfo-Cy5 maleimide. See, e.g., Hughes L D, et al. PLoS One. 2014 Feb. 4; 9(2):e87649, which is hereby incorporated by reference in its entirety for all purposes, for a description of organic fluorophores.

A reporter oligonucleotide may be coupled to a lipophilic molecule, and labeling cells may comprise delivering the reporter oligonucleotide, e.g, nucleic acid barcode molecule, to a membrane of a cell or a nuclear membrane by the lipophilic molecule. Lipophilic molecules can associate with and/or insert into lipid membranes such as cell membranes and nuclear membranes. In some cases, the insertion can be reversible. In some cases, the association between the lipophilic molecule and the cell or nuclear membrane may be such that the membrane retains the lipophilic molecule (e.g., and associated components, such as nucleic acid barcode molecules, thereof) during subsequent processing (e.g., partitioning, cell permeabilization, amplification, pooling, etc.). The reporter nucleotide may enter into the intracellular space and/or a cell nucleus. In one embodiment, a reporter oligonucleotide coupled to a lipophilic molecule will remain associated with and/or inserted into lipid membrane (as described herein) via the lipophilic molecule until lysis of the cell occurs, e.g., inside a partition.

A reporter oligonucleotide may be part of a nucleic acid molecule comprising any number of functional sequences, as described elsewhere herein, such as a target capture sequence, a random primer sequence, and the like, and coupled to another nucleic acid molecule that is, or is derived from, the analyte.

Prior to partitioning, the cells may be incubated with the library of labelling agents, that may be labelling agents to a broad panel of different cell features, e.g., receptors, proteins, etc., and which include their associated reporter oligonucleotides. Unbound labelling agents may be washed from the cells, and the cells may then be co-partitioned (e.g., into droplets or wells) along with partition-specific barcode oligonucleotides (e.g., attached to a support, such as a bead or gel bead) as described elsewhere herein. As a result, the partitions may include the cell or cells, as well as the bound labelling agents and their known, associated reporter oligonucleotides.

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide. For example, the first plurality of the labeling agent and second plurality of the labeling agent may interact with different cells, cell populations or samples, allowing a particular report oligonucleotide to indicate a particular cell population (or cell or sample) and cell feature. In this way, different samples or groups can be independently processed and subsequently combined together for pooled analysis (e.g., partition-based barcoding as described elsewhere herein). See, e.g., U.S. Pat. Pub. 20190323088, which is hereby entirely incorporated by reference for all purposes.

As described elsewhere herein, libraries of labelling agents may be associated with a particular cell feature as well as be used to identify analytes as originating from a particular cell population, or sample. Cell populations may be incubated with a plurality of libraries such that a cell or cells comprise multiple labelling agents. For example, a cell may comprise coupled thereto a lipophilic labeling agent and an antibody. The lipophilic labeling agent may indicate that the cell is a member of a particular cell sample, whereas the antibody may indicate that the cell comprises a particular analyte. In this manner, the reporter oligonucleotides and labelling agents may allow multi-analyte, multiplexed analyses to be performed.

In some instances, these reporter oligonucleotides may comprise nucleic acid barcode sequences that permit identification of the labelling agent which the reporter oligonucleotide is coupled to. The use of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to an oligonucleotide that is complementary to a sequence of the reporter oligonucleotide, and the oligonucleotide may be allowed to hybridize to the reporter oligonucleotide.

Figure 10:
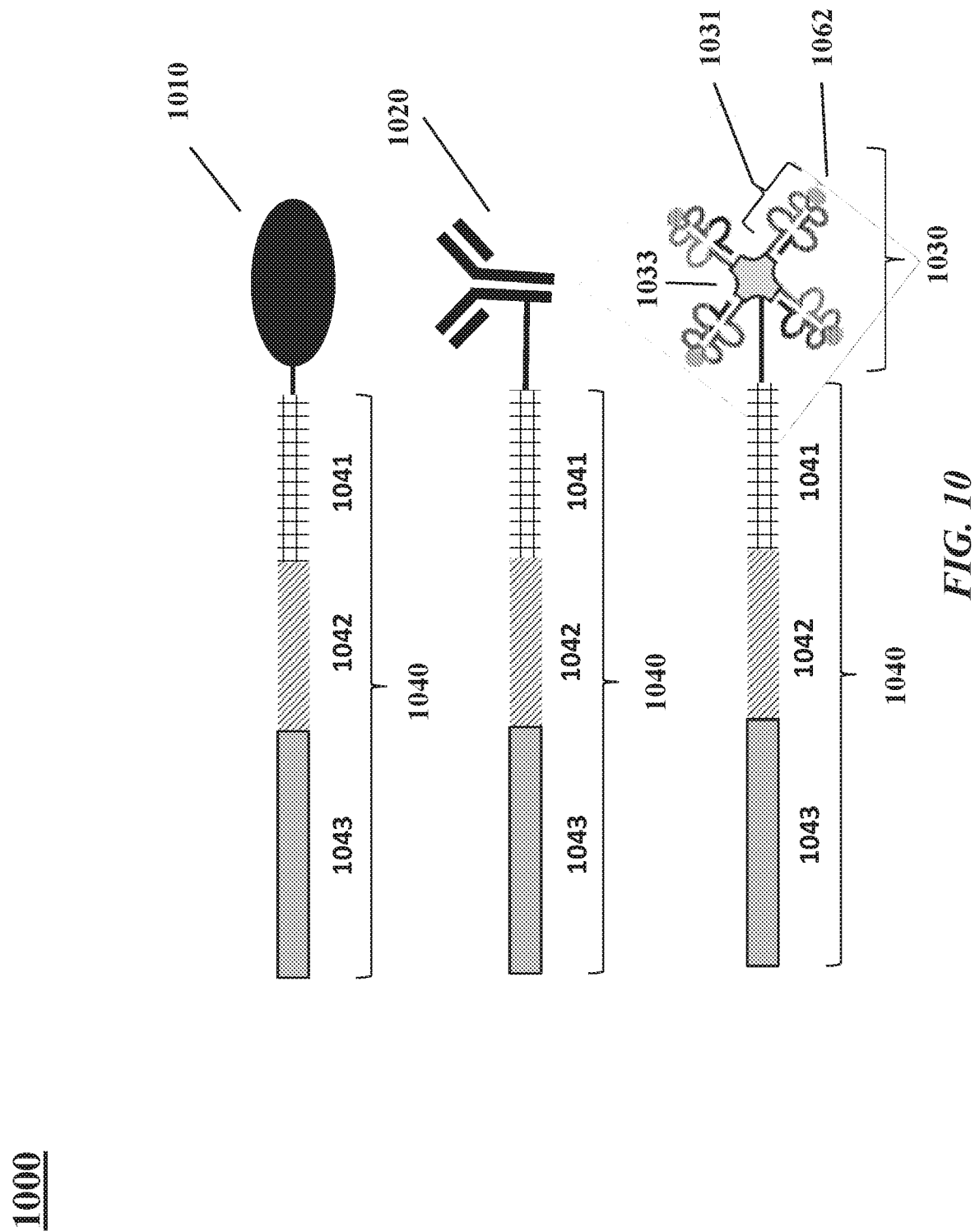
FIG. 10 schematically illustrates examples of labelling agents.

FIG. 10 describes exemplary labelling agents (1010, 1020, 1030) comprising reporter oligonucleotides (1040) attached thereto. Labelling agent 1010 (e.g., any of the labelling agents described herein) is attached (either directly, e.g., covalently attached, or indirectly) to reporter oligonucleotide 1040. Reporter oligonucleotide 1040 may comprise reporter barcode sequence 1042 that identifies labelling agent 1010. Reporter oligonucleotide 1040 may also comprise one or more functional sequences 1043 that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, or a sequencing primer or primer biding sequence (such as an R1, R2, or partial R1 or R2 sequence).

Referring to FIG. 10, in some instances, reporter oligonucleotide 1040 conjugated to a labelling agent (e.g., 1010, 1020, 1030) comprises a primer sequence 1041, a reporter barcode sequence 1042 that identifies the labelling agent (e.g., 1010, 1020, 1030), and functional sequence 1043. Functional sequence 1043 may be configured to hybridize to a complementary sequence, such as a complementary sequence present on a nucleic acid barcode molecule 1090 (not shown), such as those described elsewhere herein. In some instances, nucleic acid barcode molecule 1090 is attached to a support (e.g., a bead, such as a gel bead), such as those described elsewhere herein. For example, nucleic acid barcode molecule 1090 may be attached to the support via a releasable linkage (e.g., comprising a labile bond), such as those described elsewhere herein. In some instances, reporter oligonucleotide 1040 comprises one or more additional functional sequences, such as those described above.

In some instances, the labelling agent 1010 is a protein or polypeptide (e.g., an antigen or prospective antigen) comprising reporter oligonucleotide 1040. Reporter oligonucleotide 1040 comprises reporter barcode sequence 1042 that identifies polypeptide 1010 and can be used to infer the presence of an analyte, e.g., a binding partner of polypeptide 1010 (i.e., a molecule or compound to which polypeptide 1010 can bind). In some instances, the labelling agent 1010 is a lipophilic moiety (e.g., cholesterol) comprising reporter oligonucleotide 1040, where the lipophilic moiety is selected such that labelling agent 1010 integrates into a membrane of a cell or nucleus. Reporter oligonucleotide 1040 comprises reporter barcode sequence 1042 that identifies lipophilic moiety 1010 which in some instances is used to tag cells (e.g., groups of cells, cell samples, etc.) and may be used for multiplex analyses as described elsewhere herein. In some instances, the labelling agent is an antibody 1020 (or an epitope binding fragment thereof) comprising reporter oligonucleotide 1040. Reporter oligonucleotide 1040 comprises reporter barcode sequence 1042 that identifies antibody 1020 (e.g., an antibody barcode sequence) and can be used to infer the presence of, e.g., a target of antibody 1020 (i.e., a molecule or compound to which antibody 1020 binds). In other embodiments, labelling agent 1030 comprises an MHC molecule 1031 comprising peptide 1032 and reporter oligonucleotide 1040 that identifies peptide 1032. In some instances, the MHC molecule is coupled to a support 1033. In some instances, support 1033 may be a polypeptide, such as streptavidin, or a polysaccharide, such as dextran. In some instances, reporter oligonucleotide 1040 may be directly or indirectly coupled to MHC labelling agent 1030 in any suitable manner. For example, reporter oligonucleotide 1040 may be coupled to MHC molecule 1031, support 1033, or peptide 1032. In some embodiments, labelling agent 1030 comprises a plurality of MHC molecules, (e.g. is an MHC multimer, which may be coupled to a support (e.g., 1033)). There are many possible configurations of Class I and/or Class II MHC multimers that can be utilized with the compositions, methods, and systems disclosed herein, e.g., MHC tetramers, MHC pentamers (MHC assembled via a coiled-coil domain, e.g., Pro5® MHC Class I Pentamers, (ProImmune, Ltd.), MHC octamers, MHC dodecamers, MHC decorated dextran molecules (e.g., MHC Dextramer® (Immudex)), etc. For a description of exemplary labelling agents, including antibody and MHC-based labelling agents, reporter oligonucleotides, and methods of use, see, e.g., U.S. Pat. No. 10,550,429 and U.S. Pat. Pub. 20190367969, each of which is herein entirely incorporated by reference for all purposes.

FIG. 11 illustrates another example of a barcode carrying bead. In some embodiments, analysis of multiple analytes (e.g., RNA and one or more analytes using labelling agents described herein) may comprise using nucleic acid barcode molecules as generally depicted in FIG. 11. In some embodiments, nucleic acid barcode molecules 1110 and 1120 are attached to support 1130 via a releasable linkage 1140 (e.g., comprising a labile bond) as described elsewhere herein. Nucleic acid barcode molecule 1110 may comprise adapter sequence 1111, barcode sequence 1112 and adapter sequence 1113. Nucleic acid barcode molecule 1120 may comprise adapter sequence 1121, barcode sequence 1112, and adapter sequence 1123, wherein adapter sequence 1123 comprises a different sequence than adapter sequence 1113. In some instances, adapter 1111 and adapter 1121 comprise the same sequence. In some instances, adapter 1111 and adapter 1121 comprise different sequences. Although support 1130 is shown comprising nucleic acid barcode molecules 1110 and 1120, any suitable number of barcode molecules comprising common barcode sequence 1112 are contemplated herein. For example, in some embodiments, support 1130 further comprises nucleic acid barcode molecule 1150. Nucleic acid barcode molecule 1150 may comprise adapter sequence 1151, barcode sequence 1112 and adapter sequence 1153, wherein adapter sequence 1153 comprises a different sequence than adapter sequence 1113 and 1123. In some instances, nucleic acid barcode molecules (e.g., 1110, 1120, 1150) comprise one or more additional functional sequences, such as a UMI or other sequences described herein. The nucleic acid barcode molecules 1110, 1120 or 1150 may interact with analytes as described elsewhere herein, for example, as depicted in FIGS. 12A-C.

Referring to FIG. 12A, in an instance where cells are labelled with labeling agents, capture sequence 1223 may be complementary to a capture handle sequence of a reporter oligonucleotide. Cells may be contacted with one or more reporter oligonucleotide 1220 conjugated labelling agents 1210 (e.g., polypeptide, antibody, or others described elsewhere herein). In some cases, the cells may be further processed prior to barcoding. For example, such processing steps may include one or more washing and/or cell sorting steps. In some instances, a cell that is bound to labelling agent 1210 which is conjugated to oligonucleotide 1220 and support 1230 (e.g., a bead, such as a gel bead) comprising nucleic acid barcode molecule 1290 is partitioned into a partition amongst a plurality of partitions (e.g., a droplet of a droplet emulsion or a well of a microwell array). In some instances, the partition comprises at most a single cell bound to labelling agent 1210. In some instances, reporter oligonucleotide 1220 conjugated to labelling agent 1210 (e.g., polypeptide, an antibody, pMHC molecule such as an MHC multimer, etc.) comprises a first adapter sequence 1211 (e.g., a primer sequence), a barcode sequence 1212 that identifies the labelling agent 1210 (e.g., the polypeptide, antibody, or peptide of a pMHC molecule or complex), and a capture handle sequence 1213. Capture handle sequence 1213 may be configured to hybridize to a complementary sequence, such as a capture sequence 1223 present on a nucleic acid barcode molecule 1290. In some instances, oligonucleotide 1220 comprises one or more additional functional sequences, such as those described elsewhere herein.

Figure 12C:
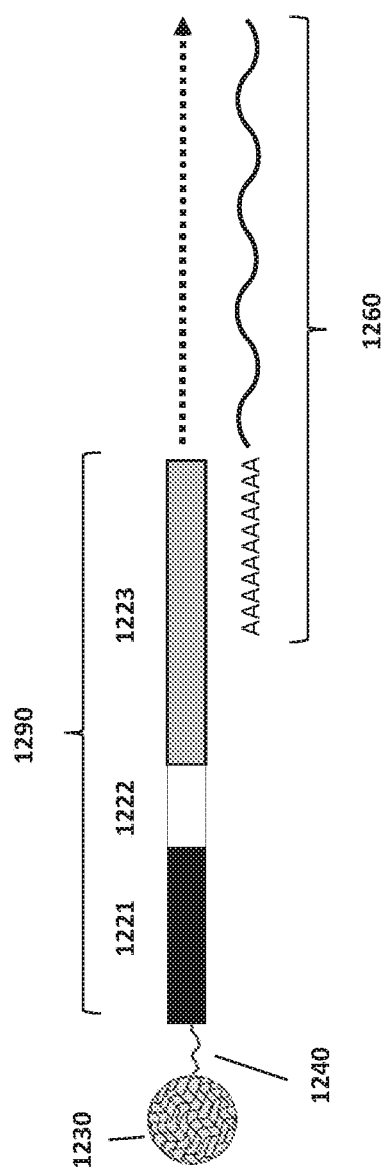
FIG. 12 A-C schematically depict an example workflow for processing nucleic acid molecules.

Barcoded nucleic acid molecules may be generated (e.g., via a nucleic acid reaction, such as nucleic acid extension or ligation) from the constructs described in FIGS. 12A-C. For example, sequence 1213 may then be hybridized to complementary sequence 1223 to generate (e.g., via a nucleic acid reaction, such as nucleic acid extension or ligation) a barcoded nucleic acid molecule comprising cell (e.g., partition specific) barcode sequence 1222 (or a reverse complement thereof) and reporter sequence 1212 (or a reverse complement thereof). Barcoded nucleic acid molecules can then be optionally processed as described elsewhere herein, e.g., to amplify the molecules and/or append sequencing platform specific sequences to the fragments. See, e.g., U.S. Pat. Pub. 2018/0105808, which is hereby entirely incorporated by reference for all purposes. Barcoded nucleic acid molecules, or derivatives generated therefrom, can then be sequenced on a suitable sequencing platform.

In some instances, analysis of multiple analytes (e.g., nucleic acids and one or more analytes using labelling agents described herein) may be performed. For example, the workflow may comprise a workflow as generally depicted in any of FIGS. 12A-C, or a combination of workflows for an individual analyte, as described elsewhere herein. For example, by using a combination of the workflows as generally depicted in FIGS. 12A-C, multiple analytes can be analyzed.

In some instances, analysis of an analyte (e.g. a nucleic acid, a polypeptide, a carbohydrate, a lipid, etc.) comprises a workflow as generally depicted in FIG. 12A. A nucleic acid barcode molecule 1290 may be co-partitioned with the one or more analytes. In some instances, nucleic acid barcode molecule 1290 is attached to a support 1230 (e.g., a bead, such as a gel bead), such as those described elsewhere herein. For example, nucleic acid barcode molecule 1290 may be attached to support 1230 via a releasable linkage 1240 (e.g., comprising a labile bond), such as those described elsewhere herein. Nucleic acid barcode molecule 1290 may comprise a barcode sequence 1221 and optionally comprise other additional sequences, for example, a UMI sequence 1222 (or other functional sequences described elsewhere herein). The nucleic acid barcode molecule 1290 may comprise a sequence 1223 that may be complementary to another nucleic acid sequence, such that it may hybridize to a particular sequence.

For example, sequence 1223 may comprise a poly-T sequence and may be used to hybridize to mRNA. Referring to FIG. 12C, in some embodiments, nucleic acid barcode molecule 1290 comprises sequence 1223 complementary to a sequence of RNA molecule 1260 from a cell. In some instances, sequence 1223 comprises a sequence specific for an RNA molecule. Sequence 1223 may comprise a known or targeted sequence or a random sequence. In some instances, a nucleic acid extension reaction may be performed, thereby generating a barcoded nucleic acid product comprising sequence 1223, the functional sequence 1221, common barcode sequence 1222, any other functional sequence, and a sequence corresponding to the RNA molecule 1260.

In another example, sequence 1223 may be complementary to an overhang sequence or an adapter sequence that has been appended to an analyte. For example, referring to FIG. 12B, in some embodiments, primer 1250 comprises a sequence complementary to a sequence of nucleic acid molecule 1260 (such as an RNA encoding for a BCR sequence) from an analyte carrier. In some instances, primer 1250 comprises one or more sequences 1251 that are not complementary to RNA molecule 1260. Sequence 1251 may be a functional sequence as described elsewhere herein, for example, an adapter sequence, a sequencing primer sequence, or a sequence the facilitates coupling to a flow cell of a sequencer. In some instances, primer 1250 comprises a poly-T sequence. In some instances, primer 1250 comprises a sequence complementary to a target sequence in an RNA molecule. In some instances, primer 1250 comprises a sequence complementary to a region of an immune molecule, such as the constant region of a TCR or BCR sequence. Primer 1250 is hybridized to nucleic acid molecule 1260 and complementary molecule 1270 is generated. For example, complementary molecule 1270 may be cDNA generated in a reverse transcription reaction. In some instances, an additional sequence may be appended to complementary molecule 1270. For example, the reverse transcriptase enzyme may be selected such that several non-templated bases 1280 (e.g., a poly-C sequence) are appended to the cDNA. In another example, a terminal transferase may also be used to append the additional sequence. Nucleic acid barcode molecule 1290 comprises a sequence 1224 complementary to the non-templated bases, and the reverse transcriptase performs a template switching reaction onto nucleic acid barcode molecule 1290 to generate a barcoded nucleic acid molecule comprising cell (e.g., partition specific) barcode sequence 1222 (or a reverse complement thereof) and a sequence of complementary molecule 1270 (or a portion thereof). In some instances, sequence 1223 comprises a sequence complementary to a region of an immune molecule, such as the constant region of a TCR or BCR sequence. Sequence 1223 is hybridized to nucleic acid molecule 1260 and a complementary molecule 1270 is generated. For example, complementary molecule 1270 may be generated in a reverse transcription reaction generating a barcoded nucleic acid molecule comprising cell (e.g., partition specific) barcode sequence 1222 (or a reverse complement thereof) and a sequence of complementary molecule 1270 (or a portion thereof). Additional methods and compositions suitable for barcoding cDNA generated from mRNA transcripts including those encoding V(D)J regions of an immune cell receptor and/or barcoding methods and composition including a template switch oligonucleotide are described in International Patent Application WO2018/075693, U.S. Patent Publication No. 2018/0105808, U.S. Patent Publication No. 2015/0376609, filed Jun. 26, 2015, and U.S. Patent Publication No. 2019/0367969, each of which applications is herein entirely incorporated by reference for all purposes.

C. Computer Systems

Figure 13:
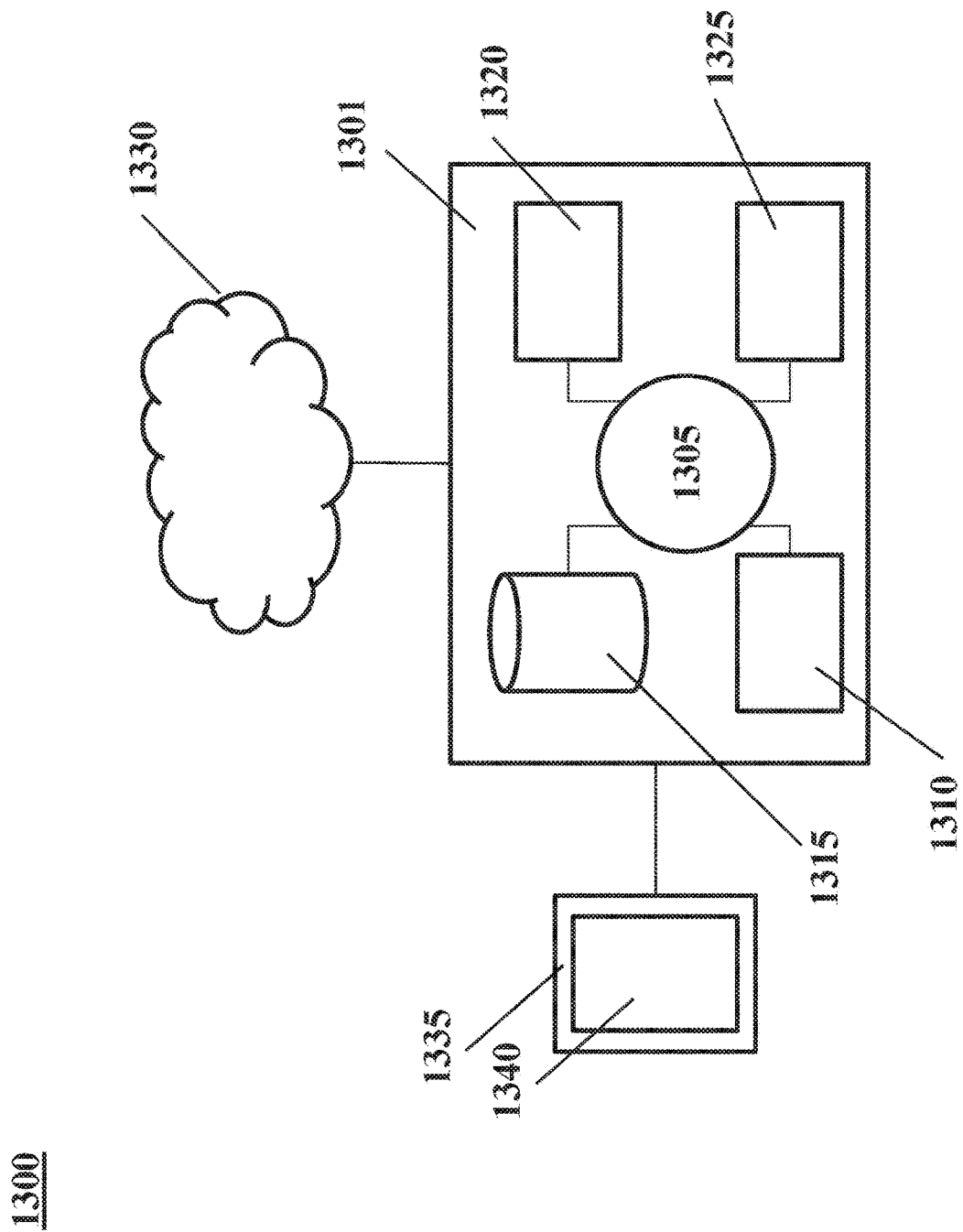
FIG. 13 shows a computer system that is programmed or otherwise configured to implement methods provided herein.

The present disclosure provides computer systems that are programmed to implement methods of the disclosure. FIG. 13 shows a computer system 1301 that is programmed or otherwise configured to (i) control a microfluidics system (e.g., fluid flow), (ii) sort occupied droplets from unoccupied droplets, (iii) polymerize droplets, (iv) partition cell beads or cells into partitions (e.g., droplets or wells), (v) lysate cells and cell beads, (vi) perform sequencing applications, (vii) generate and maintain libraries of cytokine or other analyte specific antibody barcode sequences, WIC multimer barcode sequences, cell surface protein barcode sequences, and cDNAs generated from mRNAs respectively (vi) analyze such libraries. The computer system 1301 can regulate various aspects of the present disclosure, such as, for example, regulating fluid flow rate in one or more channels in a microfluidic structure, regulating polymerization application units, regulating sequence application unit, etc. The computer system 1301 can be an electronic device of a user or a computer system that is remotely located with respect to the electronic device. The electronic device can be a mobile electronic device.

The computer system 1301 includes a central processing unit (CPU, also "processor" and "computer processor" herein) 1305, which can be a single core or multi core processor, or a plurality of processors for parallel processing. The computer system 1301 also includes memory or memory location 1310 (e.g., random-access memory, read-only memory, flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 can be a data storage unit (or data repository) for storing data. The computer system 1301 can be operatively coupled to a computer network ("network") 1330 with the aid of the communication interface 1320. The network 1330 can be the Internet, an internet and/or extranet, or an intranet and/or extranet that is in communication with the Internet. The network 1330 in some cases is a telecommunication and/or data network. The network 1330 can include one or more computer servers, which can enable distributed computing, such as cloud computing. The network 1330, in some cases with the aid of the computer system 1301, can implement a peer-to-peer network, which may enable devices coupled to the computer system 1301 to behave as a client or a server.

The CPU 1305 can execute a sequence of machine-readable instructions, which can be embodied in a program or software. The instructions may be stored in a memory location, such as the memory 1310. The instructions can be directed to the CPU 1305, which can subsequently program or otherwise configure the CPU 1305 to implement methods of the present disclosure. Examples of operations performed by the CPU 1305 can include fetch, decode, execute, and writeback.

The CPU 1305 can be part of a circuit, such as an integrated circuit. One or more other components of the system 1301 can be included in the circuit. In some cases, the circuit is an application specific integrated circuit (ASIC).

The storage unit 1315 can store files, such as drivers, libraries and saved programs. The storage unit 1315 can store user data, e.g., user preferences and user programs. The computer system 1301 in some cases can include one or more additional data storage units that are external to the computer system 1301, such as located on a remote server that is in communication with the computer system 1301 through an intranet or the Internet.

The computer system 1301 can communicate with one or more remote computer systems through the network 1330. For instance, the computer system 1301 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1301 via the network 1330.

Methods as described herein can be implemented by way of machine (e.g., computer processor) executable code stored on an electronic storage location of the computer system 1301, such as, for example, on the memory 1310 or electronic storage unit 1315. The machine executable or machine readable code can be provided in the form of software. During use, the code can be executed by the processor 1305. In some cases, the code can be retrieved from the storage unit 1315 and stored on the memory 1310 for ready access by the processor 1305. In some situations, the electronic storage unit 1315 can be precluded, and machine-executable instructions are stored on memory 1310.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1301 can include or be in communication with an electronic display 1335 that comprises a user interface (UI) 1340 for providing, for example, results of sequencing analysis, etc. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1305. The algorithm can, for example, perform nucleotide sequence amplification, sequencing sorting based on barcode sizes, sequencing amplified barcode sequences, analyzing sequencing data, etc.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

VIII. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the term "antigen binding molecule" refers in its broadest sense to a molecule that specifically binds an antigenic determinant. Examples of antigen binding molecules are immunoglobulins and derivatives, e.g. fragments, thereof.

The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

The term "antibody" herein is used in the broadest sense and encompasses various antibody structures, including but not limited to monoclonal antibodies, polyclonal antibodies, and antibody fragments so long as they exhibit the desired antigen-binding activity.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The terms "polynucleotide," "polynucleotide," and "nucleic acid molecule", used interchangeably herein, refer to polymeric forms of nucleotides of any length, either ribonucleotides or deoxyribonucleotides. Thus, this term comprises, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

"Sequencing," "sequence determination" and the like means determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput digital sequencing" or "next generation sequencing" means sequence determination using methods that determine many (typically thousands to billions) of nucleic acid sequences in an intrinsically parallel manner, e.g. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technologies, Inc., Carlsbad, Calif.); sequencing by synthesis using modified nucleotides (such as commercialized in TruSeq™ and HiSeq™ technology by Illumina, Inc., San Diego, Calif.; HeliScope™ by Helicos Biosciences Corporation, Cambridge, Ma.; and PacBio RS by Pacific Biosciences of California, Inc., Menlo Park, Calif.), sequencing by ion detection technologies (such as Ion Torrent™ technology, Life Technologies, Carlsbad, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

As used herein, the term "barcoded nucleic acid molecule" generally refers to a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence may be a targeted sequence or a non-targeted sequence. The nucleic acid barcode molecule may be coupled to or attached to the nucleic acid molecule comprising the nucleic acid sequence. For example, in the methods and systems described herein, hybridization and reverse transcription of a nucleic acid molecule (e.g., a messenger RNA (mRNA) molecule) of a cell with a nucleic acid barcode molecule (e.g., a nucleic acid barcode molecule containing a barcode sequence and a nucleic acid primer sequence complementary to a nucleic acid sequence of the mRNA molecule) results in a barcoded nucleic acid molecule that has a sequence corresponding to the nucleic acid sequence of the mRNA and the barcode sequence (or a reverse complement thereof). The processing of the nucleic acid molecule comprising the nucleic acid sequence, the nucleic acid barcode molecule, or both, can include a nucleic acid reaction, such as, in non-limiting examples, reverse transcription, nucleic acid extension, ligation, etc. The nucleic acid reaction may be performed prior to, during, or following barcoding of the nucleic acid sequence to generate the barcoded nucleic acid molecule. For example, the nucleic acid molecule comprising the nucleic acid sequence may be subjected to reverse transcription and then be attached to the nucleic acid barcode molecule to generate the barcoded nucleic acid molecule, or the nucleic acid molecule comprising the nucleic acid sequence may be attached to the nucleic acid barcode molecule and subjected to a nucleic acid reaction (e.g., extension, ligation) to generate the barcoded nucleic acid molecule. A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the nucleic acid molecule (e.g., mRNA).

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The terms "coupled," "linked," "conjugated," "associated," "attached," "connected" or "fused," as used herein, may be used interchangeably herein and generally refer to one molecule (e.g., polypeptide, receptor, analyte, etc.) being attached or connected (e.g., chemically bound) to another molecule (e.g., polypeptide, receptor, analyte, etc.).

The term "binding agent," as used herein generally refers to a molecule capable of binding to one or more other molecules (e.g., analytes, receptors, other binding agents, etc.) and that comprises one or more portions. In some cases, a binding agent comprises at least one, at least two, at least three, or at least four portions. Each portion may comprise a polypeptide. The polypeptide of a specific portion may be capable of binding one or more molecules. For example, a polypeptide of a specific portion may bind to a molecule located on a surface of a cell, such as a cell surface protein or receptor (e.g., a CD surface marker such as CD45). A polypeptide of another portion of a binding agent may bind a molecule that may be secreted from a cell (e.g., T cell, B-cell, dendritic cell, etc.). The one or more portions of a binding agent may be directly or indirectly linked to, conjugated to, or fused to one another. For example, a first portion of a binding agent may be directly or indirectly linked to, conjugated to, or fused to a second portion of the binding agent. Moreover, the terms "binding agent," "polypeptide," and "antibody" may be used interchangeably herein.

The term "cell bead," as used herein, generally refers to a hydrogel, polymeric, or crosslinked material that comprises (e.g., encapsulates, contains, etc.) a biological particle (e.g., a cell, a nucleus, a fixed cell, a cross-linked cell), a virus, components of or macromolecular constituents of or derived from a cell or virus. For example, a cell bead may comprise a virus and/or a cell. In some cases, a cell bead comprises a single cell. In some cases, a cell bead may comprise multiple cells adhered together. A cell bead may include any type of cell, including without limitation prokaryotic cells, eukaryotic cells, bacterial, fungal, plant, mammalian, or other animal cell types, mycoplasmas, normal tissue cells, tumor cells, immune cells, e.g., a T-cell (e.g., CD4 T-cell, CD4 T-cell that comprises a dormant copy of human immunodeficiency virus (HIV)), a B cell, or a dendritic cell, a fixed cell, a cross-linked cell, a rare cell from a population of cells, or any other cell type, whether derived from single cell or multicellular organisms. Furthermore, a cell bead may comprise a live cell, such as, for example, a cell may be capable of being cultured. Moreover, in some examples, a cell bead may comprise a derivative of a cell, such as one or more components of the cell (e.g., an organelle, a cell protein, a cellular nucleic acid, genomic nucleic acid, messenger ribonucleic acid, a ribosome, a cellular enzyme, etc.). In some examples, a cell bead may comprise material obtained from a biological tissue, such as, for example, obtained from a subject. In some cases, cells, viruses or macromolecular constituents thereof are encapsulated within a cell bead. Encapsulation can be within a polymer or gel matrix that forms a structural component of the cell bead. In some cases, a cell bead is generated by fixing a cell in a fixation medium or by cross-linking elements of the cell, such as the cell membrane, the cell cytoskeleton, etc.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The terms "antigen binding fragment," "epitope binding fragment," or "antibody fragment," as used herein, may be used interchangeably and generally refer to a portion of a complete antibody (e.g., comprising each domain of the light and heavy chains respectively) capable of binding the same epitope/antigen as the complete antibody, albeit not necessarily to the same extent. Although multiple types of epitope binding fragments are possible, an epitope binding fragment typically comprises at least one pair of heavy and light chain variable regions (VH and VL, respectively) held together (e.g., by disulfide bonds) to preserve the antigen binding site and does not contain all or a portion of the Fc region. Epitope binding fragments of an antibody can be obtained from a given antibody by any suitable technique (e.g., recombinant DNA technology or enzymatic or chemical cleavage of a complete antibody), and typically can be screened for specificity in the same manner in which complete antibodies are screened. In some embodiments, an epitope binding fragment comprises an F(ab')$_2$ fragment, Fab' fragment, Fab fragment, Fd fragment, or Fv fragment. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific antigen binding ability to the polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

The term "analyte," as used herein, generally refers to a species of interest for detection. An analyte may be biological analyte, such as a nucleic acid molecule or protein. An analyte may be an atom or molecule. An analyte be a subunit of a larger unit, such as, e.g., a given sequence of a polynucleotide sequence or a sequence as part of a larger sequence. An analyte of the present disclosure includes a secreted analyte, a soluble analyte, and/or an extracellular analyte.

The term "about" as used herein refers to the usual error range for the respective value readily known to the skilled person in this technical field. Reference to "about" a value or parameter herein comprises (and describes) embodiments that are directed to that value or parameter per se.

As used herein, the singular forms "a," "an," and "the" comprise plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be comprised in the smaller ranges, and are also encompassed within the claimed subject matter, subject to any specifically excluded limit in the stated range. Where the stated range comprises one or both of the limits, ranges excluding either or both of those comprised limits are also comprised in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

EXAMPLES

The following examples are included for illustrative purposes only and are not intended to limit the scope of the present disclosure.

Example 1: Labeling Monoclonal Antibody with Reporter Barcode Sequence

This Example describes the labeling strategy that is used to label a candidate mAb of interest. The labeling of the candidate mAb permits detection, isolation, and identification of the mAb in downstream analyses.

The candidate antibody can be in IgG format. If the antibody candidate is natively IgM or IgD or IgA, the antibody candidate can first be converted to IgG format.

The candidate mAb is labeled with a reporter oligonucleotide comprising a reporter barcode sequence. The preparation of antibody-oligonucleotide conjugates may involve site-directed conjugation methods, where the oligonucleotide is conjugated to either n-linked glycans or internally-expressed protein tags. Non-site directed conjugation approaches may be used to build up larger libraries of oligonucleotide-conjugated antibodies. Several suitable bioorthogonal conjugation methods have been established, where the most common are based on maleimide, tetrazine, or click chemistry reagents.

Conjugation is also possible via a reactive thiol (sulfhydryl) group. Antibodies contain oxidized sulfhydryl (—SH) groups present as disulfide (S—S) bridges, which contribute to the tertiary structure of the antibody. These disulfide bridges can be reduced to expose their reactive groups by a reducing agent (e.g., 2-ME/SDS). Antibodies can be selectively cleaved to create either two half antibody molecules or smaller antibody fragments such as F(ab'). Conjugation using the 'hinge' region free/reduced —SH group can orient the attached oligonucleotide away from the antigen-binding regions, hence preventing steric hindrance and preserving activity.

An alternative method of site-directed conjugation can occur at carbohydrate residues, which occur mainly in the Fc region, as they are less susceptible to steric hindrance due to their remoteness from antigen-binding sites. For conjugation via this method, the carbohydrate group can be oxidized to an aldehyde (—CHO) using periodic acid. In some experiments, Ab-oligos produced via site-specific conjugation techniques can have distinct advantages for in vivo applications.

The candidate mAb of interest can also be labeled with a fluorophore (e.g., PE or APC) or quantum dot (e.g., Qdot) via any conventional conjugation technique, such as via SMCC-activated conjugation.

Example 2: Validating Candidate mAb Binding to Target Protein of Interest

Provided in this example is a method of selecting and/or validating antibody candidates that bind to a target protein of interest.

One or more populations of cells expressing the target protein of interest and one or more populations of cells that do not express the target protein of interest should be included in the analysis. For example, the following 4 cell populations can be engineered or selected for analysis: (1) target cells that natively express the target protein (target+), (2) cells natively expressing the target whose expression has been knocked down or out using a Perturb-Seq or CRISPR guide RNA (target+guide+), (3) cells that are target-null or do not natively express the target (target−), and (4) cells that are target-null or do not natively express the target plus the Perturb-Seq or CRISPR guide RNA (target−guide+). This combination of single cell populations will allow the assessment of cross-reactivity/false-positive binding in the subsequent analysis.

Target cells that non-natively express the target via transient transfection or transduction(target−expression+) can be used as an additional population, or as a substitute for the population of cells that natively express the target protein (target+) if such a population is not available.

The selected combination of cell populations are stained with the exemplary reporter oligonucleotide labeled mAb described in Example 1 above. Optionally, the resulting mAb-bound cells can then be purified via FACS (using the mAb-attached fluorophore to identify binding) or via MACS with a secondary antibody against the fluorophore or other biomolecule used to retain mAb-binding cells which could then be eluted and captured on the Chromium controller.

In some cases, it may be desirable to ensure equal representation of all included cell populations for downstream analysis. In this case, markers specific to each of the 4 populations can be used to identify each cell population and/or to isolate equal numbers of cells from each population via FACS or MACS to ensure equal representation of all 4 cell populations.

Single cells may be partitioned for analysis via any suitable method. Methods of partitioning that provide for the compartmentalization, depositing or partitioning of the nucleic acid contents of individual cells from a sample material containing cells, into discrete compartments or partitions, where each partition maintains separation of its own contents from the contents of other partitions have been described (for example, in U.S. Pat. No. 10,550,429, incorporated herein by reference in its entirety). Cell partitioning may be performed on a Chromium system using Chromium workflows (10× Genomics). In brief, the cells can be partitioned into nanoliter-scale droplets containing uniquely barcoded beads called GEMs (Gel Bead-In Emulsions) in order to prepare next generation sequencing libraries in parallel.

As shown in FIG. 12A and described in Example 1 above, the candidate mAb can be labeled with a reporter oligonucleotide 1220 that comprises a barcode sequence 1212 that identifies the candidate mAb 1210 and a capture handle sequence 1213. The capture handle sequence 1213 may be configured to hybridize to a complementary sequence, such as a capture sequence 1223 present on a nucleic acid barcode molecule 1290. In some instances, the reporter oligonucleotide 1220 comprises one or more additional functional sequences, such as those described elsewhere herein.

In an example as shown in FIG. 12B, capture sequence 1223 may be complementary to the capture handle sequence 1213. In an example, a reverse transcription reaction can generate a barcoded nucleic acid molecule comprising cell (e.g., partition specific) common barcode sequence 1222 (or a reverse complement thereof) and a sequence of the reporter oligonucleotide 1220 (or a portion thereof). Sequencing can then be used to identify the bound or internalized mAbs and their associated cells or partitions based on their reporter oligonucleotide barcode sequence and common (e.g., partition specific) barcode sequence. In some experiments, sequencing of the individually partitioned cells can be used to identify mutations introduced by Perturb-Seq or CRISPR guides or reporter oligonucleotides associated with the CRISPR guides.

Example 3: Characterizing Monoclonal Antibody Binding to Engineered Protein Variants by Staining Cells with the Candidate mAb Provided in this example is a method of assessing the binding of an antibody to genetic variants of a given target via Perturb-Seq (e.g., to perform epitope mapping using engineered variants of the target protein, or to assess binding to common genetic variants of a given target).

First, an antibody is labeled with a reporter barcode sequence and a fluorophore as described in Example 1 above. The monoclonal antibody can be a monoclonal antibody (mAb), a recombinant bispecific monoclonal antibody such as a Bi-specific T-cell engager (BiTE), a simultaneous multiple interaction T-cell engaging (SMITE) bispecific antibody, or a bi-, tri-, or tetra-valent antibody.

A panel of guides (e.g., CRISPR or Perturb-Seq guides) can be used to engineer protein variants and to assess the binding of the monoclonal antibody to perform epitope mapping or to assess whether the mAb can bind common genetic variants of a given target. The target-expressing cell library generated using the panel of guides can be stained with the reporter molecule (e.g., reporter barcode sequence) labeled candidate antibody. Cells bound by the antibody can be partitioned for analysis as described in Example 2 above. Optionally, different cell populations can be isolated prior to partitioning (e.g., by FACS or MACS). The correlation between binding of the candidate antibody and particular mutations in the target protein can be identified based on sequencing for the reporter barcode sequence and CRISPR guide RNA barcodes, allowing mapping of the target protein epitope.

In the case of target cells that natively express the target of interest, knockdown can be achieved by a reporter barcode sequence-detectable Perturb-Seq guide. This guide could also be attached to a molecule known to be internalized by the target-expressing cells.

Perturb-Seq allows combination of a pooled CRISPR screen with scRNA-seq by encoding the identity of the perturbation on an expressed guide barcode. Methods of performing Perturb-Seq have been described in detail, for example, in WO2018119447; WO2019157529; WO2018112423A; and Replogle et al. Combinatorial single-cell CRISPR screens by direct guide RNA capture and targeted sequencing. Nat Biotechnol 38, 954-961 (2020); which are herein incorporated by reference in their entirety.

Example 4: Characterizing Monoclonal Antibody Binding to Engineered Protein Variants by Binding of Secreted Antibody Provided in this example is a method of characterizing the binding of an antibody to genetic variants, wherein the assay is performed using engineered B cells expressing the monoclonal antibody of interest and the target of interest.

To implement the assay using B cells expressing the monoclonal antibody of interest and the target of interest, the mAb of interest can first be engineered into the B cell of choice using standard genetic engineering techniques (e.g., CRISPR/Cas9-mediated double-strand cleavage and homology-directed repair). In this Example, the mAb must be in IgG format and must contain the 6th exon of the immunoglobulin heavy chain constant region IGHG1/2/3/4 so that the antibody could be expressed and secreted in IgG format. The 6th exon of the target region comprises a secretory sequence (e.g., a secretory signal peptide) to allow secretion of the antibody of interest. The target of interest can be engineered into the same cell, again using standard genetic engineering techniques (e.g., CRISPR/Cas9-mediated gene double-strand cleavage and homology-directed repair).

In this example, secretion of the mAb would lead to self-binding, where the secreted mAb binds the target ligand on the same cell. This could be detected via a reporter molecule labeled anti-IgG monoclonal antibody. For example, the anti-IgG monoclonal antibody could be labeled with a reporter oligonucleotide.

Transduction of the engineered B cell with a Perturb-Seq vector would knock down the target ligand and lead to secretion of the mAb with no target binding (or no motif conjugation as described below).

Figure 14:
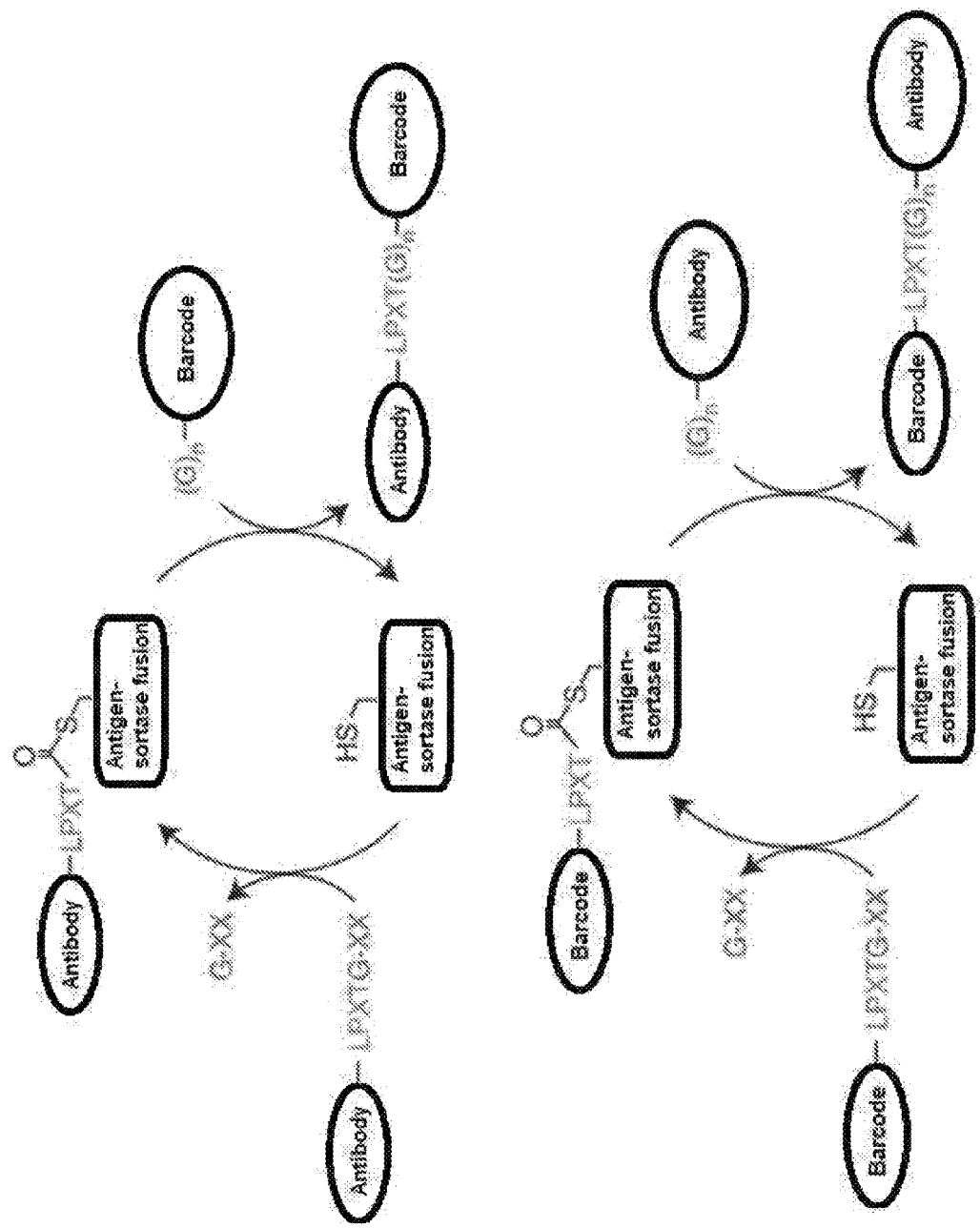
FIG. 14 shows exemplary uses of sortase labeling to label an antibody with an oligonucleotide barcode. The antigen can be fused to a sortase, and the antibody of interest can be tagged with a sortase recognition sequence (LPXTG) or a sortase acceptor peptide (e.g., an oligoglycine, $(G)_n$). The antibody and cell population expressing the sortase-fused antigen can be incubated together in the presence of an oligonucleotide-barcode fused to a sortase recognition sequence (LPXTG) or a sortase acceptor peptide (e.g., an oligoglycine, $(G)_n$). Binding of the antibody to the antigen will result in labeling of the antibody with the oligonucleotide barcode. In some cases, the antibody can be a secreted antibody engineered in to the cell line, and binding of the secreted antibody to the antigen can be detected based on labeling of the antibody with the oligonucleotide barcode.

In some examples of this method, binding of the secreted mAb to its target protein can be detected by motif conjugation. In an exemplary experiment as shown in FIG. 14, the antigen can be fused to a sortase, and the antibody of interest can be tagged with a sortase acceptor peptide (e.g., an oligoglycine, $(G)_n$). The antibody and cell population expressing the sortase-fused antigen can be incubated together in the presence of an oligonucleotide-barcode fused to a sortase recognition sequence (LPXTG). Binding of the antibody to the antigen will result in labeling of the antibody with the oligonucleotide barcode. In another configuration, the antibody can be tagged with the sortase recognition sequence and the oligonucleotide barcode can be tagged with the sortase acceptor peptide. In some cases, the antibody can be a secreted antibody engineered in to the cell line, and binding of the secreted antibody to the antigen can be detected based on labeling of the antibody with the oligonucleotide barcode.

In another exemplary experiment, an antibody of interest can be fused to a sortase, and the candidate antigen can be tagged with a sortase acceptor peptide (e.g., an oligoglycine, $(G)_n$). The antibody and cell population expressing the antigen can be incubated together in the presence of an oligonucleotide-barcode fused to a sortase recognition sequence (LPXTG). Binding of the antibody to the antigen will result in labeling of the antigen with the oligonucleotide barcode. In another configuration, the antigen can be tagged with the sortase recognition sequence and the oligonucleotide barcode can be tagged with the sortase acceptor peptide. In some cases, the antibody can be a secreted antibody engineered in to the cell line, and binding of the secreted antibody to the antigen can be detected based on labeling of the antigen with the oligonucleotide barcode.

In another exemplary experiment, an antibody of interest can be labeled with a reporter oligonucleotide and a peptide tag (e.g. SpyTag or SnoopTag), and the candidate antigen can be labeled with a corresponding binding partner (e.g., SpyCapture or SnoopCapture, respectively) capable of spontaneously forming an isopeptide bond when it binds to the corresponding peptide tag. Thus, cells expressing a secreted binding molecule that binds to an antigen expressed on the cell surface will be labeled by the binding molecule and its attached reporter oligonucleotide. In another exemplary experiment, a third peptide can be expressed separately that acts as a ligase to couple the peptide tag and binding partner in an isopeptide reaction. This system can allow the use of smaller peptide tags. In some embodiments, the ligase peptide could be added to the cell medium.

Suitable SpyTag/SpyCapture, SnoopTag/SnoopCapture, and three part SpyTag/KTag/SpyLigase or SnoopTagJr/DogTag/SnoopLigase systems have been described, for example in WO2011/098772, U.S. Pub. No. 20200115422, and U.S. patent Ser. No. 10/526,379, herein incorporated by reference in their entirety).

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method of analyzing the target binding specificity and/or affinity of an antibody or antigen-binding fragment thereof, comprising:
   (a) providing a cell population, wherein the cell population comprises a mixture of:
      (i) a first subset of cells comprising a candidate antigen or epitope and a nucleic acid molecule indicative of expression or presence of the candidate antigen or epitope, wherein the first subset of cells is engineered or otherwise modified to express the candidate antigen or epitope, and
      (ii) a second subset of cells lacking the candidate antigen or epitope and the nucleic acid molecule indicative of expression or presence of the candidate antigen or epitope;
   (b) contacting the cell population of (a) with at least one antibody or antigen-binding fragment thereof, wherein the at least one antibody or antigen-binding fragment thereof is coupled to an oligonucleotide comprising an antibody-specific barcode sequence, and wherein the antibody binds to the candidate antigen or epitope;
   (c) partitioning the cells of the population of (b) into a plurality of partitions, wherein a partition of the plurality of partitions comprises a cell of the population and a plurality of nucleic acid molecules comprising a partition-specific barcode sequence;
   (d) generating a first barcoded nucleic acid molecule using the oligonucleotide comprising the antibody-specific barcode sequence and a first nucleic acid molecule of the plurality of nucleic acid molecules wherein the first barcoded nucleic acid molecule comprises the:
      (i) partition-specific barcode sequence or reverse complement thereof, and
      (ii) antibody-specific barcode sequence or reverse complement thereof;
   (e) generating a second barcoded nucleic acid molecule using the nucleic acid molecule indicative of expression or presence of the candidate antigen or epitope and a second nucleic acid molecule of the plurality of nucleic acid molecules, wherein the second barcoded nucleic acid molecule comprises the partition-specific barcode sequence or reverse complement thereof.

2. The method according to claim 1, wherein the sequences of the first barcoded nucleic acid molecule and the second barcoded nucleic acid molecule are determined.

3. The method according to claim 1, wherein the oligonucleotide comprising the antibody-specific barcode sequence further comprises a capture sequence.

4. The method according to claim 3, wherein the capture sequence is complementary to a sequence found on the plurality of nucleic acid molecules comprising the partition-specific barcode sequence.

5. The method according to claim 1, wherein the plurality of nucleic acid molecules comprising the partition-specific barcode sequence are coupled to a bead.

6. The method according to claim 5, wherein the bead is a gel bead.

7. The method according to claim 1, wherein expression of the candidate antigen or epitope has been knocked out in the second subset of cells.

8. The method according to claim 7, wherein expression of the candidate antigen or epitope has been knocked out using a guide RNA.

9. The method of claim 8, wherein the guide RNA comprises a barcode sequence.

10. The method according to claim 1, wherein the nucleic acid molecule that is indicative of expression or presence of the candidate antigen or epitope is a ribonucleic acid (RNA) molecule.

11. The method according to claim 10, wherein the RNA molecule is a messenger RNA (mRNA) molecule.

12. The method of claim 1, wherein the candidate antigen or epitope comprises a polynucleotide, a polypeptide, a lipid, a carbohydrate, a small molecule, or one or more other organic or inorganic molecules, or any combination, complex, or conjugate thereof.

13. The method of claim 1, wherein a partition of the plurality of partitions further comprises a nucleic acid molecule comprising a nucleic acid sequence indicative of no expression of the candidate antigen or epitope by the cell.

14. The method of claim 13, wherein the nucleic acid molecule comprising a nucleic acid sequence indicative of no expression of the candidate antigen or epitope by the cell further comprises a barcode sequence.

15. The method of claim 14, wherein a barcoded nucleic acid molecule is generated in the partition, wherein the barcoded nucleic acid molecule comprises the:
   (i) nucleic acid sequence indicative of no expression of the candidate antigen or epitope by the cell, and
   (ii) barcode sequence.

16. The method of claim 1, wherein after (b) one or more cells bound by the antibody or antigen-binding fragment thereof are enriched, purified, isolated, sorted, and/or separated.

17. The method of claim 16, wherein the antibody or antigen-binding fragment thereof comprises a label attached thereto.

18. The method of claim 17, wherein the label comprises a fluorophore.

19. The method of claim 18, wherein the one or more cells bound by the antibody or antigen-binding fragment thereof are sorted or purified using fluorescence-activated cell sorting (FACS) or magnetic-activated cell sorting (MACS).

* * * * *